US007883870B2

(12) United States Patent
Raoult et al.

(10) Patent No.: US 7,883,870 B2
(45) Date of Patent: Feb. 8, 2011

(54) **MOLECULAR IDENTIFICATION OF *STAPHYLOCOCCUS*-GENUS BACTERIA**

(75) Inventors: Didier Raoult, Marseilles (FR); Michel Drancourt, Marseilles (FR)

(73) Assignee: Biomerieux, Marcy l'Etoile (FR)

( * ) Notice: Subject to any disclaimer, the term of this patent is extended or adjusted under 35 U.S.C. 154(b) by 864 days.

(21) Appl. No.: 10/488,588

(22) PCT Filed: Sep. 5, 2002

(86) PCT No.: PCT/FR02/03012

§ 371 (c)(1),
(2), (4) Date: Mar. 5, 2004

(87) PCT Pub. No.: WO03/020972

PCT Pub. Date: Mar. 13, 2003

(65) Prior Publication Data

US 2004/0254360 A1    Dec. 16, 2004

(30) Foreign Application Priority Data

Sep. 6, 2001    (FR)    ................................... 01 11514

(51) Int. Cl.
*C12P 19/34* (2006.01)
*C07H 21/04* (2006.01)
(52) U.S. Cl. .................. 435/91.2; 536/24.32; 536/24.33
(58) Field of Classification Search ................. 536/23.1
See application file for complete search history.

(56) References Cited

U.S. PATENT DOCUMENTS 6,248,526 B1 * 6/2001 Weimer ......................... 435/6

FOREIGN PATENT DOCUMENTS

| WO | WO 9820157 A2 * | 5/1998 |
|----|-----------------|--------|
| WO | WO 98 23738 A2 | 6/1998 |
| WO | WO 99/05316 A1 | 2/1999 |
| WO | WO 01/34809 A2 | 5/2001 |

OTHER PUBLICATIONS

Sequence aligment AF325882.*
Sequence Alignment Acc# AF325897 100% sequence identity with SEQ ID No. 10.*
Mollet et al. *rpoB* sequence analysis as novel basis for bacterial identification, Molecular Microbiology vol. 26, No. 5, pp. 1005-1011, 1997.*
Wichelaus et al. Molecular Characterization of *rpoB* Mutations Conferring Cross-Resistance to Rifamycins on Methicillin—Resistant *Staphylococcus aureus*, Antimicrobial Agents and Chemotherapy, vol. 43, No. 11, pp. 2813-2816, Nov. 1999.*
Dahllof et al. *RpoB*-Based Microbial Community Analysis Avoids Limitations Inherent in 16S rRNA Gene Intraspecies Heterogeneity, Applied and Environmental Microbiology, vol. 66, No. 8, pp. 3376-3380, Aug. 2000.*
Attwood, T. K. ,Science vol. 290, Oct. 20, 2000.*
Van de Loo et al. ,Proc. Natl. Acad. Sci 1995.*
677848 [online] Feb. 17, 1995 [retrieved on Feb. 12, 2009] from http://www.ncbi.nlm.nih.gov/entrez/viewer.fcgi?677848:OLDID:1218121.*
17225225 [online] Dec. 2, 2001 [retrieved on Feb. 12, 2009] from http://www.ncbi.nlm.nih.gov/entrez/viewer.fcgi?17225225:OLD02:2479147.*
17225231 [online] Dec. 2, 2001 [retrieved on Feb. 12, 2009] from http://www.ncbi.nlm.nih.gov/entrez/viewer.fcgi?17225231:OLD02:2479150.*
17225229 [online] Dec. 2, 2001 [retrieved on Feb. 12, 2009] from http://www.ncbi.nlm.nih.gov/entrez/viewer.fcgi?17225229:OLD02:2479149.*
17225227 [online] Dec. 2, 2001 [retrieved on Feb. 12, 2009] from http://www.ncbi.nlm.nih.gov/entrez/viewer.fcgi?17225227:OLD02:2479148.*
9664760 [online] Aug. 3, 2000 [retrieved on Feb. 12, 2009] from http://www.ncbi.nlm.nih.gov/entrez/viewer.fcgi?9664760:OLD02:2090768.*
9664762 [online] Aug. 3, 2000 [retrieved on Feb. 12, 2009] from http://www.ncbi.nlm.nih.gov/entrez/viewer.fcgi?9664762:OLD02:2090770.*
9664717 [online] Aug. 3, 2000 [retrieved on Feb. 12, 2009] from http://www.ncbi.nlm.nih.gov/entrez/viewer.fcgi?9664717:OLD02:2090725.*
9623516 [online] Aug. 1, 2000 [retrieved on Feb. 12, 2009] from http://www.ncbi.nlm.nih.gov/entrez/viewer.fcgi?9623516:NCBI:2029109.*
17225283 [online] Dec. 2, 2001 [retrieved on Feb. 12, 2009] from http://www.ncbi.nlm.nih.gov/entrez/viewer.fcgi?17225283:NCBI:2783237.*
17225277 [online] Dec. 2, 2001 [retrieved on Feb. 12, 2009] from http://www.ncbi.nlm.nih.gov/entrez/viewer.fcgi?17225277:OLD02:2479173.*
17225281 [online] Dec. 2, 2001 [retrieved on Feb. 12, 2009] from http://www.ncbi.nlm.nih.gov/entrez/viewer.fcgi?17225281:NCBI:2783236.*
17225287 [online] Dec. 2, 2001 [retrieved on Feb. 12, 2009] from http://www.ncbi.nlm.nih.gov/entrez/viewer.fcgi?17225287:NCBI:2783239.*
17225285 [online] Dec. 2, 2001 [retrieved on Feb. 12, 2009] from http://www.ncbi.nlm.nih.gov/entrez/viewer.fcgi?17225285:NCBI:2783238.*

(Continued)

*Primary Examiner*—Samuel C Woolwine
(74) *Attorney, Agent, or Firm*—Oliff & Berridge, PLC

(57) ABSTRACT

The invention relates to a method of detecting, by means of molecular identification, a bacterium from one of the *Staphylococcus*-type species. The inventive method is characterised in that the following are used: a fragment of the rpoB gene of said bacterium, comprising a nucleotide sequence selected from one of the SEQ. ID. No. 11 to 39 sequences, the reverse sequences and the complementary sequences; or an oligonucleotide comprising a sequence having at least 12 consecutive nucleotide patterns included in one of the SEQ. ID. No. 7 to 10 sequences, in which N represents a nucleotide selected from inosine and an equimolar mixture of 4 different nucleotides selected from A, T, C or G and from the oligonucleotides of the reverse sequences and complementary sequences.

20 Claims, 1 Drawing Sheet

OTHER PUBLICATIONS

17225279 [online] Dec. 2, 2001 [retrieved on Feb. 12, 2009] from http://www.ncbi.nlm.nih.gov/entrez/viewer.fcgi?db=nuccore&id=17225279.*
17225235 [online] Dec. 2, 2001 [retrieved on Feb. 15, 2009] from http://www.ncbi.nlm.nih.gov/entrez/viewer.fcgi?17225235:OLD02:2479152.*
17225275 [online] Dec. 2, 2001 [retrieved on Feb. 15, 2009] from http://www.ncbi.nlm.nih.gov/entrez/viewer.fcgi?17225275:OLD02:2479172.*
17225269 [online] Dec. 2, 2001 [retrieved on Feb. 15, 2009] from http://www.ncbi.nlm.nih.gov/entrez/viewer.fcgi?17225269:OLD02:2479169.*
17225239 [online] Dec. 2, 2001 [retrieved on Feb. 15, 2009] from http://www.ncbi.nlm.nih.gov/entrez/viewer.fcgi?17225239:OLD02:2479154.*
17225271 [online] Dec. 2, 2001 [retrieved on Feb. 15, 2009] from http://www.ncbi.nlm.nih.gov/entrez/viewer.fcgi?17225271:OLD02:2479170.*
17225255 [online] Dec. 2, 2001 [retrieved on Feb. 15, 2009] from http://www.ncbi.nlm.nih.gov/entrez/viewer.fcgi?17225255:OLD02:2479162.*
17225259 [online] Dec. 2, 2001 [retrieved on Feb. 15, 2009] from http://www.ncbi.nlm.nih.gov/entrez/viewer.fcgi?17225259:OLD02:2479164.*
17225265 [online] Dec. 2, 2001 [retrieved on Feb. 15, 2009] from http://www.ncbi.nlm.nih.gov/entrez/viewer.fcgi?17225265:OLD02:2479167.*
17225253 [online] Dec. 2, 2001 [retrieved on Feb. 15, 2009] from http://www.ncbi.nlm.nih.gov/entrez/viewer.fcgi?17225253:OLD02:2479161.*
17225233 [online] Dec. 2, 2001 [retrieved on Feb. 15, 2009] from http://www.ncbi.nlm.nih.gov/entrez/viewer.fcgi?17225233:OLD02:2479151.*
17225257 [online] Dec. 2, 2001 [retrieved on Feb. 15, 2009] from http://www.ncbi.nlm.nih.gov/entrez/viewer.fcgi?17225257:OLD02:2479163.*
17225237 [online] Dec. 2, 2001 [retrieved on Feb. 15, 2009] from http://www.ncbi.nlm.nih.gov/entrez/viewer.fcgi?17225237:OLD02:2479153.*
17225263 [online] Dec. 2, 2001 [retrieved on Feb. 15, 2009] from http://www.ncbi.nlm.nih.gov/entrez/viewer.fcgi?17225263:OLD02:2479166.*
17225249 [online] Dec. 2, 2001 [retrieved on Feb. 15, 2009] from http://www.ncbi.nlm.nih.gov/entrez/viewer.fcgi?17225249:OLD02:2479159.*
17225245 [online] Dec. 2, 2001 [retrieved on Feb. 15, 2009] from http://www.ncbi.nlm.nih.gov/entrez/viewer.fcgi?17225245:OLD02:2479157.*
17225241 [online] Dec. 2, 2001 [retrieved on Feb. 15, 2009] from http://www.ncbi.nlm.nih.gov/entrez/viewer.fcgi?17225241:OLD02:2479155.*
17225261 [online] Dec. 2, 2001 [retrieved on Feb. 15, 2009] from http://www.ncbi.nlm.nih.gov/entrez/viewer.fcgi?17225261:OLD02:2479165.*
17225273 [online] Dec. 2, 2001 [retrieved on Feb. 15, 2009] from http://www.ncbi.nlm.nih.gov/entrez/viewer.fcgi?17225273:OLD02:2479171.*
17225243 [online] Dec. 2, 2001 [retrieved on Feb. 15, 2009] from http://www.ncbi.nlm.nih.gov/entrez/viewer.fcgi?17225243:OLD02:2479156.*
17225267 [online] Dec. 2, 2001 [retrieved on Feb. 15, 2009] from http://www.ncbi.nlm.nih.gov/entrez/viewer.fcgi?17225267:OLD02:2479168.*
17225251 [online] Dec. 2, 2001 [retrieved on Feb. 15, 2009] from http://www.ncbi.nlm.nih.gov/entrez/viewer.fcgi?17225251:OLD02:2479160.*
17225247 [online] Dec. 2, 2001 [retrieved on Feb. 15, 2009] from http://www.ncbi.nlm.nih.gov/entrez/viewer.fcgi?17225247:OLD02:2479158.*
21307733 [online] Jun. 1, 2002 [retrieved on Feb. 15, 2009] from http://www.ncbi.nlm.nih.gov/entrez/viewer.fcgi?21307733:NCBI:3493085.*
Mollet et al.; "*rpoB* sequence analysis as a novel basis for bacterial identification"; Molecular Microbiology, Blackwell Scientific Oxford, GB; vol. 26, No. 5; 1997; pp. 1005-1011; XP-000913977.
Rowland et al.; "Comparative sequence analysis and predicated phylogeny of the DNA-dependent RNA polymerase beta subunits of *Staphylococcus aureaus* and other eubacteria"; Biochemical Society Transactions; vol. 21, No. 1; Feb. 1993; pp. 40S; XP-008003308.
Drancourt et al.; "*rpoB* Gene Sequence-Based Identification of Staphylococcus Species"; Journal of Clinical Microbiology; vol. 40, No. 4, Apr. 2002; pp. 1333-1138; XP-008003295.
IBIS-Integrated Biotechnological Information Services, results of SEQ.ID.N.7: GENESEQN Accession No. AAF25785, Dec. 21, 2000.
IBIS-Integrated Biotechnological Information Services, results of SEQ.ID.N.8: GENESEQN Accession No. AAN60748, Jul. 3, 1986.
IBIS-Integrated Biotechnological Information Services, results of SEQ.ID.N.9: GENESEQN Accession No. AAV70526, Nov. 12, 1998.
IBIS-Integrated Biotechnological Information Services, results of SEQ.ID.N.10: GENESEQN Accession No. ABL36723, Oct. 20, 1999.

* cited by examiner

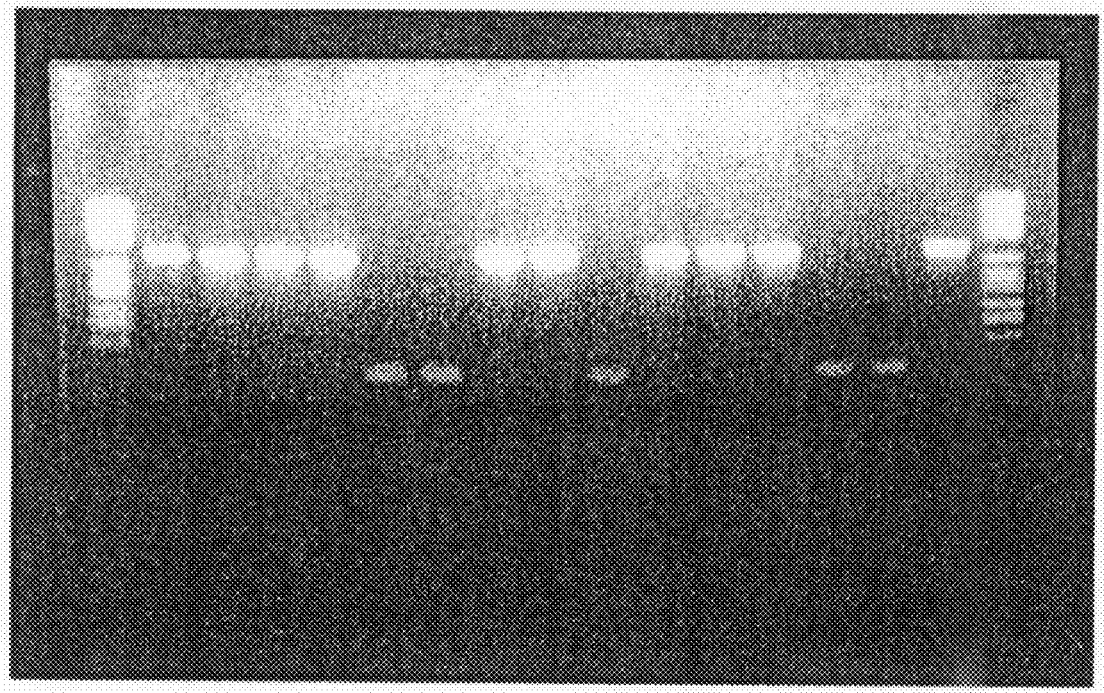

SEQUENCE LISTING

```
<160> NUMBER OF SEQ ID NOS: 85

<210> SEQ ID NO 1
<211> LENGTH: 25
<212> TYPE: DNA
<213> ORGANISM: Artificial Sequence
<220> FEATURE:
<223> OTHER INFORMATION: consensus primer

<400> SEQUENCE: 1
aaacttaata gaaattcaaa ctaaa                                             25

<210> SEQ ID NO 2
<211> LENGTH: 20
<212> TYPE: DNA
<213> ORGANISM: Artificial Sequence
<220> FEATURE:
<223> OTHER INFORMATION: consensus primer

<400> SEQUENCE: 2
atctggtaaa gcattaccaa                                                   20
```

<210> SEQ ID NO 3
<211> LENGTH: 3791
<212> TYPE: DNA
<213> ORGANISM: Staphylococcus saccharolyticus

<400> SEQUENCE: 3

| | | | | | |
|---|---|---|---|---|---|
| atgaaactta | atagaaattc | aaactaaatc | ttatgattgg | ttccttaaag | aagggttatt | 60 |
| agaaatgttt | agagacattt | caccaattga | agatttcaca | ggcaacctat | ctttagaatt | 120 |
| tgtagattat | agattaggtg | aaccaaatta | tgatttagaa | gaatctaaaa | atcgtgacgc | 180 |
| tacttatgct | gcacctcttc | gtgtcaaagt | acgtctcatt | attaaagaaa | caggcgaagt | 240 |
| aaaagaacaa | gaagtcttca | tgggtgattt | cccattaatg | acagacacag | gtacatttgt | 300 |
| tatcaatggt | gctgagcgtg | ttatcgtgtc | tcaattagta | cgttcaccat | ctgtttattt | 360 |
| caacgaaaaa | attgataaaa | acggtcgtga | aaattatgat | gcgactatta | ttcctaaccg | 420 |
| tggtgcttgg | ttagaatatg | aaacagatgc | taaagatgtc | gtttatgttc | gtatcgatag | 480 |
| aacacgtaaa | ttaccattaa | ctgtattgtt | acgtgcgcta | ggtttctcaa | ctgatcaaga | 540 |
| aatcgttgat | ttaataggag | acagtgaata | tttacgtaat | acattagaaa | aagatggaac | 600 |
| tgaaaataca | gaacaagctt | tattagaaat | ttatgaacgt | ttgcgtcctg | gcgaaccacc | 660 |
| aacagtagaa | aatgctaaaa | gcttattata | ttcacgtttc | ttcgatccta | aacgctatga | 720 |
| tttagcaagt | gtaggtcgtt | ataaagctaa | caaaaagtta | catttaaaac | accgtttatt | 780 |
| taatcaaaaa | ctagcagaac | caattgttaa | tagtgaaaca | ggtgagattg | tagcggaaga | 840 |
| aggtactgta | cttgatcgtc | gtaaactaga | tgaaatcatg | gacgtattgg | agacaaacgc | 900 |
| taatagcgaa | gtctttgaac | ttgaaggtag | tgtcattgat | gaaccagtag | aaattcaatc | 960 |
| aattaaagta | tatgttccta | atgatgaaga | aggtcgaact | actactgtta | ttggtaatgc | 1020 |
| attaccagac | tcagaagtta | aatgtattac | tccggctgat | attatcgcct | caatgagtta | 1080 |
| cttctttaac | ttattgaatg | gaattggtta | tacagatgat | attgaccact | taggtaatcg | 1140 |
| tcgtttacgt | tcagttggtg | aattactaca | aaaccaattc | cgtatcggtt | tgtctagaat | 1200 |
| ggaacgtgtt | gtacgtgaga | gaatgtcaat | tcaagacact | gattctatca | ctccacaaca | 1260 |
| attaattaat | attcgtccag | tcattgcatc | tattaaagaa | ttttttggta | gttctcaatt | 1320 |
| atctcaattc | atggaccaag | caaacccatt | agctgagttg | actcataaac | gtcgtttatc | 1380 |
| agctctagga | cctggtggtt | taactcgtga | acgcgctcaa | atggaagtac | gtgacgtgca | 1440 |
| ttattctcac | tacggtcgta | tgtgccctat | tgaaacacct | gagggcccaa | acattggatt | 1500 |
| aattaactca | ttatctagtt | atgcaagagt | aaatgaattt | ggttttattg | aaacaccttg | 1560 |
| tcgtaaagtt | gatttagata | ctaattcaat | cactgaccaa | attgactact | aactgctga | 1620 |
| tgaagaagat | agttatgttg | ttgcacaagc | aaactcacgt | cttgatgaaa | atgggtgctt | 1680 |
| cttagatgat | gaagttgttt | gtcgttttcg | tggcaataac | acagtgatgg | ctaaagaaaa | 1740 |
| aatggactat | atggacgtat | cacctaaaca | agtagtttca | gcagctactg | catgtatccc | 1800 |
| attcttagaa | aacgatgact | caaaccgagc | attaatgggt | gcaaacatgc | aacgtcaagc | 1860 |
| agtaccatta | atgaacccag | aagcgccatt | tgttggaaca | ggtatggaac | atgtagcagc | 1920 |
| gcgtgactca | ggtgcagcaa | ttactgctaa | gcatagagga | cgtgttgaac | atgttgagtc | 1980 |
| taatgaagtt | ttagttcgtc | gtttagtaga | agaaaatggt | attgaacatg | aaggtgaatt | 2040 |
| agatcgctat | ccattagcaa | aattcaaacg | ttcaaactct | ggtacatgtt | ataaccaacg | 2100 |

-continued

```
cccaattgtt tctgttggag acgttgttga atataacgaa attttagcag acgtccttc      2160 aatgaacta ggtgaaatgg ctttaggtcg taacgtagtt gtaggtttca tgacttggga      2220
cggttataac tatgaggatg ccgttatcat gagcgaacgt ttagttaaag atgatgtcta     2280
tacatctatt catatcgaag aatacgaatc agaagcacgt gacactaaat taggacctga    2340
agaaattact cgtgatattc ctaatgtgtc tgaaagtgcg cttaaaaact tagacgatcg    2400
tggtatcgtt tatgttggtg ccgaagttaa agatggtgac atcttagtag gcaaagtaac    2460
gcctaaaggt gtaacggaac taacagcaga agaaagatta ttacatgcta ttttcggtga    2520
aaaggctcgt gaagttcgtg atacttcatt acgtgtacca catggtgcag ggggcatcgt    2580
attagatgta aaagtcttca accgtgaaga gggcgatgac actttatctc tggtgtaaaa    2640
tcaattagta cgtgtttata tcgttcaaaa acgtaaaatt catgtagggg ataaaatgtg    2700
cggtcgtcat ggtaataaag gtgttatttc taaaattgtt cctgaagaag atatgccata    2760
cttacctgat ggtcgaccaa tcgacatcat gttaaatcca cttggtgtac cttcacgtat    2820
gaacattgga caagtgctag aattacactt aggtatggct gctaaaaact taggcatcca    2880
cattgcatca ccagtatttg atggtgctaa tgatgatgat gtttggtcta caatcgaaga    2940
ggccggcatg gcacgtgatg gtaagactgt attatatgat gggcgtacgg gtgaaccgtt    3000
tgataaccgt atttctgtag gtgtaatgta catgcttaaa cttgctcaca tggttgatga    3060
caaattgcat gcacgttcaa caggaccata ctcactcgtt acacaacaac cactcggtgg    3120
taaagcacaa tttggtggac aacgtttcgg tgagatggag gtatgggcac ttgaagcata    3180
tggtgctgct tatactttac aagaaatctt aacttataaa tctgacgata cagtaggacg    3240
tgttaaaact tacgaatcta tcgttaaagg tgaaaacatc tctagaccaa gtgttcctga    3300
gtcattccga gtactgatga agaattaca aagtttagga ttagatgtta aagtaatgga    3360
tgagcatgat aatgaaattg aaatggcaga tgttgatgat gaagatgcaa cggaacgcaa    3420
agtagattta caacaaaaaa atgctccgga atcacaaaaa gaaacaactg attaataagc    3480
acttaagata aatgaatact taagggtat gaaatgatta tcatttcaac ttctttaggt    3540
attcgatttc aatgaaagta atcaatcaaa tagcacagct aatctaaatt gaaggaggta    3600
ggctccttga ttgatgtaaa taatttccat tatatgaaaa taggattagc ttcacctgaa    3660
aagattcgtt cttggtcata tggtgaagtt aagaaacctg aaacaataaa ctatcgtact    3720
ttaaagccag aaaaagatgg tcttttctgt gaaagaattt tcggacctac aaaagactgg    3780 gaattttta a                                                         3791
```

<210> SEQ ID NO 4
<211> LENGTH: 3855
<212> TYPE: DNA
<213> ORGANISM: Staphylococcus lugdunensis

<400> SEQUENCE: 4

```
atgtcttatg attggttcct aaaagaaggt ttactagaaa tgttccgtga tatctcacca      60
attgaagatt tcacaggtaa cctatcatta gagtttgtag attacagatt aggtgaacca    120
aagtatgatt tagaagaatc gaaaaatcgt gacgctactt atgctgcacc tcttcgtgtt    180
aaagtgcgtc tcgttataaa agaaacaggt gaagttaaag agcaagaagt atttatggga    240
gacttcccat taatgacaga tacaggtacg tttgttatta atggtgcaga gcgtgttatt    300
gtatcgcaat tagtacgttc accatccgtt tactttaatg aaaaaattga caaaaacgga    360
cgagaaaatt atgatgctac aatcattcct aaccgtggtg cctggttaga atacgaaaca    420
```

-continued

```
gatgctaaag atgttgtcta tgttcgtatt gatagaactc gtaaattgcc attaactgtc    480
ttattacgcg cattaggctt ttcaactgat caagaaattg ttgagttgtt aggcgataac    540
gaatacttgc gtaatacatt agaaaaagac ggaacagaaa acactgaaca agcgttatta    600
gaaatttatg aacgtttacg tcctggtgaa ccaccaacag ttgaaaatgc aaaaagttta    660
ttatattctc gcttcttcga tccgaaacgc tatgatttag caagcgttgg acgttataaa    720
gcgaacaaaa aattgcatct aaaacaccgt ttatttaatc aaaaattagc agagcctatc    780
gtaaacagcg aaacaggtga aattgttgct gaagaaggta ctgtattaga tcgtcgcaaa    840
ttagacgaaa ttatggacgt tcttgaaaca aatgcgaata gtgaagtatt cgaattagaa    900
ggaacagtaa tagacgaacc ggttgaaatt caatcaatca agtctatgt accaaatgat    960 gaagaaggtt gtacaacaac gataattggt aatgctttac cagattcaga agtgaaatgt   1020
atcacacctg cagatattat ttcttctatg agttacttct tcaacttatt agctggcatt   1080
ggttacacgg atgatatcga tcatttaggt aaccgtcgtt tacgttcagt tggtgagtta   1140
ttgcaaaacc aattccgtat tggtttatca agaatggaac gtgttgtgcg tgaaagaatg   1200
tcaattcaag ataccgaatc tatcacacca caacaattaa ttaatattag accagttatt   1260
gcatcaatta aagaattctt tggtagttct caattatcac aattcatgga ccaagctaac   1320
ccattagcag aattaacaca caaacgtcgt ttatctgcgt taggacctgg tggtttaaca   1380
cgtgaacgtg cacaaatgga agttcgtgac gtgcattatt ctcactatgg ccgtatgtgt   1440
ccgattgaaa caccagaggg tccaaacatt ggtttgatta actcattatc tagttatgcg   1500
cgtgtcaacg agtttggctt tattgaaacg ccttatcgta agtagatat tgatacaaat   1560 gcaatcacag atcaaattga ctacttaact gctgatgaag aagacagtta tgtcgttgca   1620
caagcgaact ctcgccttga tgaaaatggt cgtttcttag atgatgaagt agtatgccgt   1680
ttccgcggta taatactgt tatggctaaa gaaaaaatgg actacatgga tgtatctcct   1740
aaacaagttg tttcagctgc gacagcatgt attccattct tagagaacga tgactctaac   1800
cgtgcattga tgggtgcaaa catgcaacgt caagcagttc cgttgatgaa ccctgaagcg   1860
ccgttcgtag gaacaggtat ggagcatgtt gctgctcgtg actctggtgc tgcgattact   1920
gcaaaataca gaggtcgtgt agaacacgtt gaatctaatg aaatcctagt gcgtcgatta   1980
attgaagaaa atggaaaaga atatgaaggc gaacttgatc gctatccatt agcgaagttt   2040
aaacgctcta actctggtac atgttataac caacgtccaa ttgttctat ggcgacgtt    2100 gtagaataca atgaaattct agctgacggt ccatcaatgg agcttggtga atggcatta    2160 ggccgcaacg ttgtagttgg tttcatgact tgggacggct ataactatga agatgctgtc   2220
atcatgagtg aacgtttagt caaagatgac gtttacacat ctattcatat tgaagaatat   2280
gaatcagaag cacgtgatac gaaattagga cctgaggaaa tcacacgtga tattcctaac   2340
gtctctgaaa gtgcacttaa aaacttagac gatcgcggta ttgtttatgt aggtgcagaa   2400
gttaaagatg gcgatatttt agtaggtaaa gtaacgccta aaggtgtcac agagctaaca   2460
gctgaagaac gtctattaca tgcaatcttt ggtgaaaaag cacgtgaagt gcgtgacact   2520
tcattgcgtg taccacatgg tgctggcggt attgtgctag atgttaaagt cttcaaccgt   2580
gaagaaggag atgacacact ttctccaggt gttaaccaat tagtacgcgt atatattgtg   2640
cagaaacgta aaatcacgt tggggacaaa atgtgtggtc gtcatggtaa caaaggtgtc   2700
atttctaaga ttgttccaga agaggacatg ccttatttac cagatggacg tccaattgat   2760
```

```
attatgttaa acccacttgg tgtgccatca cgtatgaaca ttggacaagt tctagagttg    2820
catttaggta tggctgctaa aaacttaggt attcatgttg cgtcaccagt atttgatggt    2880
gcgaacgatg aagatgtatg gtcaacaatt gaagaagctg gtatggcacg tgacggtaaa    2940
accgtattat atgatggccg tacaggtgag ccattcgaca accgtatctc agttggagtt    3000
atgtacatgc ttaaacttgc acatatggtt gatgacaaat acatgctcg ttcaacaggt    3060 ccatactcat tagttacaca acaaccactt ggtggtaaag cacaatttgg tggacaacgt    3120
ttcggtgaga tggaagtatg ggcacttgaa gcttatggtg ctgcctatac attgcaagaa    3180
atccttactt ataaatctga tgatacggta ggccgtgtta aaacatacga agctatcgtt    3240
aaaggtgaaa acatttctag accaagtgtt cctgaatcat tccgtgtatt gatgaaagaa    3300
cttcaaagtt taggtttaga tgtgaaagtg atggatgagc acgataacga aatcgaaatg    3360
gcagatgttg aagatgaaga tacaacagag cgcaaagtag atttgcaaca aaaagatgcg    3420
ccacaatctc aacaagaaga aactgctgat tagtcaatat attagatata aggaatggtg    3480
ttaggaacaa gtgctacgga tgtttaaaca taatgtgttt tgagttgcat ccatcctaac    3540
ctttccttaa tttcaataga tgtaaatcaa tcaaatggca cagctaatct aaattgaagg    3600
aggtaggctc cttgattgat gtaaataatt tccattatat gaaaatcggt ttagcctcac    3660
ctgaaaaaat tcgttcatgg tcatatggtg aagtgaaaaa accagaaaca attaattatc    3720
gtacgttaaa accagaaaaa gatggcttat tctgtgagag aatattcggc ccaactaaag    3780
attgggaatg tagttgtggt aaatacaaac gtgtgcgtta taaaggcatg gtttgtgata    3840
gatgtggtgt tgtaa                                                     3855

<210> SEQ ID NO 5
<211> LENGTH: 3698
<212> TYPE: DNA
<213> ORGANISM: Staphylococcus caprae

<400> SEQUENCE: 5
atgaaactta atagaaattc aaactaaatc ttacgattgg ttccttaaag aaggtttatt      60
agaaatgttt agagacattt ctccaattga agatttcaca ggtaacctat ctttagaatt     120
tgtagattat agattaggtg atccgaaata cgatttagaa gaatctaaaa accgtgacgc     180
tacttatgct gcacctcttc gtgtgaaagt acgtctcatt attaaagaaa caggcgaagt     240
gaaggaacaa gaagtcttca tgggtgattt cccattaatg actgacacag gtacattcgt     300
tatcaatggt gctgaacgtg ttatcgtttc tcaattagta cgttcaccat ccgtttattt     360
caacgagaaa attgataaaa atggacgcga aaactacgat gcaactatca ttcctaaccg     420
tggtgcttgg ttagaatatg aaacagatgc gaaagatgta gtatacgttc gtatcgatag     480
aactcgtaaa ttaccattga cagtattatt acgtgcacta gatttctcaa ctgatcaaga     540
aattgttgat ttactaggtg agagtgaata tttacgtaat acattagaaa agatggtac      600 tgaaaatact gaacaagcat tattagaaat ttatgaacgt ttacgtcctg gcgaaccacc     660
aacagttgaa aatgctaaaa gcttattata ctcacgcttc ttcgacccta acgttatga      720 tttagcaagt gttggtcgtt acaaagctaa caaaaagtta catttaaaac accgtttatt     780
taatcaaaaa ttagcagaac ctattgttaa tagtgaaaca ggtgagattg tagctgaaga     840
aggtactgta ttagatcgtc gtaaaattga cgaaatcatg gacgttttag aaacaaacgc     900
taacagtgaa gttttcgaat tagaaggtag cgttattgac gaacctgttg aaattcaatc     960
aattaaagtc tatgtaccta tgatgaaga aggtcgcaca actactgtaa ttggtaatgc    1020
```

```
attaccagat tcagaagtta aatgtattac tccagctgat atcattgcgt caatgagtta     1080
tttcttcaac ttattaaatg gtattggtta tacagatgat atcgaccact taggtaaccg     1140
tcgtttacgt tcagttggtg aacttttaca gaaccaattc cgtatcggtt tatcaagaat     1200
ggaacgtgtt gttcgtgaaa gaatgtctat tcaagacact gattcaatca caccacaaca     1260
attaatcaac attcgtccgg ttattgcgtc tattaaagaa ttcttcggaa gttcacaatt     1320
atcgcaattc atggaccaag ctaacccatt agctgagttg actcataaac gtcgtctatc     1380
agcattagga cctggtggtt taacgcgtga acgtgcccaa atggaagtgc gtgacgttca     1440
ctattctcac tatggccgta tgtgtccaat cgaaacacct gagggaccaa acattggttt     1500
aatcaactca ttatcaagtt atgcacgagt aaatgaattt ggttttattg aaacaccttta     1560 tcgtaaagta gatttagata cgaattctat cactgaccaa attgattact taactgctga     1620
tgaagaagat agttatgttg ttgcccaagc gaactctcgt ttagacgaaa atggtcgttt     1680
cttagatgac gaagttgttt gtcgtttccg tggtaataac acagttatgg ctaaagagaa     1740
aatggactac atggatgtat ctcctaaaca gtagtatct gcagcgacag cttgtattcc      1800
attcttagaa aatgatgact ctaaccgtgc attaatgggt gcgaacatgc aacgtcaagc     1860
agtaccattg atgaatccag aagcgccatt tgttggtaca ggtatggaac atgtagccgc     1920
acgtgattca ggtgcagcga ttactgctaa acatagagga cgcgttgaac acgttgaatc     1980
taacgaagta ttagtacgtc gtttagtaga agaaaacggc actgaacatg aaggtgaatt     2040
agatcgttac ccattagcta aattcaaacg ttcaaactct ggtacatgtt ataaccaacg     2100
tccaattgtt tctgttggtg atgtagtaga atacaatgaa attttagctg acggtccttc     2160
aatggaatta aggttgaaat ggcatagga cgtaacgttg ttagttggtt tcatgacttg      2220
ggacggttat aactacgagg atgctgttat catgagtgaa cgtttagtta aagatgacgt     2280
ttatacttct attcacattg aagaatatga atctgaagct cgtgatacta agttaggacc     2340
tgaagaaatt actcgtgaca ttcctaacgt atctgaaagt gcacttaaaa acttagacga     2400
tcgcggtatc gtttatgttg gtgctgaagt taaagacggt gacatcttag taggtaaagt     2460
aacgcctaaa ggtgtaactg aattaacagc tgaagaaaga ttattacatg ctatcttcgg     2520
tgaaaaggct cgtgaagtcc gcgatacatc attacgtgta ccacatggtg caggcggtat     2580
cgttctagat gttaaagtat tcaatcgtga agaaggcgat gatacgttat ctccaggtgt     2640
aaaccaattg gtacgtgttt atatcgttca aaaacgtaaa attcatgtag gggacaaaat     2700
gtgtggtcgt cacggtaaca aaggtgttat ctctaaaatt gttcctgaag aagatatgcc     2760
atacttacca gatggtcgtc caatcgacat catgttaaac ccacttggtg taccatcacg     2820
tatgaacatc ggacaagtac ttgagttgca tttaggtatg gctgctaaga acttaggcat     2880
ccatgtagca tctccagtat tcgatggtgc aaacgatgat gatgtatggt caacaattga     2940
agaagcaggt atggctcgtg atggtaaaac tgtattatac gatggacgta caggtgaacc     3000
attcgataac cgtatttctg taggtgtcat gtacatgctt aaacttgctc acatggttga     3060
cgataaatta cacgcacgtt caactggacc atactcactt gttacacaac aaccacttgg     3120
tggtaaagca caattcggtg gtcaacgctt cggtgagatg gaggtatggg cacttgaagc     3180
atatggtgct gcatacacat tacaagaaat cttaacttat aaatctgacg atacagtagg     3240
tcgtgttaaa acttacgaat ctatcgttaa aggtgaaaat atctctagac caagtgttcc     3300
agaatcattc agagtattga tgaaagaatt acaaagttta ggattagatg ttaaagtgat     3360
```

-continued

```
ggacgagcaa gacaacgaaa ttgaaatggc ggacgttgat gatgaagatg caactgaacg    3420
caaagtagat ttacaacaaa aaaatgctcc cgaatcacaa aaagaaacaa ctgattaata    3480
agcacttaag ataaatgaat cctaaagagg ttatgagatg gttgccattt caacctcttt    3540
aaggtattcg atttcaatga atgtaaatca atcaaatagc acagctaatc taaattgaag    3600
gaggtaggct ccttgattga tgtaaataat ttccattata tgaaatagg attagcttca    3660 cctgaaaaaa ttcgttcttg gtcttatggt gaagttaa                           3698
```

<210> SEQ ID NO 6
<211> LENGTH: 3851
<212> TYPE: DNA
<213> ORGANISM: Staphylococcus intermedius

<400> SEQUENCE: 6

```
atgtaaactt aatagaaatt cmaactaaat cgtatgattg gttcttaaaa gaaggtttat      60
tagaaatgtt ccgtgatatt tctcctattg aagacttcac gggtaatctt tcattagaat     120
ttgttgatta tagattaggt gaaccaaagt atgatttaga agaatcaaaa accgtgatg      180 caacatacgc ggcaccatta cgtgtgaaag ttcgtttaat cattaaagaa acaggcgaag     240
tgaaagatca agaagtattt atgggtgatt cccattaat gacagaaaca ggtacttttg      300
tgattaacgg ggcagaacgt gttatcgtat cacaattagt ccgttcacca tctgtatact     360
tcaatgaaaa attagataaa aacggatgcg tgaattatga tgcgacagtc attcctaacc     420
gtggtgcttg gttggaatat gaaacagatg cgaaagatgt cgtttatgtg cgtatcgata     480
gaacgagaaa gttaccatta acagtattat tacgtgcgtt aggttattca acagaccaag     540
aaattattga attaattggg gataatgaat atttacgtaa tacattagaa aaagatagca     600
cagaaaatac agagcaagca ttacttgaaa tttatgaacg tttacgtcca ggtgaaccac     660
ctactgtaga aaacgcaaaa agcttattat actcacgttt cttttgaccct aaacgttatg    720 atttagcaag cgttggacgt tataaagcaa acaaaaagtt acatttaaaa caccgcctat    780
tcaatcaaaa attagctgaa ccgatcgtta atactgaaac aggcgaaatt gttgctgaag    840
aaggcactgt tttagatcgt cgtaaattag atgaaattat ggacgttctt gaaacaaatg    900
cgaatgcaca agtttatgaa cattccaaac ggatcattga tgagccagta gaaattcaat    960
caattaaagt atatgtaccg aatgatgatg aagaacgtac aacaacagtt attggtaatg   1020
cattcccaga ttcagaagtg aaatgtatta caccggctga tattgtggca tctatgtcat   1080
acttcttcaa cctattacat ggtattggtt acacagacga tattgaccac cttggtaacc   1140
gccgtctacg ttcagttggt gagttgttac aaaaccaatt ccgtatcggt ttatcaagaa   1200
tggaacgtgt ggtacgtgaa agaatgtcta ttcaagatac agactctatc acaccgcaac   1260
aattaattaa tattcgtcca gtgattgcat caattaaaga gttctttggt agctcgcaat   1320
tatctcaatt catggaccaa gcgaacccac ttgctgagtt gactcacaaa cgtcgtctat   1380
cagcattagg acctggtggt ttaacgcgtg aacgtgctca aatggaagtg cgtgacgtac   1440
actactctca ctatggtcgt atgtgtccaa tcgaaacacc tgagggacca aacattggtt   1500
tgatcaactc attatctagt tatgcacgtg tgaacgaatt tggttttatc gaaacaccat   1560
atcgtaaagt tgatattgaa acaaatacga ttactgacca aatcgactac ttaactgctg   1620
atgaagaaga tagttatgtt gtcgcacaag cgaactcacg tcttgatgaa acggtcgct    1680 ttattgatga tgagattgta tgtcgtttcc gtggtaacaa cacaacgatg gcgaaagaaa   1740
aaatggacta catggacgta tcgccgaaac aagttgtatc agctgcgaca gcgtgtatcc   1800
```

```
cattcttaga aaacgatgac tctaaccgtg cgttaatggg tgcgaacatg cagcgtcaag    1860
cggtaccgtt gttaaaccct gaatctccat ttgtaggtac aggtatggaa cacgttgctg    1920
cacgtgactc aggtgctgct gtcatttcta aatatcgcgg tcgtgttgaa catgtccaat    1980
ctagcgagat tttagtccgt cgtttagttg aagaaacgg tcaagaagta gatggtacgt     2040
tagatcgtta tccattagcg aaatttaaac gttcgaactc aggtacatgt tataaccaac    2100
gtccaatcat cgcaaaaggt gacattgtgg aaaaggcga atccttgct gatggtcctt      2160
caatggaact tggtgaaatg gcattaggtc agaaacgtag tagttggttc atgacttggg    2220
acggttataa ctatgaggat gccgttatca tgagtgaacg tttggttaaa gatgatgtgt    2280
acacgtctat tcatattgaa gaatacgaat cagaagcgcg tgacacaaaa cttggacctg    2340
aagaaatcac acgtgatatt cctaacgtat ctgaaaatgc actgaaaaac ttagatgatc    2400
gcggtatcgt ttatgtaggt gcggaagtta agacggcga catcttagtg ggtaaagtaa     2460
cgccaaaagg tgtaacagaa ttaactgcag aagaacgttt attacatgca atctttggtg    2520
aaaaagcacg tgaagtacgt gatacatcat tacgtgtacc tcacggcgcg ggcggtattg    2580
tacttgatgt taaagtgttc aatcgtgaag aaggcgatga ttcactttca ccaggtgtga    2640
accaactcgt acgtgtttac attgttcaaa acgtaaaat tcatgtaggg gacaaaatgt     2700
gtggtcgtca cggtaacaaa ggtgtcatct ctaaaattgt tcctgaagaa gacatgccgt    2760
acttaccaga cggtcgtcca atcgacatca tgttgaaccc actcggtgta ccatctcgta    2820
tgaacatcgg acaagttta gagctccact taggtatggc agctaaaaac ttaggtatcc     2880
acgttgcatc accagtattc gatggtgcga acgatgatga cgtatggtct acaattgaag    2940
aagcaggtat ggcacgtgat ggtaaaactg tcctttacga tggacgtaca ggtgaaccat    3000
tcgacaaccg tatctctgta ggtgtcatgt acatgctgaa acttgcacac atggttgatg    3060
acaagcttca cgcacgttct acaggacctt actcacttgt tacacaacaa ccgcttggtg    3120
gtaaagcaca gtttggtgga caaagatttg gtgagatgga ggtatgggca cttgaagcat    3180
acggtgcagc atacacatta caagaaatcc tcacatacaa atcagatgac acagtaggtc    3240
gtgtgaaaac ttacgaagct atcgttaaag gtgaaaacat ctcaagacca gtgttcctg    3300
aatcattccg cgtattgatg aaagaattac aaagtttagg tcttgacgtt aaagtgatgg    3360
acgaacaaga taacgaaatt gaaatgcgtg acttagacga tgatgatatt ccagatcgca    3420
aagtcaacat tcaaccatca actgttcctg aatcacaaaa agaatttaac gaataatgat    3480
gaattgtaga taagattaaa cggaatagaa acacttggtt aagcttgagt ttgtgttcaa    3540
atgtgacagt tgaaatacaa cagatgtcat gtacgattaa tctattcgga aatgtgatcg    3600
gaatccaacg agagggcttg ggtttcgatg catatccgat actgcaacat ttttaagata    3660
aattgtaaat caatcaacta gcacagttaa tttaaactaa aggaggtagg ctccttgatt    3720
gatgtaaata aattccatta catgaaaata ggactcgctt cacctgaaaa aattcgttct    3780
tggtcatatg gtgaggtcaa aaagccagaa acaattaact accgtacgtt aaaaccagaa    3840
aaagatggta a                                                         3851
```

<210> SEQ ID NO 7
<211> LENGTH: 20
<212> TYPE: DNA
<213> ORGANISM: Artificial Sequence
<220> FEATURE:
<223> OTHER INFORMATION: primer
<220> FEATURE:

```
<221> NAME/KEY: misc_feature
<222> LOCATION: (15)..(15)
<223> OTHER INFORMATION: n=inosine, A, T, C or G

<400> SEQUENCE: 7
aaccaattcc gtatnggttt                                                    20

<210> SEQ ID NO 8
<211> LENGTH: 19
<212> TYPE: DNA
<213> ORGANISM: Artificial Sequence
<220> FEATURE:
<223> OTHER INFORMATION: primer

<400> SEQUENCE: 8
ccgtcccaag tcatgaaac                                                     19

<210> SEQ ID NO 9
<211> LENGTH: 17
<212> TYPE: DNA
<213> ORGANISM: Artificial Sequence
<220> FEATURE:
<223> OTHER INFORMATION: primer

<400> SEQUENCE: 9
caattcatgg accaagc                                                       17

<210> SEQ ID NO 10
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (3)..(3)
<223> OTHER INFORMATION: n=inosine, A, T, C or G
<220> FEATURE:
<221> NAME/KEY: misc_feature
<222> LOCATION: (6)..(6)
<223> OTHER INFORMATION: n=inosine, A, T, C or G
<220> FEATURE:
<221> NAME/KEY: misc_feature
<222> LOCATION: (9)..(9)
<223> OTHER INFORMATION: n=inosine, A, T, C or G

<400> SEQUENCE: 10
gcnacntgnt ccatacctgt                                                    20

<210> SEQ ID NO 11
<211> LENGTH: 518
<212> TYPE: DNA
<213> ORGANISM: Staphylococcus xylosus

<400> SEQUENCE: 11
ttcagggttc atcaatggca ctgcttgacg ttgcatgttt gcacccatca atgcacggtt         60
agagtcatca ttttctaaga aggaataca tgctgtcgca gcagaaacaa cttgttttgg        120
tgaaacgtcc atgtaatcca ttttttcttt agccataact gtgttattac cacggaaacg       180
acaaacaact tcatcatcta agaaacgacc attttcatct aatttagagt tggcttgtgc       240
taccacataa ctatcctctt catcagctgt aagtaatcg atttgctcag taatgctgtt       300
tgtttcaagg tctactttac gataaggtgt ttcaatgaaa ccaaattcat tcacacgtgc      360
ataactagac aatgagttga taagtccaat gtttggacct tcaggcgttt cgattggaca       420
catacggcca tagtcagaat agtgaacgtc acgtacttcc atttgagcac gttcacgtgt       480
```

```
taaaccacca ggtcctagag cagataaacg acgtttgt                              518

<210> SEQ ID NO 12
<211> LENGTH: 507
<212> TYPE: DNA
<213> ORGANISM: Staphylococcus warneri

<400> SEQUENCE: 12
ttcaggattc atcaatggta ctgcttgacg ttgcatgttc gcacccatta atgcacggtt     60
agagtcatcg ttttctaaga atggaataca agctgtagcg gctgaaacaa cctgcttagg    120
tgaaacgtcc atgtaatcca ttttttcttt agccattact gtgttattac cacggaaacg    180
acaaactact tcgtcatcta tgaaacgtcc gttttcatct aaacgtgaat tcgcttgggc    240
aacaacataa ctatcttctt cgtcagcagt taaataatca atttggtctg taatcgcatt    300
agtgtctaaa tccactttac gatatggtgt ttcaatgaaa ccaaattcgt ttacacgtgc    360
ataactagat aatgagttga ttaatccaat gtttggaccc tctggcgttt caattggaca    420
catacgacca tagtgagaat agtgtacgtc acgtacctcc atttgtgcac gttcacgtgt    480
taaaccacca ggtcctaaag cagataa                                        507

<210> SEQ ID NO 13
<211> LENGTH: 518
<212> TYPE: DNA
<213> ORGANISM: Staphylococcus simulans

<400> SEQUENCE: 13
ttcagggttc atcaatggta ctgcttgacg ttgcatgttc gcacccatta acgcacggtt     60
agagtcatcg ttttctaaga atgggataca tgctgtcgct gcagatacaa cttgtttagg    120
agaaacgtcc atatagtcca ttttctctct atccatagtt gtgttgttac cacggaaacg    180
acaaacgatt tcttcgtcta agaaacgacc ttcgtcatct aaacgtgagt tcgcttgcgc    240
aacaacatag ctgtcttctt cgtctgcagt aaggtaatcg atttgatctg ttaccgcatt    300
tttctcatgg tcaactttac gatatggtgt ttcaatgaaa ccaaattcat taacacgcgc    360
ataacttgat aatgagttga ttaaaccgat gttcggaccc tctggtgtct cgattggaca    420
catacggcca tagtgagagt aatgcacgtc acgtacttcc atttgtgcac gttcacgtgt    480
taaaccacca ggtccaagtg cagatagacg acgtttat                            518

<210> SEQ ID NO 14
<211> LENGTH: 507
<212> TYPE: DNA
<213> ORGANISM: Staphylococcus sciuri

<400> SEQUENCE: 14
ttctgggttc attaaaggta ccgcttgacg ttgcatgttt gcacccataa gcgcacggtt     60
agagtcatcg ttttctaaga atggaataca tgctgtcgct gcagaaacaa cttgtttagg    120
agatacatcc atgtagtcca tgcgttcttt aggtttagta gtgttgtccc cacggaaacg    180
acaaagaact tcatcatcaa cgaatttacc tgtttcatca agtacagagt ttgcttgtgc    240
aactacatag ctgtcttctt cgtcagctgt taagtagtcg attctgtcag taacttggtt    300
tgtctcgatg tttaccttac gataaggtgt ttcaatgaaa ccaaattcat taactcttgc    360
ataacttgat aatgagttga ttaaaccaat gtttggtccc tcaggcgttt caattggaca    420
catacgacca tagtgagagt agtgaacgtc acgtacttcc ataccagcac gctcacgagt    480
```

-continued

```
taaaccaccc ggtcctaatg ctgatag                                        507
```

<210> SEQ ID NO 15
<211> LENGTH: 518
<212> TYPE: DNA
<213> ORGANISM: Staphylococcus schleiferi

<400> SEQUENCE: 15

```
ttctgggttt aacaatggta ctgcttgacg ttgcatgttc gcacccatca atgcacggtt     60
agagtcatcg ttttctaaaa acggaataca tgctgtcgca gctgaaacaa cttgtttagg    120
cgatacgtcc atgtagtcca tttttcttt agccatagtt gtgttgttac cacggaaacg    180
acaaacgatt tcgtcatcga taaaacgtcc gttttcatca agtcttgagt tcgcttgggc    240
aacaacataa ctgtcttctt catcagcagt aaggtaatca atacggtctg taattgtgtt    300
tgtttcaagg tctactttc tgtatggagt ttcaatgaaa ccaaattcat tcacacgtgc     360
ataacttgaa agtgagttga tcaaaccaat gtttggaccc tctggtgtct cgattggaca    420
catacggcca tagtgagaat agtgtacgtc acgaacttcc atttgtgcac gttcacgtgt    480
taaaccacca ggccctaaag ctgataaacg acgtttgt                            518
```

<210> SEQ ID NO 16
<211> LENGTH: 518
<212> TYPE: DNA
<213> ORGANISM: Staphylococcus saprophyticus

<400> SEQUENCE: 16

```
ttctggattc atcaatggca ctgcttgacg ttgcatgttc gcacccatca atgcacggtt     60
agagtcatcg ttttctaaga aaggaataca tgctgtcgct gcagaaacaa cttgtttagg    120
tgagacatcc atataatcca tttttcttt ggccataact gtattattac cacggaaacg    180
acaaacaact tcgtctgcta tgaaacggcc attttcgtct aatgttgagt ttgcttgtgc    240
tacaacatag ctatcttctt catcagctgt taaatagtca atttgatccg tgattgaatt    300
cgtttcaaga tccactttac ggtaaggtgt ttcaataaag ccgaattcat ttacacgcgc    360
ataactagat aacgagttaa taagtccgat gtttggaccc tctggcgttt caattggaca    420
catacggcca tagtgagaat agtgaacgtc acgtacttcc atttgagcac gttcacgcgt    480
taaaccacca ggtcctagag ctgataaacg acgtttat                            518
```

<210> SEQ ID NO 17
<211> LENGTH: 518
<212> TYPE: DNA
<213> ORGANISM: Staphylococcus saccharolyticus

<400> SEQUENCE: 17

```
ttctgggttc attaatggta ctgcttgacg ttgcatgttt gcacccatta atgctcggtt     60
tgagtcatcg ttttctaaga atgggataca tgcagtagct gctgaaacta cttgtttagg    120
tgatacgtcc atatagtcca tttttcttt agccatcact gtgttattgc cacgaaaacg    180
acaaacaact tcatcatcta agaagcaccc attttcatca agacgtgagt ttgcttgtgc    240
aacaacataa ctatcttctt catcagcagt taagtagtca atttggtcag tgattgaatt    300
agtatctaaa tcaactttac gataaggtgt ttcaataaaa ccaaattcat ttactcttgc    360
ataactagat aatgagttaa ttaatccaat gtttgggccc tcaggtgttt caatagggca    420
catacgaccg tagtgagaat aatgcacgtc acgtacttcc atttgagcgc gttcacgagt    480
taaaccacca ggtcctagag ctgataaacg acgtttat                            518
```

<210> SEQ ID NO 18
<211> LENGTH: 508
<212> TYPE: DNA
<213> ORGANISM: Staphylococcus pulveris

<400> SEQUENCE: 18

| | | | | | |
|---|---|---|---|---|---|
| ttcaggattc | attaaaggca | ctgcttgacg | ttgcatgttt | gcacccataa | gcgcacggtt | 60 |
| agagtcatcg | tttttctaaga | aaggaataca | tgctgtcgca | gcagaaacaa | cctgtttagg | 120 |
| tgatacatcc | atgtaatcca | tacgttcttt | aggtttcgta | gtattatccc | cacggaaacg | 180 |
| acaaagtact | tcatcatcaa | cgaatttacc | tgtttcatca | agtactgagt | ttgcttgcgc | 240 |
| tacaacatag | ctgtcttctt | cgtcagctgt | taaatagtca | attctgtcag | taacttggtt | 300 |
| tgtttcgata | ttaaccttac | gataaggcgt | ttcaataaaa | ccaaattcat | taactctcgc | 360 |
| ataacttgat | aaagagttaa | ttaaaccgat | gtttggtccc | tcaggtgttt | caattggaca | 420 |
| catacgacca | tagtgagaat | agtgaacgtc | acgtacttcc | ataccagcac | gttcacgaag | 480 |
| ttaaaccgcc | gggtcctaat | gctgatag | | | | 508 |

<210> SEQ ID NO 19
<211> LENGTH: 518
<212> TYPE: DNA
<213> ORGANISM: Staphylococcus muscae

<400> SEQUENCE: 19

| | | | | | |
|---|---|---|---|---|---|
| ttcaggattc | aacaatggca | ccgcttgacg | ttgcatgttc | gcacccatta | aggcacggtt | 60 |
| agagtcatcg | tttttctaaga | atggaataca | tgctgtcgca | gcagaaacaa | cttgcttcgg | 120 |
| cgatacgtcc | atgtagtcca | tttttctcttt | tgccattgtt | gtgttgttac | cacggaaacg | 180 |
| acatacaatc | tcatcatcaa | taaagcgacc | attttcatct | aaacgtgagt | tcgcttgtgc | 240 |
| aaccacataa | ctatcttctt | catcagcagt | taaatagtcg | atttgatcag | tgattgtgtt | 300 |
| cgtctcgata | tcaactttac | gatatggtgt | ttcaatgaaa | ccaaattcat | taacacgtgc | 360 |
| ataactagat | agtgagttga | tcaaaccaat | gttcagtccc | tctggtgtct | caatcggaca | 420 |
| catacgacca | tagtgagagt | agtgaacgtc | acgcacttcc | atttgtgcac | gttcacgtgt | 480 |
| caaaccacca | ggccctaatg | ctgaaagacg | acgcttat | | | 518 |

<210> SEQ ID NO 20
<211> LENGTH: 518
<212> TYPE: DNA
<213> ORGANISM: Staphylococcus lugdunensis

<400> SEQUENCE: 20

| | | | | | |
|---|---|---|---|---|---|
| ttcagggttc | atcaacggaa | ctgcttgacg | ttgcatgttt | gcacccatca | atgcacggtt | 60 |
| agagtcatcg | ttctctaaga | atggaataca | tgctgtcgca | gctgaaacaa | cttgtttagg | 120 |
| agatacatcc | atgtagtcca | ttttttctttt | agccataaca | gtattattac | cgcggaaacg | 180 |
| gcatactact | tcatcatcta | agaaacgacc | attttcatca | aggcgagagt | tcgcttgtgc | 240 |
| aacgacataa | ctgtcttctt | catcagcagt | taagtagtca | atttgatctg | tgattgcatt | 300 |
| tgtatcaata | tctactttac | gataaggcgt | ttcaataaag | ccaaactcgt | tgacacgcgc | 360 |
| ataactagat | aatgagttaa | tcaaaccaat | gtttggaccc | tctggtgttt | caatcggaca | 420 |
| catacggcca | tagtgagaat | aatgcacgtc | acgaacttcc | atttgtgcac | gttcacgtgt | 480 |
| taaaccacca | ggtcctaacg | cagataaacg | acgtttgt | | | 518 |

<210> SEQ ID NO 21
<211> LENGTH: 507
<212> TYPE: DNA
<213> ORGANISM: Staphylococcus lentus

<400> SEQUENCE: 21

| | | | | | |
|---|---|---|---|---|---|
| ttcagggttc | attaaaggta | ctgcttgacg | ttgcatgttc | gcacccatta | aggcacggtt | 60 |
| agagtcatcg | ttttcaagga | aaggaataca | tgctgatggt | gcagaaacaa | cttgtttagg | 120 |
| agatacatcc | atgtaatcca | tacgttcttt | aggtttagta | gtgttgtcac | cacggaaacg | 180 |
| acaaagaact | tcatcgtcga | cgaatctacc | agtttcatct | aatactgagt | ttgcttgtgc | 240 |
| aacaacataa | ctatcttctt | catcagcagt | tagataatca | attctgtctg | ttacttggtt | 300 |
| agtttcgata | ttaactttac | gatatggtgt | ttcaataaag | ccaaactcgt | taactctagc | 360 |
| ataacttgaa | agtgagttga | ttaaaccaat | gtttggtccc | tctggtgtct | caatcggaca | 420 |
| catacgacca | tagtgagaat | agtgaacgtc | acgtacttcc | ataccagcac | gttcacgagt | 480 |
| taaaccgccg | ggtccaagcg | ctgatag | | | | 507 |

<210> SEQ ID NO 22
<211> LENGTH: 505
<212> TYPE: DNA
<213> ORGANISM: Staphylococcus kloosii

<400> SEQUENCE: 22

| | | | | | |
|---|---|---|---|---|---|
| ttcacggttc | atcaatggta | ccgcttgacg | ttgcatgttc | gcacccatta | aggcacggtt | 60 |
| agagtcatcg | ttttctaaga | aaggaataca | tgctgtcgca | gccgaaacaa | cttgttttgg | 120 |
| tgatacgtcc | atgtagtcca | ttttttcttt | cgccataact | gtgttgttac | cacggaaacg | 180 |
| acaaactact | tcatcatcta | agaaacgacc | attttcatct | aatttagagt | tagcttgcgc | 240 |
| taccacatag | ctatcttctt | catcagctgt | taaatagtca | atttgatctg | tgattgaatt | 300 |
| agtttctaaa | tcaactttac | ggtatggtgt | ttcgataaag | ccaaattcat | taacacgtgc | 360 |
| ataacttgat | aatgagttga | taagtccaat | gtttggaccc | tctggcgttt | cgattggaca | 420 |
| catacgacca | tagtgagaat | agtaacgtca | cgcacttcca | tttgagcacg | ttcacgagtt | 480 |
| aaaccaccag | gtccaagcca | gatag | | | | 505 |

<210> SEQ ID NO 23
<211> LENGTH: 518
<212> TYPE: DNA
<213> ORGANISM: Staphylococcus intermedius

<400> SEQUENCE: 23

| | | | | | |
|---|---|---|---|---|---|
| ttcagggttt | aacaacggta | ccgcttgacg | ctgcatgttc | gcacccatta | acgcacggtt | 60 |
| agagtcatcg | ttttctaaga | atgggataca | cgctgtcgca | gctgatacaa | cttgtttcgg | 120 |
| cgatacgtcc | atgtagtcca | ttttttcttt | cgccatcgtt | gtgttgttac | cacggaaacg | 180 |
| acatacaatc | tcatcatcaa | taaagcgacc | gttttcatca | agacgtgagt | tcgcttgtgc | 240 |
| gacaacataa | ctatcttctt | catcagcagt | taagtagtcg | atttggtcag | taatcgtatt | 300 |
| tgtttcaata | tcaactttac | gatatggtgt | ttcgataaaa | ccaaattcgt | tcacacgtgc | 360 |
| ataactagat | aatgagttga | tcaaaccaat | gtttggtccc | tcaggtgttt | cgattggaca | 420 |
| catacgacca | tagtgagagt | agtgtacgtc | acgcacttcc | atttgagcac | gttcacgcgt | 480 |
| taaaccacca | ggtcctaatg | ctgatagacg | acgtttgt | | | 518 |

<210> SEQ ID NO 24
<211> LENGTH: 518
<212> TYPE: DNA
<213> ORGANISM: Staphylococcus hyicus

<400> SEQUENCE: 24

| | | | | | |
|---|---|---|---|---|---|
| ctctgggttc | aataaaggca | cggcttgacg | ttgcatgttc | gcacccatta | atgcacggtt | 60 |
| cgagtcatcg | ttttctaaga | atgggataca | tgctgtcgcc | gcagaaacaa | cttgtttcgg | 120 |
| tgatacgtcc | atgtaatcca | ttttttcttt | agccattgtt | gtattgttcc | cacggaaacg | 180 |
| acaaacgatt | tcgtcgtcga | taaagcgtcc | attttcatct | aaacgtgagt | tcgcttgggc | 240 |
| aacaacataa | ctgtcttctt | catccgcagt | taagtaatca | atttgatctg | ttattgtatt | 300 |
| cgtttcaagg | tccactttac | ggtaaggcgt | tcaatgaaa | ccaaattcgt | taacacgcgc | 360 |
| ataacttgaa | agtgagttga | ttaatccaat | gtttggaccc | tctggcgttt | cgattggaca | 420 |
| catacgaccg | tagtgagagt | agtgaacgtc | acgcacttcc | atttgggcac | gttcacgcgt | 480 |
| taaaccacca | ggtcctaatg | cagataaacg | acgtttgg | | | 518 |

<210> SEQ ID NO 25
<211> LENGTH: 518
<212> TYPE: DNA
<213> ORGANISM: Staphylococcus hominis

<400> SEQUENCE: 25

| | | | | | |
|---|---|---|---|---|---|
| ttcaggattc | atcaatggta | ctgcttgacg | ttgcatgttc | gcacccatta | acgcacggtt | 60 |
| agagtcatcg | ttttcaagga | atggaataca | agctgtcgct | gctgatacta | cttgtttagg | 120 |
| agatacatcc | atgtagtcca | ttttttcttt | tgccataaca | gtgttgttac | cacggaaacg | 180 |
| acataccact | tcatcatcta | ggaaacgacc | attttcatct | aaacgagaat | tggcttgtgc | 240 |
| aactacatag | ctatcttctt | catcagcagt | taaataatca | atttgatcag | taatcgaatt | 300 |
| ggtatcaata | tctactttac | gatatggtgt | ttcgataaaa | ccaaattcat | ttacacgtgc | 360 |
| ataactagat | aatgagttaa | ttaaaccaat | gtttggtccc | tctggtgttt | caattggaca | 420 |
| catacgacca | tagtgagaat | agtgtacgtc | acgaacttcc | atttgtgcac | gttcacgtgt | 480 |
| taaaccacca | ggtcctaaag | cagaaagacg | acgtttag | | | 518 |

<210> SEQ ID NO 26
<211> LENGTH: 507
<212> TYPE: DNA
<213> ORGANISM: Staphylococcus haemolyticus

<400> SEQUENCE: 26

| | | | | | |
|---|---|---|---|---|---|
| ttctgtgttc | atcaatggta | ctgcttgacg | ttgcatgttt | gcacccatta | atgcacggtt | 60 |
| agagtcatca | ttttcaagga | aaggaataca | tgctgtcgca | gctgaaacta | cttgtttagg | 120 |
| agatacgtcc | atgtagtcca | ttttctcttt | agccataact | gtgttattac | cacggaaacg | 180 |
| acatacgact | tcatcatcta | agaaacgacc | attttcatct | aagcgagagt | tcgcttgggc | 240 |
| aactacatag | ctatcttctt | catcagcagt | taagtagtcg | atttgatctg | taatagagtt | 300 |
| agtgtctaag | tctactttac | gatatggtgt | ttcaatgaaa | ccaaattcat | tcacacgtgc | 360 |
| ataacttgat | aatgagttaa | tcaaaccaat | gtttggtccc | tctggagtct | cgatcggaca | 420 |
| catacgacca | tagtgagagt | agtgaacgtc | acgtacttcc | atttgagcac | gttcacgtgt | 480 |
| taaaccacca | ggtcctaatg | cagaaag | | | | 507 |

<210> SEQ ID NO 27

<211> LENGTH: 507
<212> TYPE: DNA
<213> ORGANISM: Staphylococcus gallinarum

<400> SEQUENCE: 27

| | | | | | |
|---|---|---|---|---|---|
| ttcaggattc | atcaaaggta | cagcttgacg | ttgcatgttc | gcacccatca | atgcacggtt | 60 |
| agagtcatcg | ttttctaaga | aaggaataca | tgctgtcgca | gcagatacaa | cctgtttagg | 120 |
| tgatacatcc | atgtagtcca | ttttttcttt | tgccattaca | gtgttgttac | cacgaaaacg | 180 |
| acaaacgact | tcatcttcta | cgaaacgacc | attttcatct | aatacagagt | ttgcttgtgc | 240 |
| tactacataa | ctgtcttctt | catcagctgt | taagtagtca | atttgatctg | taatagattg | 300 |
| tgtttcaata | tcaactttac | gatatggtgt | ttcaatgaaa | ccaaattcat | ttacacgcgc | 360 |
| ataacttgat | aatgagttga | taagtccgat | gtttggaccc | tcaggtgttt | cgattggaca | 420 |
| catacggcca | tagtgagaat | agtgaacgtc | acgtacttcc | atttgagcac | gttcacgagt | 480 |
| taaaccacca | ggtcctaatg | ctgatag | | | | 507 |

<210> SEQ ID NO 28
<211> LENGTH: 518
<212> TYPE: DNA
<213> ORGANISM: Staphylococcus felis

<400> SEQUENCE: 28

| | | | | | |
|---|---|---|---|---|---|
| ttcgggattc | attaaaggta | cagcttgacg | ttgcatgttc | gcacccatta | atgcacggtt | 60 |
| agagtcatcg | ttttctaaga | atgggataca | tgccgtcgca | gcagaaacga | cttgcttagg | 120 |
| cgatacgtcc | atgtagtcca | ttttttcttt | ggccatcgtt | gtattgtttc | cgcggaaacg | 180 |
| acatacaatc | tcgtcatcca | agaaacggcc | ttcttcgtct | aatcgtgcgt | ttgcttgtgc | 240 |
| aacaacataa | ctatcttctt | catcagctgt | aagatagtca | atttggtctg | taattttatt | 300 |
| tgtctcaaga | tcgactttac | gatatggtgt | ttcgataaat | ccaaattcgt | taacacgtgc | 360 |
| ataacttgat | aatgagttga | ttaatccgat | gttcggcccc | tctggcgttt | caataggaca | 420 |
| catgcgacca | tagtgagagt | agtgaacgtc | acgcacttcc | atctgtgcac | gttctctcgt | 480 |
| taaaccacca | ggtcctaatg | cggatagacg | acgtttat | | | 518 |

<210> SEQ ID NO 29
<211> LENGTH: 507
<212> TYPE: DNA
<213> ORGANISM: Staphylococcus equorum

<400> SEQUENCE: 29

| | | | | | |
|---|---|---|---|---|---|
| ttcaggattc | atcaatggca | ctgcttgacg | ttgcatgttt | gcacccatca | atgcacggtt | 60 |
| agagtcatcg | ttttctaaga | aaggaataca | tgctgtcgca | gcagaaacaa | cttgtttagg | 120 |
| tgaaacatcc | atgtagtcca | ttttttcttt | agccataact | gtgttattac | cacggaaacg | 180 |
| acaaacaact | tcgtcttcta | cgaaacgacc | attttcatct | aatacagagt | ttgcttgagc | 240 |
| tactacatag | ctgtcttctt | cgtcagctgt | taagtagtca | atttggtctg | tgattgaatg | 300 |
| tgtttcaaga | tctactttac | ggtaaggtgt | ttcaatgaaa | ccaaattcat | tcacacgcgc | 360 |
| ataactagat | agtgagttga | taagtccgat | attcggaccc | tctggtgttt | cgattggaca | 420 |
| catacgacca | tagtgagaat | agtgaacgtc | acgtacttcc | atttgagcac | gttcacgtgt | 480 |
| taaaccgccg | ggtcctaatg | ctgataa | | | | 507 |

<210> SEQ ID NO 30
<211> LENGTH: 518

<212> TYPE: DNA
<213> ORGANISM: Staphylococcus epidermidis

<400> SEQUENCE: 30

| | | | | | |
|---|---|---|---|---|---|
| ttcaggattc | attaaaggca | ccgcttgacg | ttgcatgttt | gctcccatta | acgcacggtt | 60 |
| agagtcgtca | ttttctaaga | atggaataca | tgctgttgct | gctgaaacaa | cttgttttgg | 120 |
| tgatacgtcc | atgtaatcca | ttttttcttt | agccataaca | gtgttattac | cacggaaacg | 180 |
| acaaacaact | tcatcatcta | agaaacgacc | attttcatca | agtctagaat | tagcctgtgc | 240 |
| aacaacgtag | ctatcctctt | catcagctgt | caaataatct | atttgatcag | tgattgagtt | 300 |
| tgtatctaaa | tccactttac | gatatggcgt | ttcaataaaa | ccaaattcat | tcactctagc | 360 |
| ataacttgac | aatgagttta | ttaaaccaat | attaggaccc | tcaggtgttt | caattggaca | 420 |
| catacgccca | tagtgagagt | agtgaacgtc | acgcacttcc | atttgagcac | gttcacgtgt | 480 |
| taatccacca | ggccctagag | cagataaacg | acgtttgt | | | 518 |

<210> SEQ ID NO 31
<211> LENGTH: 507
<212> TYPE: DNA
<213> ORGANISM: Staphylococcus cohnii

<400> SEQUENCE: 31

| | | | | | |
|---|---|---|---|---|---|
| ttctggattc | atcaatggga | ctgcttgacg | ttgcatgttc | gcacccatta | atgcacggtt | 60 |
| agagtcatcg | ttttctaaga | atggaataca | tgctgttgct | gcagaaacaa | cctgtttagg | 120 |
| agatacatcc | atgtaatcca | ttttttcttt | tgccataact | gtgttattac | cacggaaacg | 180 |
| acaaacaact | tcatcatcta | agaagcgacc | attttcatct | aacttagaat | ttgcttgtgc | 240 |
| tactacatag | ctatcttctt | cgtcagctgt | taaataatca | atttgatctg | tgatactatt | 300 |
| cgtttcaaga | tctactttac | gatatggcgt | ttcaatgaaa | ccaaattcat | ttacacgtgc | 360 |
| ataacttgat | aatgagttaa | tcaaaccaat | gtttggtccc | tctggtgttt | cgattggaca | 420 |
| catacgaccg | tagtgagagt | agtgaacgtc | acgcacttcc | atttgagcac | gttcacgtgt | 480 |
| taaaccacca | ggtcctaatg | ctgatag | | | | 507 |

<210> SEQ ID NO 32
<211> LENGTH: 507
<212> TYPE: DNA
<213> ORGANISM: Staphylococcus chromogenes

<400> SEQUENCE: 32

| | | | | | |
|---|---|---|---|---|---|
| ctcaggattt | aacaaaggca | ccgcttgacg | ttggatgttc | gcacccatta | acgcacggtt | 60 |
| agagtcatcg | ttttctaaga | acggaataca | tgcagttgcc | gcagaaacaa | cttgcttcgg | 120 |
| tgatacgtcc | atgtaatcca | ttttttcttt | agccattgtt | gtattgttcc | cacggaaacg | 180 |
| acaaacgatt | tcgtcgtcga | taaagcgtcc | attttcatct | aaacgtgagt | tcgctttggc | 240 |
| aacaacataa | ctgtcttctt | cgtccgcagt | taaataatca | atttgatcag | taattgcgtt | 300 |
| cgtttcaagg | tctactttac | gatacggcgt | ttcaataaaa | ccaaattcat | taacacgcgc | 360 |
| ataacttgaa | agtgagttga | ttaatccaat | atttggaccc | tctggtgttt | cgattggaca | 420 |
| catacgaccg | tagtgagaat | agtgaacgtc | acgcacttcc | atttgagcac | gttcacgtgt | 480 |
| taaaccacct | ggtcctaaag | cagataa | | | | 507 |

<210> SEQ ID NO 33
<211> LENGTH: 1025
<212> TYPE: DNA

-continued

<213> ORGANISM: Staphylococcus carnosus

<400> SEQUENCE: 33

| | | | | | |
|---|---|---|---|---|---|
| ttctggattc | atcaatggta | ccgcttgacg | ttgcatgttc | gcacccatta | atgcacggtt | 60
| agagtcatcg | ttttctaaga | atgggataca | agctgtcgca | gctgatacta | cttgttttgg | 120
| tgatacgtcc | atgtagtcca | ttttgtctct | gtccatcatt | tgttgttac | cacggaaacg | 180
| acaaacaact | tcttcgctga | tgaagtgacc | ttcatcatct | aaacgagagt | tcgcttgggc | 240
| tacaacatag | ctgtcttctt | cgtcagctgt | tagatagtcg | atttgatcag | ttacagtatt | 300
| agtttcaagg | tcaactttac | ggtatggtgt | ttcaataaaa | ccgaactcgt | taacacgtgc | 360
| ataacttgat | aatgagttga | tcaaaccaat | gtttggaccc | tcaggagttt | cgattggaca | 420
| catacggcca | tagtgagaat | agtgaacgtc | acgtacttcc | atttgagcac | gttcacgagt | 480
| taaaccacca | ggtcctaatg | cagataattc | tggattcatc | aatggtactg | cttgacgttg | 540
| catgttcgca | cccattaatg | cacgttaga | gtcatcattt | tctaagaatg | gaatacaagc | 600
| tgtcgctgca | gatactactt | gtttaggaga | tacatccatg | tagtccattt | tctctttagc | 660
| cataactgtg | ttattaccac | ggaaacgaca | acaacttcg | tcatctaaga | aacgaccatt | 720
| ttcgtctaaa | cgagagttcg | cttgggcaac | aacataacta | tcttcttcat | cagcagttaa | 780
| gtaatcaatt | tggtcagtga | tagaattcgt | atctaaatct | actttacgat | aaggtgtttc | 840
| aataaaacca | aattcattta | ctcgtgcata | acttgataat | gagttgatta | aaccaatgtt | 900
| tggtccctca | ggtgtttcga | ttggacacat | acggccatag | tgagaatagt | gaacgtcacg | 960
| cacttccatt | tgggcacgtt | cacgcgttaa | accaccaggt | cctaatgctg | atagacgacg | 1020
| tttat | | | | | 1025

<210> SEQ ID NO 34
<211> LENGTH: 518
<212> TYPE: DNA
<213> ORGANISM: Staphylococcus capitis

<400> SEQUENCE: 34

| | | | | | |
|---|---|---|---|---|---|
| ttcagtgttc | atcaatggta | ccgcttgacg | ttgcatgttc | gcacccatta | atgcacggtt | 60
| agagtcatcg | ttttctaaga | atggaataca | tgctgtagct | gctgatacaa | cttgtttagg | 120
| tgatacgtcc | atgtaatcca | ttttttcttt | tgccataact | gtgttattac | cacggaaacg | 180
| acaaacaacc | tcgtcatcta | agaaacgacc | attttcgtct | aaacgtgagt | tggcttgggc | 240
| aactacatag | ctatcttctt | catcagcagt | taagtaatcg | atttgatctg | tgatagagtt | 300
| cgtatctaaa | tcaactttac | gatacggtgt | ctcgatgaaa | ccaaattcat | ttactcgcgc | 360
| ataacttgat | aatgagttaa | ttaaaccaat | atttggaccc | tctggtgttt | caattggaca | 420
| catacgacca | tagtgtgagt | aatgaacgtc | acgtacttcc | atttgagcac | gttcacgagt | 480
| taaaccacca | ggtcctaatg | ctgatagacg | acgttttg | | 518

<210> SEQ ID NO 35
<211> LENGTH: 507
<212> TYPE: DNA
<213> ORGANISM: Staphylococcus auricularis

<400> SEQUENCE: 35

| | | | | | |
|---|---|---|---|---|---|
| ttctgggttc | attaaaggta | ccgcttgacg | ttgcatgttt | gcacccataa | gcgcacggtt | 60
| agagtcatcg | ttttctaaga | atggaataca | tgctgtcgct | gcagaaacaa | cttgtttagg | 120
| agatacatcc | atgtagtcca | tgcgttcttt | aggtttagta | gtgttgtccc | cacggaaacg | 180

-continued

```
acaaagaact tcatcatcaa cgaatttacc tgtttcatca agtacagagt ttgcttgtgc    240
aactacatag ctgtcttctt cgtcagctgt taagtagtcg attctgtcag taacttggtt    300
tgtctcgatg tttaccttac gataaggtgt ttcaatgaaa ccaaattcat taactcttgc    360
ataacttgat aatgagttga ttaaaccaat gtttggtccc tcaggcgttt caattggaca    420
catacgacca tagtgagagt agtgaacgtc acgtacttcc ataccagcac gctcacgagt    480
taaaccaccc ggtcctaatg ctgatag                                       507

<210> SEQ ID NO 36
<211> LENGTH: 518
<212> TYPE: DNA
<213> ORGANISM: Staphylococcus aureus

<400> SEQUENCE: 36
ttctggattc atcaaaggca ctgcttgacg ttgcatgttc gcacccatca atgcacggtt     60
tgagtcatca ttttctaaga atggaataca tgctgtcgct gctgaaacaa cttgcttcgg    120
cgatacatcc atataatcca ttttttcttt agccataact gtgttgttac cacggaaacg    180
acatacaact tcatcatcca tgaaacgacc attttcatct aatttagagt ttgcttgtgc    240
tacaacatag ctatcttctt cgtcagctgt taaatagtca atttgatcag tgatagcatg    300
tgtatctaaa tcaactttac gatatggtgt ttcaataaag ccgaattcat ttacacgtgc    360
ataacttgat aatgagttaa tcaatccaat gtttggtccc tcaggtgttt caattggaca    420
catacggcca tagtgagagt agtgaacgtc acgtacttcc atttgagcac gttcacgtgt    480
taaaccacca ggtcctaatg ctgatagacg acgtttat                           518

<210> SEQ ID NO 37
<211> LENGTH: 507
<212> TYPE: DNA
<213> ORGANISM: Staphylococcus aureus anaerobius

<400> SEQUENCE: 37
ttctggattc atcaaaggca ctgcttgacg ttgcatgttc gcacccatca atgcacggtt     60
tgagtcatca ttttctaaga atggaataca tgctgtcgct gctgaaacaa cttgcttcgg    120
cgatacatcc atataatcca ttttttcttt agccataact gtattgttac cacggaaacg    180
acatacaact tcatcatcca tgaaacgacc attttcatct aatttagagt ttgcttgtgc    240
tacaacatag ctatcttctt cgtcagctgt taaatagtca atttgatcag tgatagcatg    300
tgtatctaaa tcaactttac gatatggtgt ttcaataaag ccgaattcat ttacacgtgc    360
ataacttgat aatgagttaa tcaatccaat gtttggtccc tcaggtgttt caattggaca    420
catacggcca tagtgagagt agtgaacgtc acgtacttcc atttgagcac gttcacgtgt    480
taaaccacca ggtcctaatg ccgatag                                       507

<210> SEQ ID NO 38
<211> LENGTH: 518
<212> TYPE: DNA
<213> ORGANISM: Staphylococcus arlettae

<400> SEQUENCE: 38
ttcacggttc atcaacggta ctgcttgacg ttgcatgttc gcacccatta atgcacggtt     60
agagtcatcg ttttctaaga aaggaataca tgccgttgca gctgaaacta cttgcttagg    120
tgatacgtcc atgtagtcca ttttttcttt agccataact gtgttattac cgcggaaacg    180
```

-continued

| | |
|---|---|
| acaaacaact tcgtcatcta aaaacttacc attttcatct aagttagagt tggcttgtgc | 240 |
| taccacatag ctgtcctctt catcagcagt taggtaatca atttgatctg taattgagtt | 300 |
| tgttgctaaa tctactttac ggtacggcgt ttcgataaag ccaaattcat ttacacgtgc | 360 |
| ataacttgat agtgagttaa ttaaaccgat gtttggtccc tctggtgttt cgataggaca | 420 |
| catacggcca tagtgagaat agtgtacgtc acgtacttcc atttgagcac gttcacgtgt | 480 |
| taaaccacca ggtcctaatg ctgataaacg acgtttat | 518 |

<210> SEQ ID NO 39
<211> LENGTH: 556
<212> TYPE: DNA
<213> ORGANISM: Staphylococcus caprae

<400> SEQUENCE: 39

| | |
|---|---|
| taacccatta gctgagttga ctcataaacg tcgtctatca gcattaggac ctggtggttt | 60 |
| aacgcgtgaa cgtgcccaaa tggaagtgcg tgacgttcac tattctcact atggccgtat | 120 |
| gtgtccaatc gaaacacctg agggaccaaa cattggttta atcaactcat tatcaagtta | 180 |
| tgcacgagta aatgaatttg gttttattga aacaccttat cgtaaagtag atttagatac | 240 |
| gaattctatc actgaccaaa ttgattactt aactgctgat gaagaagata gttatgttgt | 300 |
| tgcccaagcg aactctcgtt tagacgaaaa tggtcgtttc ttagatgacg aagttgtttg | 360 |
| tcgtttccgt ggtaataaca cagttatggc taaagagaaa atggactaca tggatgtatc | 420 |
| tcctaaacaa gtagtatctg cagcgacagc ttgtattcca ttcttagaaa atgatgactc | 480 |
| taaccgtgca ttaatgggtg cgaacatgca acgtcaagca gtaccattga tgaatccaga | 540 |
| agcgccattt gttggt | 556 |

<210> SEQ ID NO 40
<211> LENGTH: 20
<212> TYPE: DNA
<213> ORGANISM: Artificial Sequence
<220> FEATURE:
<223> OTHER INFORMATION: primer

<400> SEQUENCE: 40

| | |
|---|---|
| ggtttaggat taaaagatgc | 20 |

<210> SEQ ID NO 41
<211> LENGTH: 19
<212> TYPE: DNA
<213> ORGANISM: Artificial Sequence
<220> FEATURE:
<223> OTHER INFORMATION: primer

<400> SEQUENCE: 41

| | |
|---|---|
| gaagaagttg gagctactg | 19 |

<210> SEQ ID NO 42
<211> LENGTH: 21
<212> TYPE: DNA
<213> ORGANISM: Artificial Sequence
<220> FEATURE:
<223> OTHER INFORMATION: primer

<400> SEQUENCE: 42

| | |
|---|---|
| aataagagca gggaaagaaa c | 21 |

<210> SEQ ID NO 43
<211> LENGTH: 22

```
<212> TYPE: DNA
<213> ORGANISM: Artificial Sequence
<220> FEATURE:
<223> OTHER INFORMATION: primer

<400> SEQUENCE: 43
aaagaaaaga atgaatgaac tt                                            22

<210> SEQ ID NO 44
<211> LENGTH: 21
<212> TYPE: DNA
<213> ORGANISM: Artificial Sequence
<220> FEATURE:
<223> OTHER INFORMATION: primer

<400> SEQUENCE: 44
tatgcttatg gtatttagct a                                             21

<210> SEQ ID NO 45
<211> LENGTH: 25
<212> TYPE: DNA
<213> ORGANISM: Artificial Sequence
<220> FEATURE:
<223> OTHER INFORMATION: primer

<400> SEQUENCE: 45
aaacttaata gaaattcaaa ctaaa                                         25

<210> SEQ ID NO 46
<211> LENGTH: 21
<212> TYPE: DNA
<213> ORGANISM: Artificial Sequence
<220> FEATURE:
<223> OTHER INFORMATION: primer

<400> SEQUENCE: 46
gttcaaacga taaatagaga a                                             21

<210> SEQ ID NO 47
<211> LENGTH: 20
<212> TYPE: DNA
<213> ORGANISM: Artificial Sequence
<220> FEATURE:
<223> OTHER INFORMATION: primer

<400> SEQUENCE: 47
gaaacagatg ctaaagatgt                                               20

<210> SEQ ID NO 48
<211> LENGTH: 20
<212> TYPE: DNA
<213> ORGANISM: Artificial Sequence
<220> FEATURE:
<223> OTHER INFORMATION: primer

<400> SEQUENCE: 48
ccatatactg cgagtgggaa                                               20

<210> SEQ ID NO 49
<211> LENGTH: 26
<212> TYPE: DNA
<213> ORGANISM: Artificial Sequence
<220> FEATURE:
<223> OTHER INFORMATION: primer

<400> SEQUENCE: 49
```

-continued tagaaattca atcaattaag tatatg    26

<210> SEQ ID NO 50
<211> LENGTH: 20
<212> TYPE: DNA
<213> ORGANISM: Artificial Sequence
<220> FEATURE:
<223> OTHER INFORMATION: primer

<400> SEQUENCE: 50
ttggtaatgc tttaccagat    20

<210> SEQ ID NO 51
<211> LENGTH: 25
<212> TYPE: DNA
<213> ORGANISM: Artificial Sequence
<220> FEATURE:
<223> OTHER INFORMATION: primer

<400> SEQUENCE: 51
tgcattacac cagcagatat cattg    25

<210> SEQ ID NO 52
<211> LENGTH: 20
<212> TYPE: DNA
<213> ORGANISM: Artificial Sequence
<220> FEATURE:
<223> OTHER INFORMATION: primer

<400> SEQUENCE: 52
gatgatattg accatttagg    20

<210> SEQ ID NO 53
<211> LENGTH: 21
<212> TYPE: DNA
<213> ORGANISM: Artificial Sequence
<220> FEATURE:
<223> OTHER INFORMATION: primer

<400> SEQUENCE: 53
tgaaagaatg tcaattcaag a    21

<210> SEQ ID NO 54
<211> LENGTH: 18
<212> TYPE: DNA
<213> ORGANISM: Artificial Sequence
<220> FEATURE:
<223> OTHER INFORMATION: primer

<400> SEQUENCE: 54
aaacccatta gctgagtt    18

<210> SEQ ID NO 55
<211> LENGTH: 26
<212> TYPE: DNA
<213> ORGANISM: Artificial Sequence
<220> FEATURE:
<223> OTHER INFORMATION: primer

<400> SEQUENCE: 55
tggtcgtttc atggatgatg aagttg    26

<210> SEQ ID NO 56
<211> LENGTH: 20
<212> TYPE: DNA
<213> ORGANISM: Artificial Sequence

```
<220> FEATURE:
<223> OTHER INFORMATION: primer

<400> SEQUENCE: 56
aagatagcta tgttgtagca                                               20

<210> SEQ ID NO 57
<211> LENGTH: 21
<212> TYPE: DNA
<213> ORGANISM: Artificial Sequence
<220> FEATURE:
<223> OTHER INFORMATION: primer

<400> SEQUENCE: 57
cttagagaac gatgactcta a                                             21

<210> SEQ ID NO 58
<211> LENGTH: 22
<212> TYPE: DNA
<213> ORGANISM: Artificial Sequence
<220> FEATURE:
<223> OTHER INFORMATION: primer

<400> SEQUENCE: 58
tagttggttt catgacttgg ga                                            22

<210> SEQ ID NO 59
<211> LENGTH: 20
<212> TYPE: DNA
<213> ORGANISM: Artificial Sequence
<220> FEATURE:
<223> OTHER INFORMATION: primer

<400> SEQUENCE: 59
ttgaaagtcc aacaaagcaa                                               20

<210> SEQ ID NO 60
<211> LENGTH: 21
<212> TYPE: DNA
<213> ORGANISM: Artificial Sequence
<220> FEATURE:
<223> OTHER INFORMATION: primer

<400> SEQUENCE: 60
ggtaaagtaa cgcctaaagg t                                             21

<210> SEQ ID NO 61
<211> LENGTH: 20
<212> TYPE: DNA
<213> ORGANISM: Artificial Sequence
<220> FEATURE:
<223> OTHER INFORMATION: primer

<400> SEQUENCE: 61
tggaggtatg ggcacttgaa                                               20

<210> SEQ ID NO 62
<211> LENGTH: 20
<212> TYPE: DNA
<213> ORGANISM: Artificial Sequence
<220> FEATURE:
<223> OTHER INFORMATION: primer

<400> SEQUENCE: 62
acatctttag catctgtttc                                               20
```

<210> SEQ ID NO 63
<211> LENGTH: 20
<212> TYPE: DNA
<213> ORGANISM: Artificial Sequence
<220> FEATURE:
<223> OTHER INFORMATION: primer

<400> SEQUENCE: 63
atcgtttgaa cgccactctt                                         20

<210> SEQ ID NO 64
<211> LENGTH: 20
<212> TYPE: DNA
<213> ORGANISM: Artificial Sequence
<220> FEATURE:
<223> OTHER INFORMATION: primer

<400> SEQUENCE: 64
tcatagtaag tttgcgccat                                         20

<210> SEQ ID NO 65
<211> LENGTH: 20
<212> TYPE: DNA
<213> ORGANISM: Artificial Sequence
<220> FEATURE:
<223> OTHER INFORMATION: primer

<400> SEQUENCE: 65
atctggtaaa gcattaccaa                                         20

<210> SEQ ID NO 66
<211> LENGTH: 25
<212> TYPE: DNA
<213> ORGANISM: Artificial Sequence
<220> FEATURE:
<223> OTHER INFORMATION: primer

<400> SEQUENCE: 66
caatgatatc tgctggtgta atgca                                   25

<210> SEQ ID NO 67
<211> LENGTH: 20
<212> TYPE: DNA
<213> ORGANISM: Artificial Sequence
<220> FEATURE:
<223> OTHER INFORMATION: primer

<400> SEQUENCE: 67
cctaaatggt caatatcatc                                         20

<210> SEQ ID NO 68
<211> LENGTH: 20
<212> TYPE: DNA
<213> ORGANISM: Artificial Sequence
<220> FEATURE:
<223> OTHER INFORMATION: primer

<400> SEQUENCE: 68
cgaatattaa ttaattgttg                                         20

<210> SEQ ID NO 69
<211> LENGTH: 24
<212> TYPE: DNA
<213> ORGANISM: Artificial Sequence
<220> FEATURE:
<223> OTHER INFORMATION: primer

<400> SEQUENCE: 69
gtgatagcat gtgtatctaa atca                                    24

<210> SEQ ID NO 70
<211> LENGTH: 20
<212> TYPE: DNA
<213> ORGANISM: Artificial Sequence
<220> FEATURE:
<223> OTHER INFORMATION: primer

<400> SEQUENCE: 70
taactatctt cttcatcagc                                         20

<210> SEQ ID NO 71
<211> LENGTH: 20
<212> TYPE: DNA
<213> ORGANISM: Artificial Sequence
<220> FEATURE:
<223> OTHER INFORMATION: primer

<400> SEQUENCE: 71
tgctacaaca tagctatctt                                         20

<210> SEQ ID NO 72
<211> LENGTH: 26
<212> TYPE: DNA
<213> ORGANISM: Artificial Sequence
<220> FEATURE:
<223> OTHER INFORMATION: primer

<400> SEQUENCE: 72
caacttcatc atccatgaaa cgacca                                  26

<210> SEQ ID NO 73
<211> LENGTH: 21
<212> TYPE: DNA
<213> ORGANISM: Artificial Sequence
<220> FEATURE:
<223> OTHER INFORMATION: primer

<400> SEQUENCE: 73
atgcaacgtc aggccgttcc g                                       21

<210> SEQ ID NO 74
<211> LENGTH: 20
<212> TYPE: DNA
<213> ORGANISM: Artificial Sequence
<220> FEATURE:
<223> OTHER INFORMATION: primer

<400> SEQUENCE: 74
agacgacgaa cagaatttca                                         20

<210> SEQ ID NO 75
<211> LENGTH: 20
<212> TYPE: DNA
<213> ORGANISM: Artificial Sequence
<220> FEATURE:
<223> OTHER INFORMATION: primer

<400> SEQUENCE: 75
gctcgaatga taacgtgatt                                         20

<210> SEQ ID NO 76

```
<211> LENGTH: 20
<212> TYPE: DNA
<213> ORGANISM: Artificial Sequence
<220> FEATURE:
<223> OTHER INFORMATION: primer

<400> SEQUENCE: 76
acttgtccaa tgttcatacg                                               20

<210> SEQ ID NO 77
<211> LENGTH: 21
<212> TYPE: DNA
<213> ORGANISM: Artificial Sequence
<220> FEATURE:
<223> OTHER INFORMATION: primer

<400> SEQUENCE: 77
catatgcttc aagtgcccat a                                             21

<210> SEQ ID NO 78
<211> LENGTH: 20
<212> TYPE: DNA
<213> ORGANISM: Artificial Sequence
<220> FEATURE:
<223> OTHER INFORMATION: primer

<400> SEQUENCE: 78
ccaagtggtt gttgtgtaac                                               20

<210> SEQ ID NO 79
<211> LENGTH: 20
<212> TYPE: DNA
<213> ORGANISM: Artificial Sequence
<220> FEATURE:
<223> OTHER INFORMATION: primer

<400> SEQUENCE: 79
tttagagctt tcactgtttg                                               20

<210> SEQ ID NO 80
<211> LENGTH: 21
<212> TYPE: DNA
<213> ORGANISM: Artificial Sequence
<220> FEATURE:
<223> OTHER INFORMATION: primer

<400> SEQUENCE: 80
caccatatga ccaagaacga a                                             21

<210> SEQ ID NO 81
<211> LENGTH: 22
<212> TYPE: DNA
<213> ORGANISM: Artificial Sequence
<220> FEATURE:
<223> OTHER INFORMATION: primer

<400> SEQUENCE: 81
caatcaagga gcctacctcc tt                                            22

<210> SEQ ID NO 82
<211> LENGTH: 21
<212> TYPE: DNA
<213> ORGANISM: Artificial Sequence
<220> FEATURE:
<223> OTHER INFORMATION: primer

<400> SEQUENCE: 82
```

```
gaaattattt acatcaatca a                                                    21

<210> SEQ ID NO 83
<211> LENGTH: 20
<212> TYPE: DNA
<213> ORGANISM: Artificial Sequence
<220> FEATURE:
<223> OTHER INFORMATION: primer

<400> SEQUENCE: 83
taactatctt cttcatcagc                                                      20

<210> SEQ ID NO 84
<211> LENGTH: 20
<212> TYPE: DNA
<213> ORGANISM: Artificial Sequence
<220> FEATURE:
<223> OTHER INFORMATION: primer

<400> SEQUENCE: 84
cccagtcttt tgtaggtccg                                                      20

<210> SEQ ID NO 85
<211> LENGTH: 20
<212> TYPE: DNA
<213> ORGANISM: Artificial Sequence
<220> FEATURE:
<223> OTHER INFORMATION: primer

<400> SEQUENCE: 85
cccattcttt cacgacgtac                                                      20
```

MOLECULAR IDENTIFICATION OF *STAPHYLOCOCCUS*-GENUS BACTERIA

The present invention pertains to the area of diagnosis. More precisely, the invention concerns a method for the molecular identification of bacteria of the *Staphylococcus* genus using detection and/or amplifying and sequencing techniques with probes or oligonucleotide primers applied to strains of this bacterial genus.

Bacteria of the *Staphylococcus* genus are Gram-positive and catalase-positive cocciform bacteria of which 36 species are currently known including 9 with sub-species [Euzé by J P. (1997) Int J Syst Bacteriol 47:590-2]. These species are coagulase-negative, with the exception of *Staphylococcus aureus, Staphylococcus intermedius, Staphylococcus delphinii, Staphylococcus schleiferi* subsp. *coagulans*, and a few strains of *Staphylococcus hyicus* [Kloos W E (1995) in Manual of Clinical Micriobiology, pp 282-298, ASM Press]. These species are readily and routinely isolated and cultivated from environmental samples, veterinary clinical samples and human clinical samples [Kloos W E (1986) in Bergey's Manual of Systematic Bacteriology, pp. 1013-1035, Williams & Wilkins]. In man, *Staphylococcus aureus* is a coagulase-positive species responsible for food poisoning related to the production of an enterotoxin, for staphylococcal toxic shock syndrome and for purulent infections characterized by septic metastases remote from the initial site of infection. Strains of *Staphylococcus aureus* resistant to methicillin, a first-line antibiotic to fight infection, represent a major problem for public health regarding nosocomial infections, i.e. infections contracted by patients in hospitals and other care institutions. Bacteria belonging to species of the coagulase-negative *Staphylococcus* genus form part of the normal flora in man. These species are also responsible for nosocomial infections, especially through infection from implanted foreign material, prostheses in particular [Kloos W E (1994) Clin. Microbiol. Rev. 7:117-140].

These different species raise the problem of their identification. Conventional phenotype identification methods are the most frequently used to identify bacteria belonging to species of the *Staphylococcus* genus [Kloos W E (1991) J. Clin. Microbiol. 29:738-744] and several identification kits and automated units have been developed to assist in the phenotype identification of bacteria of the *Staphylococcus* genus. However, the extent of identification in routine practice is variable [Grant C E (1994) Diagn. Microbiol. Infect. Dis. 18:1-5; Perl T M (1994) Diagn. Microbiol. Infect. Dis. 18, 151-5; Refshal K (1992) J. Hosp. Infect. 22, 19-31]: for example these systems mostly confuse between bacteria belonging to the *Staphylococcus hominis* and *Staphylococcus warneri* species with error rates of 27 to 36% [Gran C E (1994) Diagn. Microbiol. Infect. Dis. 18:1-5; Leven M (1995) J. Clin. Microbiol. 33:1060-3]. Similarly, *Staphylococcus schleiferi* can be misidentified by automated identification systems [Calvo J. (2000) J. Clin. Microbiol. 38:3887-9]. Molecular methods can in theory give better results when identifying bacteria of the *Staphylococcus* genus on account of their sensitivity and specificity. The molecular targets currently proposed for the molecular identification of *Staphylococcus* bacteria comprise the 16S rDNA gene encoding the 16S sub-unit of ribosomal RNA [Bialkowska-Hobrzanska H et al. (1990) Eur. J. Microbiol. Infect. Dis. 9:588-594], the intergenic spacer encoding transfer RNAs [Maes N. et al (1997) J. Clin. Microbiol. 35:2477-2481], the hsp60 gene encoding the heat shock protein 60 [Goh S H et al. (1996) J. Clin. Microbiol. 34:818-823; Goh S H (1997) J. Clin. Microbiol. 35, 3116-3121; Kwok A Y (1999) Int. J. Syst. Bacteriol. 49, 1181-1192] and the femA gene [Vannuffel P et al, Res. Microbiol. 150:129-141]. Hybridization of oligonucleotides is the technique generally offered to target these identification regions. Detection of the nuc gene is limited to bacteria of the *Staphylococcus aureus* species [Brakstad O G (1992) J. Clin. Microbiol. 30:1654-1660] and a chromosomal fragment has been reported for the identification of bacteria of the *Staphylococcus epidermidis* species [Martineau F (1996) J. Clin. Microbiol. 34:2888-2893]. There still exists, therefore, a demand for a molecular identification tool for bacteria of the *Staphylococcus* species which can be routinely used in bacteriology laboratories [Kleeman K T (1993) J. Clin. Microbiol. 31, 1318-1321].

The inventors have shown in this invention that the rpoB gene constitutes a genetic marker enabling the detection and specific identification of the bacteria of each species of the *Staphylococcus* genus.

More particularly, the present invention concerns sequences of specific nucleic acids of the genus or of each species of the *Staphylococcus* genus whose nucleotide sequence is drawn from the rpoB gene of said bacteria.

According to Lazcano et al [J. Mol. Evol. (1988) 27:365-376], RNA polymerases are divided into two groups depending upon their origin, one formed by viral RNA- or DNA-dependent RNA polymerases, and the other formed by DNA-dependent RNA polymerases of eukaryotic or prokaryotic origin (archaebacteria and eubacteria). Eubacterial DNA-dependent RNA polymerases are characterized by a simple, multimeric, conserved structure noted "core enzyme" represented by $\alpha\beta\beta'$ or "holoenzyme" represented by $\alpha\beta\beta\sigma$ [Yura and Ishihama, Ann. Rev. Genet. (1979) 13:59-97]. Numerous studies have highlighted the functional role, within the multimeric enzyme complex, of the $\beta$ subunit of eubacterial RNA polymerase. Archaebacterial and eukaryotic RNA polymerases, for their part, have a more complex structure possibly reaching a dozen or even around thirty subunits [Pühlet et al. Proc. Natl. Acad. Sci. USA (1989) 86:4569-4573].

The genes encoding the different $\alpha\beta\beta'\sigma$ subunits of DNA-dependent RNA polymerase in eubacteria, respectively the rpoA, rpoB, rpoC and rpoD genes, are classified in different groups comprising the genes coding for the proteins forming ribosomal subunits or for enzymes involved in the replication and repair of the genome [Yura and Yshihma, Ann. Rev. Genet. (1979) 13:59-97]. Some authors have shown that the sequences of the rpoB and rpoC genes could be used to construct phylogenetic trees ([Rowland et al. Biochem. Soc. Trans. (1992) 21:40 S) enabling separation of the different branches and sub-branches among the kingdoms of the living.

Before setting forth the invention in more detail, different terms used in the description and claims are defined below:

by "nucleic acid extracted from bacteria" is meant either total nucleic acid, or genomic DNA, or messenger RNAs or further DNA obtained from reverse transcription of messenger RNAs;

a "nucleotide fragment" or an oligonucleotide are two synonymous terms denoting a chain of nucleotide patterns characterized by an information sequence of natural (or optionally modified) nucleic acids able to hybridize, like natural nucleic acids, with a complementary or substantially complementary nucleotide fragment under pre-determined conditions of high stringency. The chain may contain nucleotide patterns of different structure from that of natural nucleic acids. A nucleotide fragment (or oligonucleotide) may for example contain up to 100 nucleotide patterns. It generally contains at least 10, and in particular at least 12 nucleotide patterns and may be obtained from a molecule of natural nucleic acid and/or by genetic recombination and/or by chemical synthesis.

a nucleotide pattern is derived from a monomer which may be a natural nucleotide of nucleic acid whose constituent parts are a sugar, a phosphate group and a nitrogenous base chosen from among adenine (A), guanine (G), uracil (U), cytosine (C), thymine (T); or else the monomer is a nucleotide modified in at least one the three preceding constituent parts; by way of example, the modification may occur either at the bases, with modified bases such as inosine which can hybridise with any A, T, U, C or G base, methyl-5-deoxycytidine, deoxyuridine, dimethylamino-5-dexyuridine or any other modified base able to hybridize, or at the sugar level, for example the replacement of at least one deoxyribose by a polyamide [Nielsen P E et al., Science (1991) 254:1497-15000] or further at the phosphate group level, for example through replacement by esters chosen in particular from among diphosphates, alkylphosphates and phosphorothioates, by "hybridization" is meant the process during which, under appropriate conditions, two nucleotide fragments having sufficiently complementary sequences are able to associate together through stable, specific hydrogen bonds, to form a double strand. Hybridization conditions are determined by "stringency", i.e. the strictness of operating conditions. Hybridization is all the more specific the more it is performed under high stringency. Stringency is related in particular to the base composition of a probe/target duplex, and by the extend of mismatch between two nucleic acids. Stringency may also depend upon the parameters of the hybridization reaction, such as concentration and the type of ion species present in the hybridization solution, the type and concentration of denaturing agents and/or hybridization temperature. The stringency of the conditions under which a hybridization reaction is to be performed depends in particular upon the probes used. All this data is well known and the appropriate conditions may possibly be determined in each case through routine experiments. In general, depending upon the length of the probes used, the temperature for hybridization reaction lies between approximately 20 and 65° C., in particular between 35 and 65° C. in a saline solution at a concentration of approximately 0.8 to 1 M.

a "probe" is a nucleotide fragment having hybridization specificity under determined conditions to form a hybridization complex with a nucleic acid having, in this case, a nucleotide sequence included either in a messenger RNA, or in a DNA obtained by reverse transcription of said messenger RNA, the product of transcription; a probe may be used for diagnostic purposes (in particular capture or detection probes) or for therapeutic purposes, a "capture probe" is a probe that is immobilized or can be immobilized on a solid carrier by any appropriate means, by covalence for example, by adsorption or direct synthesis on a solid. Examples of carriers include microtitration plates and DNA chips, a "detection probe" is a probe labeled with a marking agent chosen for example from radioactive isotopes, enzymes, in particular enzymes able to act on a chromogenous, fluorigenous or luminescent substrate (in particular a peroxydase or an alkaline phosphatase), chromophor chemical compounds, chromogenous, fluorigenous or luminescent compounds, analogues of nucleotide bases and ligands such as biotin, a "species probe" is a probe enabling specific identification of the species of a bacterium, a "genus probe" is a probe enabling specific identification of the genus of a bacterium, a "primer" is a probe containing for example 10 to 100 nucleotide patterns and having hybridization specificity under determined conditions for enzyme amplification reactions, by "amplification reaction" is meant an enzyme polymerization reaction, for example in an amplifying technique such as PCR, initiated by primer oligonucleotides and using a DNA polymerase, by "sequencing reaction" is meant the obtaining of the sequence of a nucleic acid fragment or of a complete gene using an abortive polymerization method with oligonucleotide primers and using said dideoxynucleotides [Sanger F, Coulson A R (1975), J. Mol. Biol. 94: 441] or by multiple hybridizations with multiple probes fixed on a solid carrier such as used in DNA chips for example.

The inventors have determined the complete sequences of the rpoB genes of four species of bacteria of the *Staphylococcus* genus. These four species were chosen by the inventors as representing the four main genetic groups determined on the basis of studies on the 16S gene in bacteria of the *Staphylococcus* genus, namely the species that are the most divergent phylogenetically among all the species currently described in this genus, so that the alignment of the rpoB sequences obtained in these four species may, most probably, phylogenetically encompass all the rpoB sequences of all the species of this bacterial genus.

The inventors have evidenced the consensus and specific sequences SEQ ID NOs:7 to 10 described in the list of sequences at the end of the description. The inventors have determined said sequences SEQ ID NOs:7 to 10 as being not only consensual between all bacteria of the *Staphylococcus* genus but also specific to the family of bacteria of the *Staphylococcus* genus, with the exception of *Staphylococcus schleiferi* in respect of sequence SEQ ID NO:8.

These sequences are present in the rpoB genes of all bacteria of the *Staphylococcus* genus and are specific to bacteria of the *Staphylococcus* genus which may be used as genus probe to detect any bacteria of the *Staphylococcus* genus with the exception of *Staphylococcus schleiferi* regarding sequence SEQ ID NO:8.

In sequences SEQ ID NOs:7 and 10, the nucleotide N mentioned in the list of sequences at the end of the description, may represent inosine or an equimolar mixture of 4 different nucleotides chosen from among A, T, C and Gt, or A, U, C and G respectively insofar as, as mentioned in the definitions, an oligonucleotide or a fragment of nucleic acid according to the invention may be in the form of an oxyribonucleic acid (DNA) or a ribonucleic acid (RNA) for which, in this case, T is replaced by U.

When "N" represents said equimolar mixture of nucleotides at a given position, this means that the nucleotide at the said given position indifferently represents A, T, C or G (or respectively A, U, C or G when applicable) and that the oligonucleotide of the invention is more precisely made up of an equimolar mixture of 4 groups of oligonucleotides in each of which N has a different meaning at said given position and respectively represents each of the 4 bases A, T, C or G (or respectively A, U, C or G).

At the position corresponding to a nucleotide N in sequences SEQ ID NOs:7 and 10, variable nucleotides are found in the complementary target sequences in relation to the species of the bacterium under consideration, but all the other nucleotides are conserved in all the species of the bacteria of the *Staphylococcus* genus. Since "N" represents inosine which is able to hybridize with any base, or an equimolar mixture of the 4 bases A, T, C, G, the sequences SEQ ID NOs:7 and 10 can hybridize with the complementary sequence included in the rpoB gene of all the bacteria of the *Staphylococcus* genus.

In addition, the consensus sequences SEQ ID NO:9 and SEQ ID NO:10 flank hypervariable sequences whose sequence is specific to each bacterial species of the *Staphylococcus* genus. The sequences flanked by SEQ ID NOs:9 and 10 may therefore be used a species probes for bacteria of the *Staphylococcus* genus.

Also, the sequences SEQ ID NOs:9 and 10 were determined as flanking a fragment of the rpoB gene comprising a zone whose variable length is approximately 500 by and forms the shortest specific sequence for each bacterial species of the *Staphylococcus* genus.

The inventors were therefore able to identify species probes for each of the 29 bacterial species of the *Staphylococcus* genus studied, corresponding to the sequences SEQ ID NOs:11 to 39 flanked by the consensus sequences SEQ ID NOs:9 and 10.

Consensus sequences SEQ ID NOs:7 to 10 identified in the invention, may be used as amplification or sequencing reaction primer in methods to detect bacteria of the *Staphylococcus* genus by molecular identification.

Sequences SEQ ID NOs:7 to 10 therefore not only make it possible to prepare genus probes for bacteria of the *Staphylococcus* genus, but also to detect and identify the species of said bacteria by amplification and sequencing using said sequences as primers.

More precisely, the present invention provides a method for detecting, by identification, a bacterium of a species of the *Staphylococcus* genus, characterized in that use is made of:

the rpoB gene of said bacterium or a fragment of said rpoB gene of said bacterium, comprising a nucleotide sequence chosen from among one of the sequences SEQ ID NOs:11 to 29 and 31 to 39, the reverse sequences and the complementary sequences, or a fragment of said rpoB gene of said bacterium, consisting of nucleotide sequence SEQ ID NO:39, the reverse sequence and the complementary sequence, or an oligonucleotide comprising a sequence of at least 12 consecutive nucleotide patterns, included in one of sequences SEQ ID NOs:7 to 10, in which N represents a nucleotide chosen from among inosine or an equimolar mixture of 4 different nucleotides chosen from among A, T, C or G, the reverse sequences and the complementary sequences.

Said oligonucleotides preferably comprise 12 to 35 nucleotide patterns, and further preferably said oligonucleotides consist of sequences SEQ ID NOs:7 to 10, the reverse sequences and the complementary sequences.

In one first embodiment of a detection method according to the invention, it is sought to show the presence of a bacterium of the *Staphylococcus* genus and, in a first variant, the steps are performed in which:

1—at least one genus probe is contacted comprising a said oligonucleotide containing a sequence included in one of sequences SEQ ID NOs:7 to 10, the reverse sequences and the complementary sequences, and 2—the formation or non-formation is determined of a hybridization complex between said genus probe and the nucleic acids of the sample, and the presence is determined of said bacterium of the *Staphylococcus* genus if there is formation of a hybridization complex.

In a second variant of embodiment of the detection method for a bacterium of the *Staphylococcus* genus, the steps are performed in which:

1—the amplification primers comprising said oligonucleotides containing a sequence of at least 12 nucleotide patterns included in at least two sequences drawn from sequences SEQ ID NOs:7 to 10, reverse sequences and complementary sequences, are contacted with a sample containing or likely to contain nucleic acids of at least one said bacterium of the *Staphylococcus* genus, with:

as 5' primer: an oligonucleotide chosen from among the oligonucleotides comprising a sequence included in one of sequences SEQ ID NOs:7 to 9 or the complementary sequences, preferably an oligonucleotide consisting of said complete sequences, and as 3' primer: an oligonucleotide comprising a sequence included in one of sequences SEQ ID NO:10 or 8 or respectively a complementary sequence, preferably an oligonucleotide consisting of said complete sequences.

2—amplification of the nucleic acids is conducted by enzymatic polymerization reaction and the onset or absence of an amplification product is determined, and hence the presence of said bacterium is determined in the sample if an amplification product occurs.

More particularly, in this second variant of the first embodiment, as 5' primer an oligonucleotide of sequence SEQ ID NO:7 or 9 is used or a complementary sequence, and as 3' primer an oligonucleotide of sequence SEQ ID NO:10 or respectively a complementary sequence.

In a second embodiment of the method for bacterium detection according to the invention, it is sought to specifically detect a given species of a bacterium of the *Staphylococcus* genus chosen from among the species: *Staphylococcus xylosus*, *Staphylococcus warneri*, *Staphylococcus simulans*, *Staphylococcus sciuri*, *Staphylococcus schleiferi*, *Staphylococcus saphrophyticus*, *Staphylococcus saccharolyticus*, *Staphylococcus pulveris*, *Staphylococcus muscae*, *Staphylococcus lugdunensis*, *Staphylococcus lentis*, *Staphylococcus kloosii*, *Staphylococcus intermedius*, *Staphylococcus hyicus*, *Staphylococcus hominis*, *Staphylococcus haemolyticus*, *Staphylococcus gallinarum*, *Staphylococcus felis*, *Staphylococcus equorum*, *Staphylococcus epidermis*, *Staphylococcus cohni*, *Staphylococcus chromogenes*, *Staphylococcus carnosus*, *Staphylococcus capitis*, *Staphylococcus auricularis*, *Staphylococcus aureus* subs. *aureus*, *Staphylococcus aureus* subs. *anaerobius*, *Staphylococcus arlettae*, *Staphylococcus caprae*.

In a first variant of this second embodiment of the method of the invention, the steps are performed in which:

1—a sample containing or likely to contain nucleic acids of at least one said bacterium is contacted with at least one species probe consisting of a said gene fragment containing a sequence included in one of the sequences SEQ ID NOs:11 to 39, the reverse sequences and complementary sequences, preferably an oligonucleotide consisting of one of said sequences SEQ ID NOs:11 to 39, or an oligonucleotide of reverse or complementary sequence, and 2—the formation or absence is determined of a hybridization complex between said probe and the nucleic acids of the sample.

In a second variant of this said second embodiment of the method of the invention in which it is sought to specifically detect a given species of a bacterium of the *Staphylococcus* genus chosen from among the 29 species cites above, the method comprises the steps in which, in a sample containing or likely to contain nucleic acids of at least one said bacterium:

a) a sequencing reaction is conducted of a fragment of the amplified rpoB gene of said given bacterium using nucleotide primers consisting of oligonucleotides comprising a sequence included in sequences SEQ ID NO:7 or 9 as 5' primer, and SEQ ID NO:10 as 3' primer, preferably oligonucleotides consisting of said sequences SEQ ID NO:7 or 9 and SEQ ID NO:10, or their complementary sequences, and b) the presence or absence is determined of the given species of said bacterium by comparing the sequence of said fragment obtained with the sequence of the complete rpoB gene of said bacterium or the sequence of a fragment of the rpoB gene of said bacterium respectively comprising said sequences SEQ ID NOs:11 to 39 and complementary sequences, and in this way the presence of said bacterium in the sample is determined if the sequence of the fragment obtained is identical to the known sequence of the genus or of the fragment of the rpoB gene of said bacterium.

More particularly, in this second variant:

at step a) the steps are performed comprising:

1—a first amplification of the nucleic acid of said sample with a pair of 5' and 3' primers chosen from among oligonucleotides respectively containing sequences SEQ ID NO:7 and respectively SEQ ID NO:10 or their complementary sequences, and the occurrence or absence of an amplification product at step 1 is determined, and 2—a sequencing reaction is conducted of the amplicons determined at step 1 with the 5' and 3' primers consisting of oligonucleotides containing sequences SEQ ID NO:9 and respectively SEQ ID NO:10, preferably consisting of said sequences SEQ ID NOs:7 and 10 or their complementary sequences, preferably consisting of said sequences SEQ ID NOs:9 and 10 or their complementary sequences, and at step b), a comparison is made between the sequences obtained with respectively one of sequences SEQ ID NOs:11 to 39 or their complementary sequences.

A further subject of the present invention is an rpoB gene or gene fragment of a bacterium of the *Staphylococcus* genus, characterized in that it comprises a sequence such as described in sequences SEQ ID NOs:11 to 29 and 30 to 39.

A further subject of the present invention is the complete sequence of the rpoB gene of the bacteria *Staphylococcus saccharolyticus, Staphylococcus lugdunensis, Staphylococcus caprae* and *Staphylococcus intermedius* such as described in sequences SEQ ID NOs:3 to 6, as mentioned previously these fragments of rpoB genes and complete genes can be used in particular for a method according to the invention.

The complete sequence of the rpoB gene may be used to identify the bacterium not only by studying its primary sequence, but also by examining the secondary and tertiary structures of the messenger RNA derived from the transcription of the complete DNA sequence.

A further subject of the present invention is a said rpoB gene fragment or oligonucleotide chosen from among the oligonucleotides having a sequence included in sequences SEQ ID NOs:11 to 39 and among the oligonucleotides of reverse sequences and complementary sequences such as defined above.

A further subject of the present invention is an oligonucleotide comprising a sequence of at least 12, preferably 12 to 35 consecutive nucleotide patterns included in one of sequences SEQ ID NOs:7 to 10, in which N represents a nucleotide chosen from among inosine and an equimolar mixture of 4 different nucleotides chosen from among A, T, C or G, and the oligonucleotides of reverse sequences and complementary sequences, preferably consisting of sequences SEQ ID NOs:7 and 10 and the reverse sequences and complementary sequences in which N represents inosine.

Sequences SEQ ID NOs:7 to 39 may be prepared by chemical synthesis using techniques well known to persons skilled in the art, described for example in the article by Itakura K. et al [(1984) Annu. Rev. Biochem. 53:323].

A first application of an oligonucleotide of the invention is its use as probe for the detection, in a biological sample, of bacteria of one of the species of the *Staphylococcus* genus, which comprises a nucleotide sequence of at least 12 consecutive nucleotide patterns included in one of sequences SEQ ID NOs:7 to 39, and their reverse or complementary sequences.

A probe comprising sequences SEQ ID NOs:7 to 10 will be used as genus probe and a probe comprising one of sequences SEQ ID NOs:11 to 39 will be used as species probe.

The probes of the invention may be used, for diagnostic purposes as mentioned previously, by determining the formation or non-formation of a hybridization complex between the probe and a target nucleic acid in a sample, using all known hybridization techniques and in particular DOT-BLOT techniques [Maniatis et al. (1982) Molecular Cloning, Cold Spring Harbor], DNA transfer techniques called SOUTHERN BLOT [Southern E. M., J. Mol. Bio. (1975) 98:503] RNA transfer techniques called NORTHERN BLOT, or so-called "sandwich" techniques, in particular with a capture probe and/or detection probe, said probes being able to hybridize with two different regions of the target nucleic acid, and at least one of said probes (generally the detection probe) being able to hybridize with a region of the target which is specific to the species, the capture probe and the detection probe evidently having nucleotide sequences that are at least partly different.

The nucleic acid to be detected (target) may be DNA or RNA (the first obtained after PCR amplification). For detection of a target of double-strand nucleic acid type, the latter needs to be denatured before implementing the detection method.

The target nucleic acid may be obtained by extraction using known methods for examining nucleic acids in a sample. Denaturing a double strand nucleic acid may be conducted using known chemical, physical or enzymatic denaturing methods, in particular by heating to appropriate temperature, above 80° C.

To implement the above-mentioned hybridization techniques, in particular the "sandwich" techniques, a probe of the invention called a capture probe is immobilized on a solid carrier, and another probe of the invention called a detection probe is labeled with a marking agent. Examples of carriers and marking agents are as defined above.

Advantageously, a species probe is immobilized on a solid carrier, and another species probe is labeled with a marker.

A further application of an oligonucleotide of the invention is its use as nucleotide primer containing a monocatenary oligonucleotide chosen from among the oligonucleotides having a sequence of at least 12 nucleotide patterns included in one of sequences SEQ ID NOs:7 to 39, which can be used in the synthesis of a nucleic acid in the presence of a polymerase using a method known in itself, in particular in amplification methods using such synthesis in the presence of a polymerase (PCR, RT-PCR, etc.). In particular, a primer of the invention may be used for the specific reverse transcription of a messenger RNA sequence of a bacterium belonging to a species of the *Staphylococcus* genus to obtain a corresponding complementary DNA sequence. Said reverse transcription may form the first stage of the RT-PCR technique, the following stage being PCR amplification of the complementary DNA obtained. It is also possible to use primers of the invention for specific amplification by chain polymerization reaction of the total DNA sequence of the rpoB gene of a species of *Staphylococcus* genus.

In one particular case, said primer comprising an oligonucleotide of the invention also comprises the sense or antisense sequence of a promoter recognized by a RNA polymerase (promoters T7, T3, SP6 for example [Studier F W, B A Moffatt (1986), J. Mol. Biol. 189:113]: said primers can be used in nucleic acid amplification methods involving a transcription step, such as NASBA or 3SR techniques for example [Van Gemen B. et al. Abstract MA 1091, 7th International Conference on AIDS (1991) Florence, Italy].

A further subject of the invention is a nucleotide primer comprising a monocatenary oligonucleotide chosen from among the oligonucleotides having a sequence comprising one of sequences SEQ ID NOs:11 to 29 and 31 to 39, or preferably, consisting of one of sequences SEQ ID NOs:11 to 39 which can be used for total or partial sequencing of the rpoB gene of any strain of a species of the *Staphylococcus* genus.

Partial or full sequencing of the rpoB gene in any bacterium of the *Staphylococcus* genus enables the identification of any *Staphylococcus* bacterium through bio-computer analysis of this sequence and the recognition of new, unknown species of *Staphylococcus* bacteria.

Preferably, for use as primer or for sequencing rpoB genes, sequences SEQ ID NO: to SEQ ID NO: 0 are used, in which N is the choice inosine, sequences SEQ ID NO:7 and SEQ ID NO:10.

A further subject of the present invention is a diagnosis kit which can be used in a method of the invention, comprising at least one said gene fragment of said oligonucleotide consisting of sequences SEQ ID NOs:7 to 39 and the reverse sequences and complementary sequences, or a said oligonucleotide comprising a sequence included in one of sequences SEQ ID NOs:7 to 10, and/or at least one said rpoB gene fragment of a said bacterium comprising sequences SEQ ID NOs:11 to 39, and the oligonucleotides and gene fragments of reverse sequences and complementary sequences, such as defined above.

In the present description, by "reverse sequences and complementary sequences" is meant the following sequences:

the reverse sequence of said sequence, the complementary sequence of said sequence, and the complementary sequence of the reverse sequence of said sequence.

Finally, a last subject of the invention is a gene therapy probe to treat infections caused by a strain belonging to a species of the *Staphylococcus* genus, said probe comprising an oligonucleotide such as defined above. This gene therapy probe, able to hybridize on the messenger RNA and/or on the genomic DNA of said bacteria, can block phenomena of translation and/or transcription and/or replication.

The principle of gene therapy methods is known and is based especially on the use of a probe corresponding to an antisense strand; the formation of a hybrid between the probe and the sense strand is able to disturb at least one of the decoding steps of genetic information. Gene therapy probes can therefore be used as anti-bacterial medicines, to combat infections caused by bacteria of species of the *Staphylococcus* genus.

The invention will be better understood with the help of the description given below, divided into examples, which concerns experiments conducted to carry out the invention and which are given solely for illustrative purposes.

FIG. 1 shows visualization of the amplification products obtained in example 3 by ethidium bromide staining after electrophoresis on agarose gel.

EXAMPLE 1

Sequence of the rpoB Gene in Four Species of the *Staphylococcus* Genus: *Staphylococcus saccharolyticus, Staphylococcus lugdunensis, Staphylococcus caprae* and *Staphylococcus intermedius*

The complete sequence of the ropb gene of bacteria belonging to the species *Staphylococcus saccharolyticus, Staphylococcus lugdunensis, Staphylococcus caprae* and *Staphylococcus intermedius* was determined by enzymatic amplification and direct automatic sequencing using consensus primers between the sequences of the rpoB gene in *Staphylococcus aureus* (GenBank accession NO: X64172) *Bacillus subtillis* (GenBank accession NO: L43593). This latter bacterial species was chosen as being the Gram-positive species with low guanosine plus cytosine content the closest to species of the *Staphylococcus* genus (phylogenetic relationship based on comparison of sequences of the 16S rDNA gene).

Several potential consensus primers were investigated to obtain a fragment able to lead to the complete sequence of rpoB genes through successive elongations from a series of specific primers.

These consensus primers have the following sequences:

```
                                          (SEQ ID NO: 1)
5'-AAA CTT AAT AGA AAT TCA AAC TAA A-3'

5'-ATC TGG TAA AGC ATT ACC AA-3'         (SEQ ID NO: 2)
``` and made it possible to obtain a first fragment F1 having a length of 1 007 base pairs in these four species. From the alignment of the sequence of this first fragment F1 on the sequences of *Staphylococcus aureus* and *Bacillus subtilis*, a large number of attempts with theoretically or potentially appropriate primers failed, and finally a succession of oligonucleotide primers was able to be determined to permit amplification and sequencing in successive steps of the entirety of the rpoB gene in the four species *Staphylococcus saccharolyticus, Staphylococcus lugdunensis, Staphylococcus caprae* and *Staphylococcus intermedius*. The sequence, the position in relation to the sequence of the rpoB gene of *Staphylococcus aureus* in GenBank (access number X64172) and the hybridization temperature of these primers (SEQ ID NOs: 40-61, respectively) are given in the following table:

| Primer | Primer sequence (5'-3') | Position | Temp (° C.) |
|---|---|---|---|
| 30 F | GGTTTAGGATTAAAAGATGC (SEQ ID NO: 40) | 30-50 | 41 |
| 192 F | GAAGAAGTTGGAGCTACTG (SEQ ID NO: 41) | 192-211 | 44 |
| 806 F | AATAAGAGCAGGGAAAGAAAC (SEQ ID NO: 42) | 806-827 | 43 |
| 920 F | AAAGAAAAGAATGAATGAACTT (SEQ ID NO: 43) | 920-942 | 39 |

| Primer | Primer sequence (5'-3') | Position | Temp (° C.) |
|---|---|---|---|
| 1165 F | TATGCTTATGGTATTTAGCTA (SEQ ID NO: 44) | 1165-1186 | 39 |
| 1302 F | AAACTTAATAGAAATTCAAACTAAA (SEQ ID NO: 45) | 1302-1327 | 58 |
| 1450 F | GTTCAAACGATAAATAGAGAA (SEQ ID NO: 46) | 1450-1471 | 39 |
| 1741 F | GAAACAGATGCTAAAGATGT (SEQ ID NO: 47) | 1741-1761 | 41 |
| 1850 F | CCATATACTGCGAGTGGGAA (SEQ ID NO: 48) | 1850-1870 | 47 |
| 2245 F | TAGAAATTCAATCAATTAAGTATATG (SEQ ID NO: 49) | 2245-2271 | 62 |
| 2309 F | TTGGTAATGCTTTACCAGAT (SEQ ID NO: 50) | 2309-2329 | 41 |
| 2334 F | TGCATTACACCAGCAGATATCATTG (SEQ ID NO: 51) | 2334-2359 | 70 |
| 2412 F | GATGATATTGACCATTTAGG (SEQ ID NO: 52) | 2412-243 | 41 |
| 2534 F | TGAAAGAATGTCAATTCAAGA (SEQ ID NO: 53) | 2534-2555 | 39 |
| 2663 F | AAACCCATTAGCTGAGTT (SEQ ID NO: 54) | 2663-268 | 38 |
| 2995 F | TGGTCGTTTCATGGATGATGAAGTTG (SEQ ID NO: 55) | 2995-3119 | 74 |
| 2924 F | AAGATAGCTATGTTGTAGCA (SEQ ID NO: 56) | 2924-2944 | 41 |
| 3200 F | CTTAGAGAACGATGACTCTAA (SEQ ID NO: 57) | 3200-3221 | 43 |
| 3498 F | TAGTTGGTTTCATGACTTGGGA (SEQ ID NO: 58) | 3498-3520 | 46 |
| 3550 F | TTGAAAGTCCAACAAAGCAA (SEQ ID NO: 59) | 3550-3570 | 38 |
| 3843 F | GGTAAAGTAACGCCTAAAGGT (SEQ ID NO: 60) | 3843-3864 | 45 |
| 4494 F | TGGAGGTATGGGCACTTGAA (SEQ ID NO: 61) | 4494-4514 | 47 |
| 1759 R | ACATCTTTAGCATCTGTTTC (SEQ ID NO: 62) | 1779-1759 | 48 |
| 1460 R | ATCGTTTGAACGCCACTCTT (SEQ ID NO: 63) | 1480-1460 | 45 |
| 1910 R | TCATAGTAAGTTTGCGCCAT (SEQ ID NO: 64) | 1930-1910 | 43 |
| 2309 R | ATCTGGTAAAGCATTACCAA (SEQ ID NO: 65) | 2329-2309 | 41 |
| 2334 R | CAATGATATCTGCTGGTGTAATGCA (SEQ ID NO: 66) | 2354-2334 | 68 |
| 2432 R | CCTAAATGGTCAATATCATC (SEQ ID NO: 67) | 2452-2432 | 41 |
| 2573 R | CGAATATTAATTAATTGTTG (SEQ ID NO: 68) | 2593-2573 | 34 |
| 2892 R | GTGATAGCATGTGTATCTAAATCA (SEQ ID NO: 69) | 2912-2892 | 64 |
| 2915 R | TAACTATCTTCTTCATCAGC (SEQ ID NO: 70) | 2935-2915 | 41 |
| 2924 R | TGCTACAACATAGCTATCTT (SEQ ID NO: 71) | 2944-2924 | 41 |
| 2995 R | CAACTTCATCATCCATGAAACGACCA (SEQ ID NO: 72) | 3015-2995 | 74 |
| Cm32b | ATGCAACGTCAGGCCGTTCCG (SEQ ID NO: 73) | 3211-3191 | 64 |
| 3321 R | AGACGACGAACAGAATTTCA (SEQ ID NO: 74) | 3341-3321 | 56 |
| 3610 R | GCTCGAATGATAACGTGATT (SEQ ID NO: 75) | 3630-3610 | 43 |
| 4139 R | ACTTGTCCAATGTTCATACG (SEQ ID NO: 76) | 4159-4139 | 44 |
| 4502 R | CATATGCTTCAAGTGCCCATA (SEQ ID NO: 77) | 4523-4502 | 45 |
| 4508 R | CCAAGTGGTTGTTGTGTAAC (SEQ ID NO: 78) | 2428-4508 | 45 |
| 4871 R | TTTAGAGCTTTCACTGTTTG (SEQ ID NO: 79) | 4891-4871 | 41 |
| 5000 R | CACCATATGACCAAGAACGAA (SEQ ID NO: 80) | 5021-5000 | 45 |
| 5018 R | CAATCAAGGAGCCTACCTCCTT (SEQ ID NO: 81) | 5040-5018 | 50 |
| 5030 R | GAAATTATTTACATCAATCAA (SEQ ID NO: 82) | 5051-5030 | 36 |
| 5041 R | TAACTATCTTCTTCATCAGC (SEQ ID NO: 83) | 5061-5041 | 41 |
| 5085 R | CCCAGTCTTTTGTAGGTCCG (SEQ ID NO: 84) | 5105-5085 | 49 |
| 5188 R | CCCATTCTTTCACGACGTAC (SEQ ID NO: 85) | 5208-5188 | 47 |

The amplifications were performed under a final volume of 50 μl containing $2.5 \times 10^2$ U Taq polymerase, 1×Taq buffer and 1.8 mM $MgCl_2$, 200 μm dATP, dTTP, dGTP, dCTP and 0.2 μm of each primer. They were performed in accordance with the following program: 35 cycles comprising a denaturing step at 94° C. for 30 seconds, hybridization of the primers at 52° C. for 30 seconds and extension at 72° C. for 60 seconds. The amplification products were purified on a column then sequenced using the oligonucleotide sequencing primers (SEQ ID NOs: 62-85, respectively) listed in the following table:

The sequencing reactions were performed using reagents from the ABI Kit: Prism dRhodamine Dye Terminator Cycle Sequencing Ready Reaction Kit (Perkin Elmer Applied Biosystems) following the supplier's recommendations and the following program: 30 cycles comprising a denaturing step at 94° C. for 10 sec., a primer hybridization step at 50° C. for 10 sec., and an extension step at 60° C. for 2 minutes. The sequencing products were separated by electrophoresis on polyacrylamide gel using a 377 DNA Sequencer (Perkin) and analyzed to form consensus sequences with Sequence Assembler software (Applied Biosystems). This approach enabled us to determine the complete sequence of the rpoB gene in four species of the *Staphylococcus* genus:

SEQ ID NO:3: Sequence of the rpoB gene of *Staphylococcus saccharolyticus*. This sequence measures 3,791 base pairs, has a guanosine plus cytosine content of 36.8% and is deposited with GenBank under Genbank accession number AF325871.

```
5'ATGAAACTTAATAGAAATTCAAACTAAATCTTAT    (SEQ ID NO: 7)
GATTGGTTCCTTAAAGAAGGGTTATTAGAAATGTTT
AGAGACATTTCACCAATTGAAGATTTCACAGGCAAC
CTATCTTTAGAATTTGTAGATTATAGATTAGGTGAA
CCAAATTATGATTTAGAAGAATCTAAAAATCGTGAC
GCTACTTATGCTGCACCTCTTCGTGTCAAAGTACGT
CTCATTATTAAAGAAACAGGCGAAGTAAAAGAACAA
GAAGTCTTCATGGGTGATTTCCCATTAATGACAGAC
ACAGGTACATTTGTTATCAATGGTGCTGAGCGTGTT
ATCGTGTCTCAATTAGTACGTTCACCATCTGTTTAT
TTCAACGAAAAAATTGATAAAAACGGTCGTGAAAAT
TATGATGCGACTATTATTCCTAACCGTGGTGCTTGG
TTAGAATATGAAACAGATGCTAAAGATGTCGTTTAT
GTTCGTATCGATAGAACACGTAAATTACCATTAACT
GTATTGTTACGTGCGCTAGGTTTCTCAACTGATCAA
GAAATCGTTGATTTAATAGGAGACAGTGAATATTTA
CGTAATACATTAGAAAAAGATGGAACTGAAAATACA
GAACAAGCTTTATTAGAAATTTATGAACGTTTGCGT
CCTGGCGAACCACCAACAGTAGAAAATGCTAAAAGC
TTATTATATTCACGTTTCTTCGATCCTAAACGCTAT
GATTTAGCAAGTGTAGGTCGTTATAAAGCTAACAAA
AAGTTACATTTAAAACACCGTTTATTTAATCAAAAA
CTAGCAGAACCAATTGTTAATAGTGAAACAGGTGAG
ATTGTAGCGGAAGAAGGTACTGTACTTGATCGTCGT
AAACTAGATGAAATCATGGACGTATTGGAGACAAAC
GCTAATAGCGAAGTCTTTGAACTTGAAGGTAGTGTC
ATTGATGAACCAGTAGAAATTCAATCAATTAAAGTA
TATGTTCCTAATGATGAAGAAGGTCGAACTACTACT
GTTATTGGTAATGCATTACCAGACTCAGAAGTTAAA
TGTATTACTCCGGCTGATATTATCGCCTCAATGAGT
TACTTCTTTAACTTATTGAATGGAATTGGTTATACA
GATGATATTGACCACTTAGGTAATCGTCGTTTACGT
TCAGTTGGTGAATTACTACAAAACCAATTCCGTATC
GGTTT
GTCTAGAATGGAACGTGTTGTACGTGAGAGAATGTC    (SEQ ID NO: 9)
AATTCAAGACACTGATTCTATCACTCCACAACAATT
AATTAATATTCGTCCAGTCATTGCATCTATTAAAGA
ATTTTTTGGTAGTTCTCAATTATCTCAATTCATGGA
CCAAGC
                                        (SEQ ID NO: 10)
AAACCCATTAGCTGAGTTGACTCATAAACGTCGTTT
ATCAGCTCTAGGACCTGGTGGTTTAACTCGTGAACG
CGCTCAAATGGAAGTACGTGACGTGCATTATTCTCA
CTACGGTCGTATGTGCCCTATTGAAACACCTGAGGG
CCCAAACATTGGATTAATTAACTCATTATCTAGTTA
TGCAAGAGTAAATGAATTTGGTTTTATTGAAACACC
TTATCGTAAAGTTGATTTAGATACTAATTCAATCAC
TGACCAAATTGACTACTTAACTGCTGATGAAGAAGA
TAGTTATGTTGTTGCACAAGCAAACTCACGTCTTGA
TGAAAATGGGTGCTTCTTAGATGATGAAGTTGTTTG
TCGTTTTCGTGGCAATAACACAGTGATGGCTAAAGA
AAAAATGGACTATATGGACGTATCACCTAAACAAGT
AGTTTCAGCAGCTACTGCATGTATCCCATTCTTAGA
AAACGATGACTCAAACCGAGCATTAATGGGTGCAAA
CATGCAACGTCAAGCAGTACCATTAATGAACCCAGA
AGCGCCATTTGTTGGAACAGGTATGGAACATGTAGC
AGCGCGTGACTCAGGTGCAGCAATTACTGCTAAGCA    (SEQ ID NO: 8)
TAGAGGACGTGTTGAACATGTTGAGTCTAATGAAGT
TTTAGTTCGTCGTTTAGTAGAAGAAAATGGTATTGA
ACATGAAGGTGAATTAGATCGCTATCCATTAGCAAA
ATTCAAACGTTCAAACTCTGGTACATGTTATAACCA
ACGCCCAATTGTTTCTGTTGGAGACGTTGTTGAATA
TAACGAAATTTTAGCAGACGGTCCTTCAATGGAACT
AGGTGAAATGGCTTTAGGTCGTAACGTAGTTGTAGG
TTTCATGACTTGGGACGG
                                        (SEQ ID NO: 30)
TTATAACTATGAGGATGCCGTTATCATGAGCGAACG
TTTAGTTAAAGATGATGTCTATACATCTATTCATAT
CGAAGAATACGAATCAGAAGCACGTGACACTAAATT
AGGACCTGAAGAAATTACTCGTGATATTCCTAATGT
GTCTGAAAGTGCGCTTAAAAACTTAGACGATCGTGG
TATCGTTTATGTTGGTGCCGAAGTTAAAGATGGTGA
```

-continued

CATCTTAGTAGGCAAAGTAACGCCTAAAGGTGTAAC

GGAACTAACAGCAGAAGAAAGATTATTACATGCTAT

TTTCGGTGAAAAGGCTCGTGAAGTTCGTGATACTTC

ATTACGTGTACCACATGGTGCAGGGGGCATCGTATT

AGATGTAAAAGTCTTCAACCGTGAAGAGGGCGATGA

CACTTTATCTCCTGGTGTAAATCAATTAGTACGTGT

TTATATCGTTCAAAAACGTAAAATTCATGTAGGGGA

TAAAATGTGCGGTCGTCATGGTAATAAAGGTGTTAT

TTCTAAAATTGTTCCTGAAGAAGATATGCCATACTT

ACCTGATGGTCGACCAATCGACATCATGTTAAATCC

ACTTGGTGTACCTTCACGTATGAACATTGGACAAGT

GCTAGAATTACACTTAGGTATGGCTGCTAAAAACTT

AGGCATCCACATTGCATCACCAGTATTTGATGGTGC

TAATGATGATGATGTTTGGTCTACAATCGAAGAGGC

CGGCATGGCACGTGATGGTAAGACTGTATTATATGA

TGGGCGTACGGGTGAACCGTTTGATAACCGTATTTC

TGTAGGTGTAATGTACATGCTTAAACTTGCTCACAT

GGTTGATGACAAATTGCATGCACGTTCAACAGGACC

ATACTCACTCGTTACACAACAACCACTCGGTGGTAA

AGCACAATTTGGTGGACAACGTTTCGGTGAGATGGA

GGTATGGGCACTTGAAGCATATGGTGCTGCTTATAC

TTTACAAGAAATCTTAACTTATAAATCTGACGATAC

AGTAGGACGTGTTAAAACTTACGAATCTATCGTTAA

AGGTGAAAACATCTCTAGACCAAGTGTTCCTGAGTC

ATTCCGAGTACTGATGAAAGAATTACAAAGTTTAGG

ATTAGATGTTAAAGTAATGGATGAGCATGATAATGA

AATTGAAATGGCAGATGTTGATGATGAAGATGCAAC

GGAACGCAAAGTAGATTTACAACAAAAAAATGCTCC

GGAATCACAAAAAGAAACAACTGATTAATAAGCACT

TAAGATAAATGAATACTTAAAGGGTATGAAATGATT

ATCATTTCAACTTCTTTAGGTATTCGATTTCAATGA

AAGTAATCAATCAAATAGCACAGCTAATCTAAATTG

AAGGAGGTAGGCTCCTTGATTGATGTAAATAATTTC

CATTATATGAAAATAGGATTAGCTTCACCTGAAAAG

ATTCGTTCTTGGTCATATGGTGAAGTTAAGAAACCT

GAAACAATAAACTATCGTACTTTAAAGCCAGAAAAA

GATGGTCTTTTCTGTGAAAGAATTTTCGGACCTACA

AAAGACTGGGAAATTTTTAA-3'

SEQ ID NO:4: Sequence of the rpoB gene of *Staphylococcus lugdunensis*. This sequence measures 3 855 base pairs, has a guanosine plus cytosine content of 36.4% and is deposited with GenBank under Genbank under accession number AF325870.

5'ATGTCTTATGATTGGTTCCTAAAAGAAGGTTTAC    (SEQ ID NO: 7)

TAGAAATGTTCCGTGATATCTCACCAATTGAAGATT

TCACAGGTAACCTATCATTAGAGTTTGTAGATACAG

ATTAGGTGAACCAAAGTATGATTTAGAAGAATCGAA

AAATCGTGACGCTACTTATGCTGCACCTCTTCGTGT

TAAAGTGCGTCTCGTTATAAAAGAAACAGGTGAAGT

TAAAGAGCAAGAAGTATTTATGGGAGACTTCCCATT

AATGACAGATACAGGTACGTTTGTTATTAATGGTGC

AGAGCGTGTTATTGTATCGCAATTAGTACGTTCACC

ATCCGTTTACTTTAATGAAAAAATTGACAAAAACGG

ACGAGAAAATTATGATGCTACAATCATTCCTAACCG

TGGTGCCTGGTTAGAATACGAAACAGATGCTAAAGA

TGTTGTCTATGTTCGTATTGATAGAACTCGTAAATT

GCCATTAACTGTCTTATTACGCGCATTAGGCTTTTC

AACTGATCAAGAAATTGTTGAGTTGTTAGGCGATAA

CGAATACTTGCGTAATACATTAGAAAAAGACGGAAC

AGAAAACACTGAACAAGCGTTATTAGAAATTTATGA

ACGTTTACGTCCTGGTGAACCACCAACAGTTGAAAA

TGCAAAAGTTTATTATATTCTCGCTTCTTCGATCC

GAAACGCTATGATTTAGCAAGCGTTGGACGTTATAA

AGCGAACAAAAAATTGCATCTAAAACACCGTTTATT

TAATCAAAAATTAGCAGAGCCTATCGTAAACAGCGA

AACAGGTGAAATTGTTGCTGAAGAAGGTACTGTATT

AGATCGTCGCAAATTAGACGAAATTATGGACGTTCT

TGAAACAAATGCGAATAGTGAAGTATTCGAATTAGA

AGGAACAGTAATAGACGAACCGGTTGAAATTCAATC

AATCAAAGTCTATGTACCAAATGATGAAGAAGGTTG

TACAACAACGATAATTGGTAATGCTTTACCAGATTC

AGAAGTGAAATGTATCACACCTGCAGATATTATTTC

TTCTATGAGTTACTTCTTCAACTTATTAGCTGGCAT

TGGTTACACGGATGATATCGATCATTTAGGTAACCG

TCGTTTACGTTCAGTTGGTGAGTTATTGCAAAACCA

ATTCCGTATTGGTTT

ATCAAGAATGGAACGTGTTGTGCGTGAAAGAATGTC    (SEQ ID NO: 9)

AATTCAAGATACCGAATCTATCACACCAACAATT

AATTAATATTAGACCAGTTATTGCATCAATTAAAGA

ATTCTTTGGTAGTTCTCAATTATCA<u>CAATTCATGGA</u>

-continued

CCAAGC (SEQ ID NO: 10)

TAACCCATTAGCAGAATTAACACACAAACGTCGTTT
ATCTGCGTTAGGACCTGGTGGTTTAACACGTGAACG
TGCACAAATGGAAGTTCGTGACGTGCATTATTCTCA
CTATGGCCGTATGTGTCCGATTGAAACACCAGAGGG
TCCAAACATTGGTTTGATTAACTCATTATCTAGTTA
TGCGCGTGTCAACGAGTTTGGCTTATTGAAACGCC
TTATCGTAAAGTAGATATTGATACAAATGCAATCAC
AGATCAAATTGACTACTTAACTGCTGATGAAGAAGA
CAGTTATGTCGTTGCACAAGCGAACTCTCGCCTTGA
TGAAAATGGTCGTTTCTTAGATGATGAAGTAGTATG
CCGTTTCCGCGGTAATAATACTGTTATGGCTAAAGA
AAAAATGGACTACATGGATGTATCTCCTAAACAAGT
TGTTTCAGCTGCGACAGCATGTATTCCATTCTTAGA
GAACGATGACTCTAACCGTGCATTGATGGGTGCAAA
CATGCAACGTCAAGCAGTTCCGTTGATGAACCCTGA
AGCGCCGTTCGTAGGAACAGGTATGGAGCATGTTGC
TGCTCGTGACTCTGGTGCTGCGATTACTGCAAAATA (SEQ ID NO: 8)
CAGAGGTCGTGTAGAACACGTTGAATCTAATGAAAT
CCTAGTGCGTCGATTAATTGAAGAAAATGGAAAAGA
ATATGAAGGCGAACTTGATCGCTATCCATTAGCGAA
GTTTAAACGCTCTAACTCTGGTACATGTTATAACCA
ACGTCCAATTGTTTCTATTGGCGACGTTGTAGAATA
CAATGAAATTCTAGCTGACGGTCCATCAATGGAGCT
TGGTGAAATGGCATTAGGCCGCAACGTTGTAGTTGG
TTTCATGACTTGGGACGG

CTATAACTATGAAGATGCTGTCATCATGAGTGAACG (SEQ ID NO: 4)
TTTAGTCAAAGATGACGTTTACACATCTATTCATAT
TGAAGAATATGAATCAGAAGCACGTGATACGAAATT
AGGACCTGAGGAAATCACACGTGATATTCCTAACGT
CTCTGAAAGTGCACTTAAAAACTTAGACGATCGCGG
TATTGTTTATGTAGGTGCAGAAGTTAAAGATGGCGA
TATTTTAGTAGGTAAAGTAACGCCTAAAGGTGTCAC
AGAGCTAACAGCTGAAGAACGTCTATTACATGCAAT
CTTTGGTGAAAAAGCACGTGAAGTGCGTGACACTTC
ATTGCGTGTACCACATGGTGCTGGCGGTATTGTGCT
AGATGTTAAAGTCTTCAACCGTGAAGAGGAGATGA
CACACTTTCTCCAGGTGTTAACCAATTAGTACGCGT
ATATATTGTGCAGAAACGTAAAATACACGTTGGGGA

-continued

CAAAATGTGTGGTCGTCATGGTAACAAAGGTGTCAT
TTCTAAGATTGTTCCAGAAGAGGACATGCCTTATTT
ACCAGATGGACGTCCAATTGATATTATGTTAAACCC
ACTTGGTGTGCCATCACGTATGAACATTGGACAAGT
TCTAGAGTTGCATTTAGGTATGGCTGCTAAAAACTT
AGGTATTCATGTTGCGTCACCAGTATTTGATGGTGC
GAACGATGAAGATGTATGGTCAACAATTGAAGAAGC
TGGTATGGCACGTGACGGTAAAACCGTATTATATGA
TGGCCGTACAGGTGAGCCATTCGACAACCGTATCTC
AGTTGGAGTTATGTACATGCTTAAACTTGCACATAT
GGTTGATGACAAATTACATGCTCGTTCAACAGGTCC
ATACTCATTAGTTACACAACAACCACTTGGTGGTAA
AGCACAATTTGGTGGACAACGTTTCGGTGAGATGGA
AGTATGGGCACTTGAAGCTTATGGTGCTGCCTATAC
ATTGCAAGAAATCCTTACTTATAAATCTGATGATAC
GGTAGGCCGTGTTAAAACATACGAAGCTATCGTTAA
AGGTGAAAACATTTCTAGACCAAGTGTTCCTGAATC
ATTCCGTGTATTGATGAAAGAACTTCAAAGTTTAGG
TTTAGATGTGAAAGTGATGGATGAGCACGATAACGA
AATCGAAATGGCAGATGTTGAAGATGAAGATACAAC
AGAGCGCAAAGTAGATTTGCAACAAAAAGATGCGCC
ACAATCTCAACAAGAAGAAACTGCTGATTAGTCAAT
ATATTAGATATAAGGAATGGTGTTAGGAACAAGTGC
TACGGATGTTTAAACATAATGTGTTTTGAGTTGCAT
CCATCCTAACCTTTCCTTAATTTCAATAGATGTAAA
TCAATCAAATGGCACAGCTAATCTAAATTGAAGGAG
GTAGGCTCCTTGATTGATGTAAATAATTTCCATTAT
ATGAAAATCGGTTTAGCCTCACCTGAAAAAATTCGT
TCATGGTCATATGGTGAAGTGAAAAAACCAGAAACA
ATTAATTATCGTACGTTAAAACCAGAAAAAGATGGC
TTATTCTGTGAGAGAATATTCGGCCCAACTAAAGAT
TGGGAATGTAGTTGTGGTAAATACAAACGTGTGCGT
TATAAAGGCATGGTTTGTGATAGATGTGGTGTTGT
AA-3'

SEQ ID NO:5: Sequence of the rpoB gene of *Staphylococcus caprae*. This sequence measures 3 698 base pairs, has a guanosine plus cytosine content of 37.4% and is deposited with GenBank under Genbank under accession number AF325868.

5'ATGAAACTTAATAGAAATTCAAACTAAATCTTAC (SEQ ID NO: 7)
GATTGGTCCTTAAAGAAGGTTTATTAGAAATGTTTA

-continued

GAGACATTTCTCCAATTGAAGATTTCACAGGTAACC

TATCTTTAGAATTTGTAGATTATAGATTAGGTGATC

CGAAATACGATTTAGAAGAATCTAAAAACCGTGACG

CTACTTATGCTGCACCTCTTCGTGTGAAAGTACGTC

TCATTATTAAAGAAACAGGCGAAGTGAAGGAACAAG

AAGTCTTCATGGGTGATTTCCCATTAATGACTGACA

CAGGTACATTCGTTATCAATGGTGCTGAACGTGTTA

TCGTTTCTCAATTAGTACGTTCACCATCCGTTTATT

TCAACGAGAAAATTGATAAAAATGGACGCGAAAACT

ACGATGCAACTATCATTCCTAACCGTGGTGCTTGGT

TAGAATATGAAACAGATGCGAAAGATGTAGTATACG

TTCGTATCGATAGAACTCGTAAATTACCATTGACAG

TATTATTACGTGCACTAGATTTCTCAACTGATCAAG

AAATTGTTGATTTACTAGGTGAGAGTGAATATTTAC

GTAATACATTAGAAAAGATGGTACTGAAAATACTG

AACAAGCATTATTAGAAATTTATGAACGTTTACGTC

CTGGCGAACCACCAACAGTTGAAAATGCTAAAAGCT

TATTATACTCACGCTTCTTCGACCCTAAACGTTATG

ATTTAGCAAGTGTTGGTCGTTACAAAGCTAACAAAA

AGTTACATTTAAAACACCGTTTATTTAATCAAAAAT

TAGCAGAACCTATTGTTAATAGTGAAACAGGTGAGA

TTGTAGCTGAAGAAGGTACTGTATTAGATCGTCGTA

AAATTGACGAAATCATGGACGTTTTAGAAACAAACG

CTAACAGTGAAGTTTTCGAATTAGAAGGTAGCGTTA

TTGACGAACCTGTTGAAATTCAATCAATTAAAGTCT

ATGTACCTAATGATGAAGAAGGTCGCACAACTACTG

TAATTGGTAATGCATTACCAGATTCAGAAGTTAAAT

GTATTACTCCAGCTGATATCATTGCGTCAATGAGTT

ATTTCTTCAACTTATTAAATGGTATTGGTTATACAG

ATGATATCGACCACTTAGGTAACCGTCGTTTACGTT

CAGTTGGTGAACTTTTACAG<u>AACCAATTCCGTATCG</u>

<u>GTTT</u>

ATCAAGAATGGAACGTGTTGTTCGTGAAAGAATGTC (SEQ ID NO: 9)

TATTCAAGACACTGATTCAATCACACCACAACAATT

AATCAACATTCGTCCGGTTATTGCGTCTATTAAAGA

ATTCTTCGGAAGTTCACAATTATCG<u>CAATTCATGGA</u>

<u>CCAAGC</u>

(SEQ ID NO: 10)

TAACCCATTAGCTGAGTTGACTCATAAACGTCGTCT

ATCAGCATTAGGACCTGGTGGTTTAACGCGTGAACG

-continued

TGCCCAAATGGAAGTGCGTGACGTTCACTATTCTCA

CTATGGCCGTATGTGTCCAATCGAAACACCTGAGGG

ACCAAACATTGGTTTAATCAACTCATTATCAAGTTA

TGCACGAGTAAATGAATTTGGTTTTATTGAAACACC

TTATCGTAAAGTAGATTTAGATACGAATTCTATCAC

TGACCAAATTGATTACTTAACTGCTGATGAAGAAGA

TAGTTATGTTGTTGCCCAAGCGAACTCTCGTTTAGA

CGAAATGGTCGTTTCTTAGATGACGAAGTTGTTTG

TCGTTTCCGTGGTAATAACACAGTTATGGCTAAAGA

GAAAATGGACTACATGGATGTATCTCCTAAACAAGT

AGTATCTGCAGCGACAGCTTGTATTCCATTCTTAGA

AAATGATGACTCTAACCGTGCATTAATGGGTGCGAA

CATGCAACGTCAAGCAGTACCATTGATGAATCCAGA

AGCGCCATTTGTTGGT<u>ACAGGTATGGAACATGTAGC</u>

CGCACGTGATTCAGGTGCAGCGATTACTGCTAAACA (SEQ ID NO: 8)

TAGAGGACGCGTTGAACACGTTGAATCTAACGAAGT

ATTAGTACGTCGTTTAGTAGAAGAAACGGCACTGA

ACATGAAGGTGAATTAGATCGTTACCCATTAGCTAA

ATTCAAACGTTCAAACTCTGGTACATGTTATAACCA

ACGTCCAATGTTTCTGTTGGTGATGTAGTAGAATAC

AATGAAATTTTAGCTGACGGTCCTTCAATGGAATTA

AGGTTGAAATGGCATAGGGACGTAACGTTGTTAGTT

<u>GGTTTCATGACTTGGGACGG</u>

TTATAACTACGAGGATGCTGTTATCATGAGTGAACG (SEQ ID NO: 5)

TTTAGTTAAAGATGACGTTTATACTTCTATTCACAT

TGAAGAATATGAATCTGAAGCTCGTGATACTAAGTT

AGGACCTGAAGAAATTACTCGTGACATTCCTAACGT

ATCTGAAAGTGCACTTAAAAACTTAGACGATCGCGG

TATCGTTTATGTTGGTGCTGAAGTTAAAGACGGTGA

CATCTTAGTAGGTAAAGTAACGCCTAAAGGTGTAAC

TGAATTAACAGCTGAAGAAGATTATTACATGCTAT

CTTCGGTGAAAAGGCTCGTGAAGTCCGCGATACATC

ATTACGTGTACCACATGGTGCAGGCGGTATCGTTCT

AGATGTTAAAGTATTCAATCGTGAAGAAGGCGATGA

TACGTTATCTCCAGGTGTAAACCAATTGGTACGTGT

TTATATCGTTCAAAAACGTAAAATTCATGTAGGGGA

CAAAATGTGTGGTCGTCACGGTAACAAAGGTGTTAT

CTCTAAAATTGTTCCTGAAGAAGATATGCCATACTT

ACCAGATGGTCGTCCAATCGACATCATGTTAAACCC

ACTTGGTGTACCATCACGTATGAACATCGGACAAGT

```
ACTTGAGTTGCATTTAGGTATGGCTGCTAAGAACTT
AGGCATCCATGTAGCATCTCCAGTATTCGATGGTGC
AAACGATGATGATGTATGGTCAACAATTGAAGAAGC
AGGTATGGCTCGTGATGGTAAAACTGTATTATACGA
TGGACGTACAGGTGAACCATTCGATAACCGTATTTC
TGTAGGTGTCATGTACATGCTTAAACTTGCTCACAT
GGTTGACGATAAATTACACGCACGTTCAACTGGACC
ATACTCACTTGTTACACAACAACCACTTGGTGGTAA
AGCACAATTCGGTGGTCAACGCTTCGGTGAGATGGA
GGTATGGGCACTTGAAGCATATGGTGCTGCATACAC
ATTACAAGAAATCTTAACTTATAAATCTGACGATAC
AGTAGGTCGTGTTAAAACTTACGAATCTATCGTTAA
AGGTGAAAATATCTCTAGACCAAGTGTTCCAGAATC
ATTCAGAGTATTGATGAAGAATTACAAAGTTTAGG
ATTAGATGTTAAAGTGATGGACGAGCAAGACAACGA
AATTGAAATGGCGGACGTTGATGATGAAGATGCAAC
TGAACGCAAAGTAGATTTACAACAAAAAAATGCTCC
CGAATCACAAAAAGAAACAACTGATTAATAAGCACT
TAAGATAAATGAATCCTAAAGAGGTTATGAGATGGT
TGCCATTTCAACCTCTTTAAGGTATTCGATTTCAAT
GAATGTAAATCAATCAAATAGCACAGCTAATCTAAA
TTGAAGGAGGTAGGCTCCTTGATTGATGTAAATAAT
TTCCATTATATGAAAATAGGATTAGCTTCACCTGAA
AAAATTCGTTCTTGGTCTTATGGTGAAGTTAA-3'
```

SEQ ID NO:6: Sequence of the rpoB gene of *Staphylococcus intermedius*. This sequence measures 3 851 base pairs, has a guanosine plus cytosine content of 39.2% and is deposited with GenBank under Genbank accession number AF325869.

```
5'ATGTAAACTTAATAGAAATTCMAACTAAATCGTA    (SEQ ID NO: 7)
TGATTGGTTCTTAAAAGAAGGTTTATTAGAAATGTT
CCGTGATATTTCTCCTATTGAAGACTTCACGGGTAA
TCTTTCATTAGAATTTGTTGATTATAGATTAGGTGA
ACCAAAGTATGATTTAGAAGAATCAAAAAACCGTGA
TGCAACATACGCGGCACCATTACGTGTGAAAGTTCG
TTTAATCATTAAAGAAACAGGCGAAGTGAAAGATCA
AGAAGTATTTATGGGTGATTTCCCATTAATGACAGA
AACAGGTACTTTTGTGATTAACGGGGCAGAACGTGT
TATCGTATCACAATTAGTCCGTTCACCATCTGTATA
CTTCAATGAAAAATTAGATAAAAACGGATGCGTGAA
TTATGATGCGACAGTCATTCCTAACCGTGGTGCTTG
GTTGGAATATGAAACAGATGCGAAAGATGTCGTTTA
TGTGCGTATCGATAGAACGAGAAAGTTACCATTAAC
AGTATTATTACGTGCGTTAGGTTATTCAACAGACCA
AGAAATTATTGAATTAATTGGGGATAATGAATATTT
ACGTAATACATTAGAAAAAGATAGCACAGAAAATAC
AGAGCAAGCATTACTTGAAATTTATGAACGTTTACG
TCCAGGTGAACCACCTACTGTAGAAAACGCAAAAAG
CTTATTATACTCACGTTTCTTTGACCCTAAACGTTA
TGATTTAGCAAGCGTTGGACGTTATAAAGCAAACAA
AAAGTTACATTTAAAACACCGCCTATCAATCAAAA
ATTAGCTGAACCGATCGTTAATACTGAAACAGGCGA
AATTGTTGCTGAAGAAGGCACTGTTTTAGATCGTCG
TAAATTAGATGAAATTATGGACGTTCTTGAAACAAA
TGCGAATGCACAAGTTTATGAACATTCCAAACGGAT
CATTGATGAGCCAGTAGAAATTCAATCAATTAAAGT
ATATGTACCGAATGATGATGAAGAACGTACAACAAC
AGTTATTGGTAATGCATTCCCAGATTCAGAAGTGAA
ATGTATTACACCGGCTGATATTGTGGCATCTATGTC
ATACTTCTTCAACCTATTACATGGTATTGGTTACAC
AGACGATATTGACCACCTTGGTAACCGCCGTCTACG
TTCAGTTGGTGAGTTGTTACAAAACCAATTCCGTAT
CGGTTT
ATCAAGAATGGAACGTGTGGTACGTGAAAGAATGTC    (SEQ ID NO: 9)
TATTCAAGATACAGACTCTATCACACCGCAACAATT
AATTAATATTCGTCCAGTGATTGCATCAATTAAAGA
GTTCTTTGGTAGCTCGCAATTATCTCAATTCATGGA
CCAAGC
                                     (SEQ ID NO: 10)
GAACCCACTTGCTGAGTTGACTCACAAACGTCGTCT
ATCAGCATTAGGACCTGGTGGTTTAACGCGTGAACG
TGCTCAAATGGAAGTGCGTGACGTACACTACTCTCA
CTATGGTCGTATGTGTCCAATCGAAACACCTGAGGG
ACCAAACATTGTTTGATCAACTCATTATCTAGTTA
TGCACGTGTGAACGAATTTGGTTTTATCGAAACACC
ATATCGTAAAGTTGATATTGAAACAAATACGATTAC
TGACCAAATCGACTACTTAACTGCTGATGAAGAAGA
TAGTTATGTTGTCGCACAAGCGAACTCACGTCTTGA
TGAAAACGGTCGCTTTATTGATGATGAGATTGTATG
TCGTTTCCGTGGTAACAACACAACGATGGCGAAAGA
AAAAATGGACTACATGGACGTATCGCCGAAACAAGT
```

-continued
TGTATCAGCTGCGACAGCGTGTATCCCATTCTTAGA

AAACGATGACTCTAACCGTGCGTTAATGGGTGCGAA

CATGCAGCGTCAAGCGGTACCGTTGTTAAACCCTGA

ATCTCCATTTGTAGGT<u>ACAGGTATGGAACACGTTGC</u>

<u>TGCACGTGACTCAGGTGCTGCTGTCATTTCTAAATA</u> (SEQ ID NO: 8)

TCGCGGTCGTGTTGAACATGTCCAATCTAGCGAGAT

TTTAGTCCGTCGTTTAGTTGAAGAAAACGGTCAAGA

AGTAGATGGTACGTTAGATCGTTATCCATTAGCGAA

ATTTAAACGTTCGAACTCAGGTACATGTTATAACCA

ACGTCCAATCATCGCAAAAGGTGACATTGTGGAAAA

AGGCGAAATCCTTGCTGATGGTCCTTCAATGGAACT

TGGTGAAATGGCATTAGGTCAGAAACGTAGTAGTT<u>G</u>

<u>GTTCATGACTTGGGACGG</u>

TTATAACTATGAGGATGCCGTTATCATGAGTGAACG (SEQ ID NO: 6)

TTTGGTTAAAGATGATGTGTACACGTCTATTCATAT

TGAAGAATACGAATCAGAAGCGCGTGACACAAAACT

TGGACCTGAAGAAATCACACGTGATATTCCTAACGT

ATCTGAAAATGCACTGAAAAACTTAGATGATCGCGG

TATCGTTTATGTAGGTGCGGAAGTTAAAGACGGCGA

CATCTTAGTGGGTAAAGTAACGCCAAAAGGTGTAAC

AGAATTAACTGCAGAAGAACGTTTATTACATGCAAT

CTTTGGTGAAAAGCACGTGAAGTACGTGATACATC

ATTACGTGTACCTCACGGCGCGGGCGGTATTGTACT

TGATGTTAAAGTGTTCAATCGTGAAGAAGGCGATGA

TTCACTTTCACCAGGTGTGAACCAACTCGTACGTGT

TTACATTGTTCAAAAACGTAAAATTCATGTAGGGGA

CAAAATGTGTGGTCGTCACGGTAACAAAGGTGTCAT

CTCTAAAATTGTTCCTGAAGAAGACATGCCGTACTT

ACCAGACGGTCGTCCAATCGACATCATGTTGAACCC

ACTCGGTGTACCATCTCGTATGAACATCGGACAAGT

TTTAGAGCTCCACTTAGGTATGGCAGCTAAAAACTT

AGGTATCCACGTTGCATCACCAGTATTCGATGGTGC

GAACGATGATGACGTATGGTCTACAATTGAAGAAGC

AGGTATGGCACGTGATGGTAAAACTGTCCTTTACGA

TGGACGTACAGGTGAACCATTCGACAACCGTATCTC

TGTAGGTGTCATGTACATGCTGAAACTTGCACACAT

GGTTGATGACAAGCTTCACGCACGTTCTACAGGACC

TTACTCACTTGTTACACAACAACCGCTTGGTGGTAA

AGCACAGTTTGGTGGACAAAGATTTGGTGAGATGGA

GGTATGGGCACTTGAAGCATACGGTGCAGCATACAC

-continued
ATTACAAGAAATCCTCACATACAAATCAGATGACAC

AGTAGGTCGTGTGAAAACTTACGAAGCTATCGTTAA

AGGTGAAAACATCTCAAGACCAAGTGTTCCTGAATC

ATTCCGCGTATTGATGAAAGAATTACAAAGTTTAGG

TCTTGACGTTAAAGTGATGGACGAACAAGATAACGA

AATTGAAATGCGTGACTTAGACGATGATGATATTCC

AGATCGCAAAGTCAACATTCAACCATCAACTGTTCC

TGAATCACAAAAAGAATTTAACGAATAATGATGAAT

TGTAGATAAGATTAAACGGAATAGAAACACTTGGTT

AAGCTTGAGTTTGTGTTCAAATGTGACAGTTGAAAT

ACAACAGATGTCATGTACGATTAATCTATTCGGAAA

TGTGATCGGAATCCAACGAGAGGGCTTGGGTTTCGA

TGCATATCCGATACTGCAACATTTTTAAGATAAATT

GTAAATCAATCAACTAGCACAGTTAATTTAAACTAA

AGGAGGTAGGCTCCTTGATTGATGTAAATAAATTCC

ATTACATGAAAATAGGACTCGCTTCACCTGAAAAAA

TTCGTTCTTGGTCATATGGTGAGGTCAAAAGCCAG

AAACAATTAACTACCGTACGTTAAAACCAGAAAAAG

ATGGTAA-3'

This sequence measures 3 852 base pairs, has a guanosine plus cytosine content of 39.2% and is deposited with Genbank under accession n° AF325869.

EXAMPLE 2

Partial Sequencing of the rpoB Gene of 26 Species of the *Staphylococcus* Genus

The alignment of the rpoB sequence determined in bacteria of the species *Staphylococcus aureus, Staphylococcus lugdunensis* (GenBank accession AF325870), *Staphylococcus intermedius* (GenBank accession AF325869), *Staphylococcus saccharolyticus* (GenBank accession AF325871) and *Staphylococcus caprae* (GenBank accession AF325868) permitted the determination of the consensus sequences of the following oligonucleotides respectively positioned at position 2491-2511 and 3554-357 of the rpoB gene in *Staphylococcus aureus*:

SEQ ID NO:7: 5'-AACCAATTCCGTATNGGTTT-3' (where N represents inosine).

SEQ ID NO:8: 5'-CCGTCCCAAGTCATGAAAC-3' theoretically determining the amplification of a fragment of 1 063 base pairs in all species of the *Staphylococcus* genus.

SEQ ID NO:8 is used as 3' primer and therefore represents the complementary reverse sequence of the direct strand represented in sequences SEQ ID NOs:3 to 6 at position 3554-3573 in *Staphylococcus aureus*.

The inventors have determined the position of these two primers SEQ ID NO:7 and SEQ ID NO:8 paying heed to the following criteria:

1. sequence flanked by these two primers specific to the species of the bacterium. This condition is verified after alignment of 1063 bp fragments with all the sequences of the rpoB bacterial genes available in computer data banks.

2—search for the shortest possible identification region so as to increase the sensitivity of molecular detection as much as possible, 3—search for a region close to the one previously worked by inventors in the area of enterobacteria [Mollet C. (1997) Mol. Microbiol., 26:1005-11] so as to tend towards a working area common to these two bacterial genus and family.

4—primer length of 18 to 22 bp,

5—primer sequences having close melting points

6—primer sequence not permitting self-hybridization or complementarity.

In silico analysis predicted that these two oligonucleotides SEQ ID NO:7 and SEQ ID NO:8 should enable PCR amplification of a fragment of 1 063 base pairs of the rpoB gene in all species of the *Staphylococcus* genus. In reality, the primer of sequence SEQ ID NO:8 did not adhere to a rare species for undetermined reasons. Laboratory experiments showed that the species of the genus: *Staphylococcus schleiferi* was not amplified by this pair of oligonucleotide primers, demonstrating the uncertain nature of predictions made on primers. The inventors therefore, by trial and error, determined a new oligonucleotide of sequence SEQ ID NO:10 positioned at position 3241-3261 in *Staphylococcus aureus* which, combined with the SEQ ID NO:7 oligonucleotide in a PCR amplification reaction, effectively enabled the obtaining of an amplicon of the rpoB gene having a size of 771 base pairs (size for the reference species *Staphylococcus aureus*) in 29 species of the *Staphylococcus* genus tested by the inventors:

SEQ ID NO:10: 5'GCIACITGITCCATACCTGT-3' (where n=inosine)

SEQ ID NO:10 is used as 3' primer. This is why it corresponds to the complementary reverse sequence of the sequences of the direct strand represented on sequences SEQ ID NOs:3 to 6.

This amplification product is then sequenced by incorporating two sequencing primers, SEQ ID NO:9 (located at position 2643-2660 of the rpoB gene in bacteria of the species *Staphylococcus aureus*) and SEQ ID NO:10.

SEQ ID NO:9: 5'-CAA TTC ATG GAC CAA GC-3'.

This last primer was determined to pay heed to the constraints of a sequencing primer, i.e. a size of more than 15 mothers, not hybridizing with the second primer used for sequencing, and flanking a zone of approximately 500 base pairs in general whose sequence is specific to each species in the *Staphylococcus* genus.

By using this second set of oligonucleotides of sequences SEQ ID NO:9/SEQ ID NO:10, the inventors were therefore finally able to determine the partial sequence of the rpoB gene in 29 species of the *Staphylococcus* genus listed below (SEQ ID NO:11 to SEQ ID NO:39).

The fragment of the rpoB gene was amplified with the PCR technique using 35 amplification cycles each comprising a denaturing phase at 94° C. for 10 seconds, a hybridization phase of primers SEQ ID NOs:7 and 8 or SEQ ID NOs:7 and 10 at 52° C. for 20 seconds, and an elongation phase at 72° C. for 60 seconds. The amplification product was visualized after ethidium bromide staining.

The bacteria representing these 29 species of the *Staphylococcus* genus are the following:

| Species | GenBank accession n° | Reference |
|---|---|---|
| *Staphylococcus caprae* | AF325868 (SEQ ID NO: 39) | CIP 104000[T] |
| *Staphylococcus gallinarum* | AF325890 (SEQ ID NO: 27) | CIP 103504[T] |

-continued

| Species | GenBank accession n° | Reference |
|---|---|---|
| *Staphylococcus aureus* subsp. *anaerobius* | AF325894 (SEQ ID NO: 37) | CIP 103780[T] |
| *Staphylococcus aureus* subsp. *aureus* | X64172 (SEQ ID NO: 36) | CIP 103428[T] |
| *Staphylococcus epidermidis* | AF325872 (SEQ ID NO: 30) | CIP 81.55[T] |
| *Staphylococcus haemolyticus* | AF325888 (SEQ ID NO: 26) | CIP 81.56[T] |
| *Staphylococcus intermedius* | AF325869 (SEQ ID NO: 23) | CIP 81.60[T] |
| *Staphylococcus lugdunensis* | AF325870 (SEQ ID NO: 20) | CIP 103642[T] |
| *Staphylococcus saccharolyticus* | AF325871 (SEQ ID NO: 17) | CIP 103275[T] |
| *Staphylococcus schleiferi* subsp. *schleiferi* | AF325886 (SEQ ID NO: 15) | CIP 103643[T] |
| *Staphylococcus xylosus* | AF325883 (SEQ ID NO: 11) | CIP 81.66[T] |
| *Staphylococcus capitis* subsp. *capitis* | AF325885 (SEQ ID NO: 34) | ATCC 27840[T] |
| *Staphylococcus arlettae* | AF325874 (SEQ ID NO: 38) | ATCC 43957[T] |
| *Staphylococcus warneri* | AF325887 (SEQ ID NO: 12) | ATCC 27836[T] |
| *Staphylococcus hominis* | AF325875 (SEQ ID NO: 25) | ATCC 27844[T] |
| *Staphylococcus simulans* | AF325877 (SEQ ID NO: 13) | ATCC 27848[T] |
| *Staphylococcus saprophyticus* | AF325873 (SEQ ID NO: 16) | ATCC 15305[T] |
| *Staphylococcus equorum* | AF325882 (SEQ ID NO: 29) | ATCC 43958[T] |
| *Staphylococcus cohnii* subsp. *Cohnii* | AF325893 (SEQ ID NO: 31) | ATCC 29974[T] |
| *Staphylococcus auricularis* | AF325889 (SEQ ID NO: 35) | ATCC 33753[T] |
| *Staphylococcus carnosus* subsp. *Carnosus* | AF325880 (SEQ ID NO: 33) | ATCC 51365[T] |
| *Staphylococcus kloosii* | AF325891 (SEQ ID NO: 22) | ATCC 43959[T] |
| *Staphylococcus chromogenes* | AF325892 (SEQ ID NO: 32) | ATCC 43764[T] |
| *Staphylococcus hyicus* subsp. *hyicus* | AF325876 (SEQ ID NO: 24) | ATCC 11249[T] |
| *Staphylococcus pulveris* | AF325879 (SEQ ID NO: 18) | CCUG 33938[T] |
| *Staphylococcus muscae* | AF325884 (SEQ ID NO: 19) | CIP 103564[T] |
| *Staphylococcus lentus* | AF036973 (SEQ ID NO: 21) | ATCC 49574 |
| *Staphylococcus felis* | AF325878 (SEQ ID NO: 28) | CIP 103366[T] |
| *Staphylococcus sciuri* | AF325881 (SEQ ID NO: 14) | ATCC 29062[T] |

ATCC: American Tissue Culture Collection;
CIP: Collection de l'Institut Pasteur;
[T]type strain.

The fragments of, in general, approximately 500 base pairs of the rpoB gene of the bacteria of species belonging to the *Staphylococcus* genus whose sequence is specific to each species of this genus and therefore enabling molecular identification of the bacteria of the 29 species tested are:

SEQ ID NO:11: Partial sequence of the rpoB gene in *Staphylococcus xylosus*, measuring 518 base pairs:

```
                                            (SEQ ID NO: 11)
5'TTCAGGGTTCATCAATGGCACTGCTTGACGTTGCATGTTTGCACCCAT

CAATGCACGGTTAGAGTCATCATTTTCTAAGAAAGGAATACATGCTGTCG

CAGCAGAAACAACTTGTTTTGGTGAAACGTCCATGTAATCCATTTTTTCT

TTAGCCATAACTGTGTTATTACCACGGAAACGACAAACAACTTCATCATC

TAAGAAACGACCATTTTCATCTAATTTAGAGTTGGCTTGTGCTACCACAT

AACTATCCTCTTCATCAGCTGTTAAGTAATCGATTTGCTCAGTAATGCTG

TTTGTTTCAAGGTCTACTTTACGATAAGGTGTTTCAATGAAACCAAATTC

ATTCACACGTGCATAACTAGACAATGAGTTGATAAGTCCAATGTTTGGAC

CTTCAGGCGTTTCGATTGGACACATACGGCCATAGTGAGAATAGTGAACG
```

TCACGTACTTCCATTTGAGCACGTTCACGTGTTAAACCACCAGGTCCTAG

AGCAGATAAACGACGTTTGT-3'

SEQ ID NO:12: Partial sequence of the rpoB gene in *Staphylococcus warneri*, measuring 507 base pairs:

(SEQ ID NO: 12)
5'TTCAGGATTCATCAATGGTACTGCTTGACGTTGCATGTTCGCACCCAT

TAATGCACGGTTAGAGTCATCGTTTTCTAAGAATGGAATACAAGCTGTAG

CGGCTGAAACAACCTGCTTAGGTGAAACGTCCATGTAATCCATTTTTTCT

TTAGCCATTACTGTGTTATTACCACGGAAACGACAAACTACTTCGTCATC

TATGAAACGTCCGTTTTCATCTAAACGTGAATTCGCTTGGGCAACAACAT

AACTATCTTCTTCGTCAGCAGTTAAATAATCAATTTGGTCTGTAATCGCA

TTAGTGTCTAAATCCACTTTACGATATGGTGTTTCAATGAAACCAAATTC

GTTTACACGTGCATAACTAGATAATGAGTTGATTAATCCAATGTTTGGAC

CCTCTGGCGTTTCAATTGGACACATACGACCATAGTGAGAATAGTGTACG

TCACGTACCTCCATTTGTGCACGTTCACGTGTTAAACCACCAGGTCCTAA

AGCAGATAA-3'

SEQ ID NO:13: Partial sequence of the rpoB gene in *Staphylococcus simulans*, measuring 518 base pairs:

(SEQ ID NO: 13)
5'TTCAGGGTTCATCAATGGTACTGCTTGACGTTGCATGTTCGCACCCAT

TAACGCACGGTTAGAGTCATCGTTTTCTAAGAATGGGATACATGCTGTCG

CTGCAGATACAACTTGTTTAGGAGAAACGTCCATATAGTCCATTTTCTCT

CTATCCATAGTTGTGTTGTTACCACGGAAACGACAAACGATTCTTCGTC

TAAGAAACGACCTTCGTCATCTAAACGTGAGTTCGCTTGCGCAACAACAT

AGCTGTCTTCTTCGTCTGCAGTAAGGTAATCGATTTGATCTGTTACCGCA

TTTTTCTCATGGTCAACTTTACGATATGGTGTTTCAATGAAACCAAATTC

ATTAACACGCGCATAACTTGATAATGAGTTGATTAAACCGATGTTCGGAC

CCTCTGGTGTCTCGATTGGACACATACGGCCATAGTGAGAGTAATGCACG

TCACGTACTTCCATTTGTGCACGTTCACGTGTTAAACCACCAGGTCCAAG

TGCAGATAGACGACGTTTAT-3'

SEQ ID NO:14: Partial sequence of the rpoB gene in *Staphylococcus sciuri*, measuring 507 base pairs:

(SEQ ID NO: 14)
5'TTCTGGGTTCATTAAAGGTACCGCTTGACGTTGCATGTTTGCACCCAT

AAGCGCACGGTTAGAGTCATCGTTTTCTAAGAATGGAATACATGCTGTCG

CTGCAGAAACAACTTGTTTAGGAGATACATCCATGTAGTCCATGCGTTCT

TTAGGTTTAGTAGTGTTGTCCCCACGGAAACGACAAAGAACTTCATCATC

AACGAATTTACCTGTTTCATCAAGTACAGAGTTTGCTTGTGCAACTACAT

AGCTGTCTTCTTCGTCAGCTGTTAAGTAGTCGATTCTGTCAGTAACTTGG

TTTGTCTCGATGTTTACCTTACGATAAGGTGTTTCAATGAAACCAAATTC

ATTAACTCTTGCATAACTTGATAATGAGTTGATTAAACCAATGTTTGGTC

CCTCAGGCGTTTCAATTGGACACATACGACCATAGTGAGAGTAGTGAACG

TCACGTACTTCCATACCAGCACGCTCACGAGTTAAACCACCCGGTCCTAA

TGCTGATAG-3'

SEQ ID NO:15: Partial sequence of the rpoB gene in *Staphylococcus schleiferi*, measuring 518 base pairs:

(SEQ ID NO: 15)
5'TTCTGGGTTTAACAATGGTACTGCTTGACGTTGCATGTTCGCACCCAT

CAATGCACGGTTAGAGTCATCGTTTTCTAAAAACGGAATACATGCTGTCG

CAGCTGAAACAACTTGTTTAGGCGATACGTCCATGTAGTCCATTTTTTCT

TTAGCCATAGTTGTGTTGTTACCACGGAAACGACAAACGATTTCGTCATC

GATAAAACGTCCGTTTTCATCAAGTCTTGAGTTCGCTTGGGCAACAACAT

AACTGTCTTCTTCATCAGCAGTAAGGTAATCAATACGGTCTGTAATTGTG

TTTGTTTCAAGGTCTACTTTTCTGTATGGAGTTTCAATGAAACCAAATTC

ATTCACACGTGCATAACTTGAAAGTGAGTTGATCAAACCAATGTTTGGAC

CCTCTGGTGTCTCGATTGGACACATACGGCCATAGTGAGAATAGTGTACG

TCACGAACTTCCATTTGTGCACGTTCACGTGTTAAACCACCAGGCCCTAA

AGCTGATAAACGACGTTTGT-3'

SEQ ID NO:16: Partial sequence of the rpoB gene in *Staphylococcus saprophyticus*, measuring 518 base pairs:

(SEQ ID NO: 16)
5'TTCTGGATTCATCAATGGCACTGCTTGACGTTGCATGTTCGCACCCAT

CAATGCACGGTTAGAGTCATCGTTTTCTAAGAAAGGAATACATGCTGTCG

CTGCAGAAACAACTTGTTTAGGTGAGACATCCATATAATCCATTTTTTCT

TTGGCCATAACTGTATTATTACCACGGAAACGACAAACAACTTCGTCTGC

TATGAAACGGCCATTTTCGTCTAATGTTGAGTTTGCTTGTGCTACAACAT

AGCTATCTTCTTCATCAGCTGTTAAATAGTCAATTTGATCCGTGATTGAA

TTCGTTTCAAGATCCACTTTACGGTAAGGTGTTTCAATAAAGCCGAATTC

ATTTACACGCGCATAACTAGATAACGAGTTAATAAGTCCGATGTTTGGAC

CCTCTGGCGTTTCAATTGGACACATACGGCCATAGTGAGAATAGTGAACG

TCACGTACTTCCATTTGAGCACGTTCACGCGTTAAACCACCAGGTCCTAG

AGCTGATAAACGACGTTTAT-3'

SEQ ID NO:17: Partial sequence of the rpoB gene in *Staphylococcus saccharolyticus*, measuring 556 base pairs:

(SEQ ID NO: 17)
5'AAACCCATTAGCTGAGTTGACTCATAAACGTCGTTTATCAGCTCTAGG

ACCTGGTGGTTTAACTCGTGAACGCGCTCAAATGGAAGTACGTGACGTGC

ATTATTCTCACTACGGTCGTATGTGCCCTATTGAAACACCTGAGGGCCCA

AACATTGGATTAATTAACTCATTATCTAGTTATGCAAGAGTAAATGAATT

TGGTTTTATTGAAACACCTTATCGTAAAGTTGATTTAGATACTAATTCAA

-continued
TCACTGACCAAATTGACTACTTAACTGCTGATGAAGAAGATAGTTATGTT

GTTGCACAAGCAAACTCACGTCTTGATGAAAATGGGTGCTTCTTAGATGA

TGAAGTTGTTTGTCGTTTTCGTGGCAATAACACAGTGATGGCTAAAGAAA

AAATGGACTATATGGACGTATCACCTAAACAAGTAGTTTCAGCAGCTACT

GCATGTATCCCATTCTTAGAAAACGATGACTCAAACCGAGCATTAATGGG

TGCAAACATGCAACGTCAAGCAGTACCATTAATGAACCCAGAAGCGCCAT

TTGTTGGA-3'

SEQ ID NO:18: Partial sequence of the rpoB gene in *Staphylococcus pulveris*, measuring 508 base pairs:

(SEQ ID NO: 18)
5'TTCAGGATTCATTAAAGGCACTGCTTGACGTTGCATGTTTGCACCCAT

AAGCGCACGGTTAGAGTCATCGTTTTCTAAGAAAGGAATACATGCTGTCG

CAGCAGAAACAACCTGTTTAGGTGATACATCCATGTAATCCATACGTTCT

TTAGGTTTCGTAGTATTATCCCCACGGAAACGACAAAGTACTTCATCATC

AACGAATTTACCTGTTTCATCAAGTACTGAGTTTGCTTGCGCTACAACAT

AGCTGTCTTCTTCGTCAGCTGTTAAATAGTCAATTCTGTCAGTAACTTGG

TTTGTTTCGATATTAACCTTACGATAAGGCGTTTCAATAAAACCAAATTC

ATTAACTCTCGCATAACTTGATAAAGAGTTAATTAAACCGATGTTTGGTC

CCTCAGGTGTTTCAATTGGACACATACGACCATAGTGAGAATAGTGAACG

TCACGTACTTCCATACCAGCACGTTCACGAAGTTAAACCGCCGGGTCCTA

ATGCTGATAG-3'

SEQ ID NO:19: Partial sequence of the rpoB gene in *Staphylococcus muscae*, measuring 518 base pairs:

(SEQ ID NO: 19)
5'TTCAGGATTCAACAATGGCACCGCTTGACGTTGCATGTTCGCACCCAT

TAAGGCACGGTTAGAGTCATCGTTTTCTAAGAATGGAATACATGCTGTCG

CAGCAGAAACAACTTGCTTCGGCGATACGTCCATGTAGTCCATTTTCTCT

TTTGCCATTGTTGTGTTGTTACCACGGAAACGACATACAATCTCATCATC

AATAAAGCGACCATTTTCATCTAAACGTGAGTTCGCTTGTGCAACCACAT

AACTATCTTCTTCATCAGCAGTTAAATAGTCGATTTGATCAGTGATTGTG

TTCGTCTCGATATCAACTTTACGATATGGTGTTTCAATGAAACCAAATTC

ATTAACACGTGCATAACTAGATAGTGAGTTGATCAAACCAATGTTCAGTC

CCTCTGGTGTCTCAATCGGACACATACGACCATAGTGAGAGTAGTGAACG

TCACGCACTTCCATTTGTGCACGTTCACGTGTCAAACCACCAGGCCCTAA

TGCTGAAAGACGACGCTTAT-3'

SEQ ID NO:20: Partial sequence of the rpoB gene in *Staphylococcus lugdunensis*, measuring 556 base pairs:

(SEQ ID NO: 20)
5'TAACCCATTAGCAGAATTAACACACAAACGTCGTTTATCTGCGTTAGG

ACCTGGTGGTTTAACACGTGAACGTGCACAAATGGAAGTTCGTGACGTGC

ATTATTCTCACTATGGCCGTATGTGTCCGATTGAAACACCAGAGGGTCCA

AACATTGGTTTGATTAACTCATTATCTAGTTATGCGCGTGTCAACGAGTT

TGGCTTTATTGAAACGCCTTATCGTAAAGTAGATATTGATACAAATGCAA

TCACAGATCAAATTGACTACTTAACTGCTGATGAAGAAGACAGTTATGTC

GTTGCACAAGCGAACTCTCGCCTTGATGAAAATGGTCGTTTCTTAGATGA

TGAAGTAGTATGCCGTTTCCGCGGTAATAATACTGTTATGGCTAAAGAAA

AAATGGACTACATGGATGTATCTCCTAAACAAGTTGTTTCAGCTGCGACA

GCATGTATTCCATTCTTAGAGAACGATGACTCTAACCGTGCATTGATGGG

TGCAAACATGCAACGTCAAGCAGTTCCGTTGATGAACCCTGAAGCGCCGT

TCGTAGGA-3'

SEQ ID NO:21: Partial sequence of the rpoB gene in *Staphylococcus lentus*, measuring 507 base pairs:

(SEQ ID NO: 21)
5'TTCAGGGTTCATTAAAGGTACTGCTTGACGTTGCATGTTCGCACCCAT

TAAGGCACGGTTAGAGTCATCGTTTTCAAGGAAAGGAATACATGCTGATG

GTGCAGAAACAACTTGTTTAGGAGATACATCCATGTAATCCATACGTTCT

TTAGGTTTAGTAGTGTTGTCACCACGGAAACGACAAAGAACTTCATCGTC

GACGAATCTACCAGTTTCATCTAATACTGAGTTTGCTTGTGCAACAACAT

AACTATCTTCTTCATCAGCAGTTAGATAATCAATTCTGTCTGTTACTTGG

TTAGTTTCGATATTAACTTTACGATATGGTGTTTCAATAAAGCCAAACTC

GTTAACTCTAGCATAACTTGAAAGTGAGTTGATTAAACCAATGTTTGGTC

CCTCTGGTGTCTCAATCGGACACATACGACCATAGTGAGAATAGTGAACG

TCACGTACTTCCATACCAGCACGTTCACGAGTTAAACCGCCGGGTCCAAG

CGCTGATAG-3'

SEQ ID NO:22: Partial sequence of the rpoB gene in *Staphylococcus kloosii*, measuring 505 base pairs:

(SEQ ID NO: 22)
5'TTCACGGTTCATCAATGGTACCGCTTGACGTTGCATGTTCGCACCCAT

TAAGGCACGGTTAGAGTCATCGTTTTCTAAGAAAGGAATACATGCTGTCG

CAGCCGAAACAACTTGTTTTGGTGATACGTCCATGTAGTCCATTTTTTCT

TTCGCCATAACTGTGTTGTTACCACGGAAACGACAAACTACTTCATCATC

TAAGAAACGACCATTTTCATCTAATTTAGAGTTAGCTTGCGCTACCACAT

AGCTATCTTCTTCATCAGCTGTTAAATAGTCAATTTGATCTGTGATTGAA

TTAGTTTCTAAATCAACTTTACGGTATGGTGTTTCGATAAAGCCAAATTC

ATTAACACGTGCATAACTTGATAATGAGTTGATAAGTCCAATGTTTGGAC

CCTCTGGCGTTTCGATTGGACACATACGACCATAGTGAGAATAGTAACGT

CACGCACTTCCATTTGAGCACGTTCACGAGTTAAACCACCAGGTCCAAGC

CAGATAG-3'

SEQ ID NO:23: Partial sequence of the rpoB gene in *Staphylococcus intermedius*, measuring 556 base pairs:

(SEQ ID NO: 23)
5'GAACCCACTTGCTGAGTTGACTCACAAACGTCGTCTATCAGCATTAGG

ACCTGGTGGTTTAACGCGTGAACGTGCTCAAATGGAAGTGCGTGACGTAC

ACTACTCTCACTATGGTCGTATGTGTCCAATCGAAACACCTGAGGGACCA

AACATTGGTTTGATCAACTCATTATCTAGTTATGCACGTGTGAACGAATT

TGGTTTTATCGAAACACCTATATCGTAAAGTTGATATTGAAACAAATACGA

TTACTGACCAAATCGACTACTTAACTGCTGATGAAGAAGATAGTTATGTT

GTCGCACAAGCGAACTCACGTCTTGATGAAAACGGTCGCTTTATTGATGA

TGAGATTGTATGTCGTTTCCGTGGTAACAACACAACGATGGCGAAAGAAA

AAATGGACTACATGGACGTATCGCCGAAACAAGTTGTATCAGCTGCGACA

GCGTGTATCCCATTCTTAGAAAACGATGACTCTAACCGTGCGTTAATGGG

TGCGAACATGCAGCGTCAAGCGGTACCGTTGTTAAACCCTGAATCTCCAT

TTGTAGGT-3'

SEQ ID NO:24: Partial sequence of the rpoB gene in *Staphylococcus hyicus*, measuring 518 base pairs:

(SEQ ID NO: 24)
5'CTCTGGGTTCAATAAAGGCACGGCTTGACGTTGCATGTTCGCACCCAT

TAATGCACGGTTCGAGTCATCGTTTTCTAAGAATGGGATACATGCTGTCG

CCGCAGAAACAACTTGTTTCGGTGATACGTCCATGTAATCCATTTTTCT

TTAGCCATTGTTGTATTGTTCCCACGGAAACGACAAACGATTTCGTCGTC

GATAAAGCGTCCATTTTCATCTAAACGTGAGTTCGCTTGGGCAACAACAT

AACTGTCTTCTTCATCCGCAGTTAAGTAATCAATTTGATCTGTTATTGTA

TTCGTTTCAAGGTCCACTTTACGGTAAGGCGTTTCAATGAAACCAAATTC

GTTAACACGCGCATAACTTGAAAGTGAGTTGATTAATCCAATGTTTGGAC

CCTCTGGCGTTTCGATTGGACACATACGACCGTAGTGAGAGTAGTGAACG

TCACGCACTTCCATTTGGGCACGTTCACGCGTTAAACCACCAGGTCCTAA

TGCAGATAAACGACGTTTGG-3'

SEQ ID NO:25: Partial sequence of the rpoB gene in *Staphylococcus hominis*, measuring 518 base pairs:

(SEQ ID NO: 25)
5'TTCAGGATTCATCAATGGTACTGCTTGACGTTGCATGTTCGCACCCAT

TAACGCACGGTTAGAGTCATCGTTTTCAAGGAATGGAATACAAGCTGTCG

CTGCTGATACTACTTGTTTAGGAGATACATCCATGTAGTCCATTTTTCT

TTTGCCATAACAGTGTTGTTACCACGGAAACGACATACCACTTCATCATC

TAGGAAACGACCATTTTCATCTAAACGAGAATTGGCTTGTGCAACTACAT

AGCTATCTTCTTCATCAGCAGTTAAATAATCAATTTGATCAGTAATCGAA

TTGGTATCAATATCTACTTTACGATATGGTGTTTCGATAAAACCAAATTC

ATTTACACGTGCATAACTAGATAATGAGTTAATTAAACCAATGTTTGGTC

CCTCTGGTGTTTCAATTGGACACATACGACCATAGTGAGAATAGTGTACG

TCACGAACTTCCATTTGTGCACGTTCACGTGTTAAACCACCAGGTCCTAA

AGCAGAAAGACGACGTTTAG-3'

SEQ ID NO:26: Partial sequence of the rpoB gene in *Staphylococcus haemolyticus*, measuring 507 base pairs:

(SEQ ID NO: 26)
5'TTCTGTGTTCATCAATGGTACTGCtTGACGTTGCATGTTTGCACCCAT

TAATGCACGGTTAGAGTCATCATTTTCAAGGAAAGGAATACATGCTGTCG

CAGCTGAAACTACTTGTTTAGGAGATACGTCCATGTAGTCCATTTTCTCT

TTAGCCATAACTGTGTTATTACCACGGAAACGACATACGACTTCATCATC

TAAGAAACGACCATTTTCATCTAAGCGAGAGTTCGCTTGGGCAACTACAT

AGCTATCTTCTTCATCAGCAGTTAAGTAGTCGATTTGATCTGTAATAGAG

TTAGTGTCTAAGTCTACTTTACGATATGGTGTTTCAATGAAACCAAATTC

ATTCACACGTGCATAACTTGATAATGAGTTAATCAAACCAATGTTTGGTC

CCTCTGGAGTCTCGATCGGACACATACGACCATAGTGAGAGTAGTGAACG

TCACGTACTTCCATTTGAGCACGTTCACGTGTTAAACCACCAGGTCCTAA

TGCAGAAAG-3'

SEQ ID NO:27: Partial sequence of the rpoB gene in *Staphylococcus gallinarum*, measuring 507 base pairs:

(SEQ ID NO: 27)
5'TTCAGGATTCATCAAAGGTACAGCTTGACGTTGCATGTTCGCACCCAT

CAATGCACGGTTAGAGTCATCGTTTTCTAAGAAAGGAATACATGCTGTCG

CAGCAGATACAACCTGTTTAGGTGATACATCCATGTAGTCCATTTTTTCT

TTTGCCATTACAGTGTTGTTACCACGGAAACGACAAACGACTTCATCTTC

TACGAAACGACCATTTTCATCTAATACAGAGTTTGCTTGTGCTACTACAT

AACTGTCTTCTTCATCAGCTGTTAAGTAGTCAATTTGATCTGTAATAGAT

TGTGTTTCAATATCAACTTTACGATATGGTGTTTCAATGAAACCAAATTC

ATTTACACGCGCATAACTTGATAATGAGTTGATAAGTCCGATGTTTGGAC

CCTCAGGTGTTTCGATTGGACACATACGGCCATAGTGAGAATAGTGAACG

TCACGTACTTCCATTTGAGCACGTTCACGAGTTAAACCACCAGGTCCTAA

TGCTGATAG-3'

SEQ ID NO:28: Partial sequence of the rpoB gene in *Staphylococcus felis*, measuring 518 base pairs:

(SEQ ID NO: 28)
5'TTCGGGATTCATTAAAGGTACAGCTTGACGTTGCATGTTCGCACCCAT

TAATGCACGGTTAGAGTCATCGTTTTCTAAGAATGGGATACATGCCGTCG

CAGCAGAAACGACTTGCTTAGGCGATACGTCCATGTAGTCCATTTTTCT

TTGGCCATCGTTGTATTGTTTCCGCGGAAACGACATACAATCTCGTCATC

CAAGAAACGGCCTTCTTCGTCTAATCGTGCGTTTGCTTGTGCAACAACAT

AACTATCTTCTTCATCAGCTGTAAGATAGTCAATTTGGTCTGTAATTTTA

TTTGTCTCAAGATCGACTTTACGATATGGTGTTTCGATAAATCCAAATTC

GTTAACACGTGCATAACTTGATAATGAGTTGATTAATCCGATGTTCGGCC

CCTCTGGCGTTTCAATAGGACACATGCGACCATAGTGAGAGTAGTGAACG

TCACGCACTTCCATCTGTGCACGTTCTCTCGTTAAACCACCAGGTCCTAA

TGCGGATAGACGACGTTTAT-3'

SEQ ID NO:29: Partial sequence of the rpoB gene in *Staphylococcus equorum*, measuring 507 base pairs:

(SEQ ID NO: 29)
5'TTCAGGATTCATCAATGGCACTGCTTGACGTTGCATGTTTGCACCCAT

CAATGCACGGTTAGAGTCATCGTTTTCTAAGAAAGGAATACATGCTGTCG

CAGCAGAAACAACTTGTTTAGGTGAAACATCCATGTAGTCCATTTTTTCT

TTAGCCATAACTGTGTTATTACCACGGAAACGACAAACAACTTCGTCTTC

TACGAAACGACCATTTTCATCTAATACAGAGTTTGCTTGAGCTACTACAT

AGCTGTCTTCTTCGTCAGCTGTTAAGTAGTCAATTTGGTCTGTGATTGAA

TGTGTTTCAAGATCTACTTTACGGTAAGGTGTTTCAATGAAACCAAATTC

ATTCACACGCGCATAACTAGATAGTGAGTTGATAAGTCCGATATTCGGAC

CCTCTGGTGTTTCGATTGGACACATACGACCATAGTGAGAATAGTGAACG

TCACGTACTTCCATTTGAGCACGTTCACGTGTTAAACCGCCGGGTCCTAA

TGCTGATAA-3'

SEQ ID NO:30: Partial sequence of the rpoB gene in *Staphylococcus epidermidis*, measuring 518 base pairs:

(SEQ ID NO: 30)
5'TTCAGGATTCATTAAAGGCACCGCTTGACGTTGCATGTTTGCTCCCAT

TAACGCACGGTTAGAGTCGTCATTTTCTAAGAATGGAATACATGCTGTTG

CTGCTGAAACAACTTGTTTTGGTGATACGTCCATGTAATCCATTTTTTCT

TTAGCCATAACAGTGTTATTACCACGGAAACGACAAACAACTTCATCATC

TAAGAAACGACCATTTTCATCAAGTCTAGAATTAGCCTGTGCAACAACGT

AGCTATCCTCTTCATCAGCTGTCAAATAATCTATTTGATCAGTGATTGAG

TTTGTATCTAAATCCACTTTACGATATGGCGTTTCAATAAAACCAAATTC

ATTCACTCTAGCATAACTTGACAATGAGTTTATTAAACCAATATTAGGAC

CCTCAGGTGTTTCAATTGGACACATACGCCCATAGTGAGAGTAGTGAACG

TCACGCACTTCCATTTGAGCACGTTCACGTGTTAATCCACCAGGCCCTAG

AGCAGATAAACGACGTTTGT-3'

SEQ ID NO:31: Partial sequence of the rpoB gene in *Staphylococcus cohnii*, measuring 507 base pairs:

(SEQ ID NO: 31)
5'TTCTGGATTCATCAATGGGACTGCTTGACGTTGCATGTTCGCACCCAT

TAATGCACGGTTAGAGTCATCGTTTTCTAAGAATGGAATACATGCTGTTG

CTGCAGAAACAACCTGTTTAGGAGATACATCCATGTAATCCATTTTTTCT

TTTGCCATAACTGTGTTATTACCACGGAAACGACAAACAACTTCATCATC

TAAGAAGCGACCATTTTCATCTAACTTAGAATTTGCTTGTGCTACTACAT

AGCTATCTTCTTCGTCAGCTGTTAAATAATCAATTTGATCTGTGATACTA

TTCGTTTCAAGATCTACTTTACGATATGGCGTTTCAATGAAACCAAATTC

ATTTACACGTGCATAACTTGATAATGAGTTAATCAAACCAATGTTTGGTC

CCTCTGGTGTTTCGATTGGACACATACGACCGTAGTGAGAGTAGTGAACG

TCACGCACTTCCATTTGAGCACGTTCACGTGTTAAACCACCAGGTCCTAA

TGCTGATAG-3'

SEQ ID NO:32: Partial sequence of the rpoB gene in *Staphylococcus chromogenes*, measuring 507 base pairs:

(SEQ ID NO: 32)
5'CTCAGGATTTAACAAAGGCACCGCTTGACGTTGGATGTTCGCACCCAT

TAACGCACGGTTAGAGTCATCGTTTTCTAAGAACGGAATACATGCAGTTG

CCGCAGAAACAACTTGCTTCGGTGATACGTCCATGTAATCCATTTTTTCT

TTAGCCATTGTTGTATTGTTCCCACGGAAACGACAAACGATTTCGTCGTC

GATAAAGCGTCCATTTTCATCTAAACGTGAGTTCGCTTGGGCAACAACAT

AACTGTCTTCTTCGTCCGCAGTTAAATAATCAATTTGATCAGTAATTGCG

TTCGTTTCAAGGTCTACTTTACGATACGGCGTTTCAATAAAACCAAATTC

ATTAACACGCGCATAACTTGAAAGTGAGTTGATTAATCCAATATTTGGAC

CCTCTGGTGTTTCGATTGGACACATACGACCGTAGTGAGAATAGTGAACG

TCACGCACTTCCATTTGAGCACGTTCACGTGTTAAACCACCTGGTCCTAA

AGCAGATAA-3'

SEQ ID NO:33: Partial sequence of the rpoB gene in *Staphylococcus carnosus*, measuring 1,025 base pairs:

(SEQ ID NO: 33)
5'TTCTGGATTCATCAATGGTACCGCTTGACGTTGCATGTTCGCACCCAT

TAATGCACGGTTAGAGTCATCGTTTTCTAAGAATGGGATACAAGCTGTCG

CAGCTGATACTACTTGTTTTGGTGATACGTCCATGTAGTCCATTTTGTCT

CTGTCCATCATTGTGTTGTTACCACGGAAACGACAAACAACTTCTTCGCT

GATGAAGTGACCTTCATCATCTAAACGAGAGTTCGCTTGGGCTACAACAT

AGCTGTCTTCTTCGTCAGCTGTTAGATAGTCGATTTGATCAGTTACAGTA

TTAGTTTCAAGGTCAACTTTACGGTATGGTGTTTCAATAAAACCGAACTC

GTTAACACGTGCATAACTTGATAATGAGTTGATCAAACCAATGTTTGGAC

CCTCAGGAGTTTCGATTGGACACATACGGCCATAGTGAGAATAGTGAACG

TCACGTACTTCCATTTGAGCACGTTCACGAGTTAAACCACCAGGTCCTAA

TGCAGATAATTCTGGATTCATCAATGGTACTGCTTGACGTTGCATGTTCG

CACCCATTAATGCACGGTTAGAGTCATCATTTTCTAAGAATGGAATACAA

GCTGTCGCTGCAGATACTACTTGTTTAGGAGATACATCCATGTAGTCCAT

TTTCTCTTTAGCCATAACTGTGTTATTACCACGGAAACGACAAACAACTT

CGTCATCTAAGAAACGACCATTTTCGTCTAAACGAGAGTTCGCTTGGGCA

ACAACATAACTATCTTCTTCATCAGCAGTTAAGTAATCAATTTGGTCAGT

GATAGAATTCGTATCTAAATCTACTTTACGATAAGGTGTTTCAATAAAAC

CAAATTCATTTACTCGTGCATAACTTGATAATGAGTTGATTAAACCAATG

TTTGGTCCCTCAGGTGTTTCGATTGGACACATACGGCCATAGTGAGAATA

GTGAACGTCACGCACTTCCATTTGGGCACGTTCACGCGTTAAACCACCAG

GTCCTAATGCTGATAGACGACGTTTAT-3'

SEQ ID NO:34: Partial sequence of the rpoB gene in *Staphylococcus capitis*, measuring 518 base pairs:

(SEQ ID NO: 34)
5'TTCAGTGTTCATCAATGGTACCGCTTGACGTTGCATGTTCGCACCCAT

TAATGCACGGTTAGAGTCATCGTTTTCTAAGAATGGAATACATGCTGTAG

CTGCTGATACAACTTGTTTAGGTGATACGTCCATGTAATCCATTTTTTCT

TTTGCCATAACTGTGTTATTACCACGGAAACGACAAACAACCTCGTCATC

TAAGAAACGACCATTTTCGTCTAAACGTGAGTTGGCTTGGGCAACTACAT

AGCTATCTTCTTCATCAGCAGTTAAGTAATCGATTTGATCTGTGATAGAG

TTCGTATCTAAATCAACTTTACGATACGGTGTCTCGATGAAACCAAATTC

ATTTACTCGCGCATAACTTGATAATGAGTTAATTAAACCAATATTTGGAC

CCTCTGGTGTTTCAATTGGACACATACGACCATAGTGTGAGTAATGAACG

TCACGTACTTCCATTTGAGCACGTTCACGAGTTAAACCACCAGGTCCTAA

TGCTGATAGACGACGTTTTG-3'

SEQ ID NO:35: Partial sequence of the rpoB gene in *Staphylococcus auricularis*, measuring 507 base pairs:

(SEQ ID NO: 35)
5'TTCTGGGTTCATTAAAGGTACCGCTTGACGTTGCATGTTTGCACCCAT

AAGCGCACGGTTAGAGTCATCGTTTTCTAAGAATGGAATACATGCTGTCG

CTGCAGAAACAACTTGTTTAGGAGATACATCCATGTAGTCCATGCGTTCT

TTAGGTTTAGTAGTGTTGTCCCCACGGAAACGACAAAGAACTTCATCATC

AACGAATTTACCTGTTTCATCAAGTACAGAGTTTGCTTGTGCAACTACAT

AGCTGTCTTCTTCGTCAGCTGTTAAGTAGTCGATTCTGTCAGTAACTTGG

TTTGTCTCGATGTTTACCTTACGATAAGGTGTTTCAATGAAACCAAATTC

ATTAACTCTTGCATAACTTGATAATGAGTTGATTAAACCAATGTTTGGTC

CCTCAGGCGTTTCAATTGGACACATACGACCATAGTGAGAGTAGTGAACG

TCACGTACTTCCATACCAGCACGCTCACGAGTTAAACCACCCGGTCCTAA

TGCTGATAG-3'

SEQ ID NO:36: Partial sequence of the rpoB gene in *Staphylococcus aureus*, measuring 518 base pairs:

(SEQ ID NO: 36)
5'TTCTGGATTCATCAAAGGCACTGCTTGACGTTGCATGTTCGCACCCAT

CAATGCACGGTTTGAGTCATCATTTTCTAAGAATGGAATACATGCTGTCG

CTGCTGAAACAACTTGCTTCGGCGATACATCCATATAATCCATTTTTTCT

TTAGCCATAACTGTGTTGTTACCACGGAAACGACATACAACTTCATCATC

CATGAAACGACCATTTTCATCTAATTTAGAGTTTGCTTGTGCTACAACAT

AGCTATCTTCTTCGTCAGCTGTTAAATAGTCAATTTGATCAGTGATAGCA

TGTGTATCTAAATCAACTTTACGATATGGTGTTTCAATAAAGCCGAATTC

ATTTACACGTGCATAACTTGATAATGAGTTAATCAATCCAATGTTTGGTC

CCTCAGGTGTTTCAATTGGACACATACGGCCATAGTGAGAGTAGTGAACG

TCACGTACTTCCATTTGAGCACGTTCACGTGTTAAACCACCAGGTCCTAA

TGCTGATAGACGACGTTTAT-3'

SEQ ID NO:37: Partial sequence of the rpoB gene in *Staphylococcus aureus anaerobius*, measuring 507 base pairs:

(SEQ ID NO: 37)
5'TTCTGGATTCATCAAAGGCACTGCTTGACGTTGCATGTTCGCACCCAT

CAATGCACGGTTTGAGTCATCATTTTCTAAGAATGGAATACATGCTGTCG

CTGCTGAAACAACTTGCTTCGGCGATACATCCATATAATCCATTTTTTCT

TTAGCCATAACTGTATTGTTACCACGGAAACGACATACAACTTCATCATC

CATGAAACGACCATTTTCATCTAATTTAGAGTTTGCTTGTGCTACAACAT

AGCTATCTTCTTCGTCAGCTGTTAAATAGTCAATTTGATCAGTGATAGCA

TGTGTATCTAAATCAACTTTACGATATGGTGTTTCAATAAAGCCGAATTC

ATTTACACGTGCATAACTTGATAATGAGTTAATCAATCCAATGTTTGGTC

CCTCAGGTGTTTCAATTGGACACATACGGCCATAGTGAGAGTAGTGAACG

TCACGTACTTCCATTTGAGCACGTTCACGTGTTAAACCACCAGGTCCTAA

TGCCGATAG-3'

SEQ ID NO:38: Partial sequence of the rpoB gene in *Staphylococcus arlettae*, measuring 518 base pairs:

(SEQ ID NO: 38)
5'TTCACGGTTCATCAACGGTACTGCTTGACGTTGCATGTTCGCACCCAT

TAATGCACGGTTAGAGTCATCGTTTTCTAAGAAAGGAATACATGCCGTTG

CAGCTGAAACTACTTGCTTAGGTGATACGTCCATGTAGTCCATTTTTTCT

TTAGCCATAACTGTGTTATTACCGCGGAAACGACAAACAACTTCGTCATC

TAAAAACTTACCATTTTCATCTAAGTTAGAGTTGGCTTGTGCTACCACAT

AGCTGTCCTCTTCATCAGCAGTTAGGTAATCAATTTGATCTGTAATTGAG

TTTGTTGCTAAATCTACTTTACGGTACGGCGTTTCGATAAAGCCAAATTC

ATTTACACGTGCATAACTTGATAGTGAGTTAATTAAACCGATGTTTGGTC

CCTCTGGTGTTTCGATAGGACACATACGGCCATAGTGAGAATAGTGTACG

TCACGTACTTCCATTTGAGCACGTTCACGTGTTAAACCACCAGGTCCTAA

TGCTGATAAACGACGTTTAT-3'

SEQ ID NO:39: Partial sequence of the rpoB gene in *Staphylococcus caprae*, measuring 556 base pairs:

(SEQ ID NO: 39)
5'TAACCCATTAGCTGAGTTGACTCATAAACGTCGTCTATCAGCATTAGG

ACCTGGTGGTTTAACGCGTGAACGTGCCCAAATGGAAGTGCGTGACGTTC

ACTATTCTCACTATGGCCGTATGTGTCCAATCGAAACACCTGAGGGACCA

-continued

```
AACATTGGTTTAATCAACTCATTATCAAGTTATGCACGAGTAAATGAATT

TGGTTTTATTGAAACACCTTATCGTAAAGTAGATTTAGATACGAATTCTA

TCACTGACCAAATTGATTACTTAACTGCTGATGAAGAAGATAGTTATGTT

GTTGCCCAAGCGAACTCTCGTTTAGACGAAAATGGTCGTTTCTTAGATGA

CGAAGTTGTTTGTCGTTTCCGTGGTAATAACACAGTTATGGCTAAAGAGA

AAATGGACTACATGGATGTATCTCCTAAACAAGTAGTATCTGCAGCGACA

GCTTGTATTCCATTCTTAGAAAATGATGACTCTAACCGTGCATTAATGGG

TGCGAACATGCAACGTCAAGCAGTACCATTGATGAATCCAGAAGCGCCAT

TTGTTGGT-3'
```

EXAMPLE 3

Blind Identification of a Collection of 20 Bacterial Strains Comprising 10 Strains of Bacteria Belonging to the *Staphylococcus* Genus A collection of twenty strains belonging to the following bacterial species: *Staphylococcus aureus* (strain sensitive to rifampicin), *Staphylococcus aureus* (strain resistant to rifampicin), *Staphylococcus epidermis*, *Staphylococcus haemolyticus*, *Staphylococcus saprophyticus*, *Staphylococcus intermedius*, *Staphylococcus equorum*, *Staphylococcus schleiferi*, *Staphylococcus lugdunensis*, *Staphylococcus gallinarum*, *Escherichia coli*, *Pseudomonas aeruginosa*, *Streptococcus pneumoniae*, *Enterococcus faecalis*, *Streptococcus pyogenes*, *Corynebacterium amycolatum*, *Gemella morbilorum*, *Acinetobacter anitratus*, *Micrococcus luteus* and *Propionibacterium acnes* was encoded so as to conduct blind molecular identification of the strains (the experimenter being unaware of strain identity) using the method described in this patent application. Extraction of the nucleic acids and amplification of the fragment of 751 base pairs of the rpoB gene were performed as described in example no 2 incorporating the primers SEQ ID NO:7 (as 5' primer) and SEQ ID NO:10 (as 3' primer) in a PCR amplification (FIG. 1). The sequencing of these 10 amplicons was conducted by incorporating within the sequencing reaction the primers SEQ ID NO:9 (5' primer) and SEQ ID NO:10 (3' primer) as described in example 2 and a comparison of the sequences obtained with the sequences of the data bank for sequences SEQ ID NOs:11 to 39 made it possible to identify the ten amplified strains as being: *Staphylococcus aureus*, *Staphylococcus aureus*, *Staphylococcus epidermis*, *Staphylococcus haemolyticus*, *Staphylococcus saprophyticus*, *Staphylococcus intermedius*, *Staphylococcus equorum*, *Staphylococcus schleiferi*, *Staphylococcus lugdunensis* and *Staphylococcus gallinarum*. The decoding of these 20 strains showed 100% agreement between the molecular identification following the method that is the subject hereof and the identification established previously using standard phenotype methods. This result illustrates the specificity of the primer sets SEQ ID NO: 7/SEQ ID NO:10 and SEQ ID NO: 9/SEQ ID NO:10 used for this work and the fact that the level of sensitivity of *Staphylococcus aureus* strains to rifampicin does not interfere with the identification of these strains.

The other bacteria chosen because they are frequently isolated in human or animal clinical samples and also likely to contain bacteria of the *Staphylococcus* genus, were not amplified, thereby demonstrating the specificity of the primers used for the *Staphylococcus* genus under conditions of use to detect bacteria of the *Staphylococcus* genus using the method of the invention, relative to bacteria of another genus.

FIG. 1 shows the PCR amplification products obtained from fifteen encoded bacterial strains, comprising 10 strains belonging to the *Staphylococcus* genus (columns 2 to 5, 8, 9, 11 to 13 and 16) and 5 bacterial strains of bacterial geni other than *Staphylococcus* (columns 6, 7, 10, 14 and 15). Columns 1 and 17 represent the molecular weight labeler. Columns corresponding to negative amplification controls (sterile water) and to strains other than *Staphylococcus* are not shown. The amplification products are obtained after incorporating primers SEQ ID NO:7 and SEQ ID NO:10 according to the invention and are visualized by ethidium bromide staining after electrophoresis on agarose gel.

The invention claimed is:

1. A method of detecting a bacterium belonging to the *Staphylococcus* genus, the method comprising:
   (a) contacting a sample containing a nucleic acid of a bacterium with amplification primers, the amplification primers comprising a 3' primer and a 5' primer;
   (b) amplifying a nucleic acid present in the sample by an enzymatic polymerization reaction; and
   (c) determining the presence of amplification product, wherein the presence of amplification product indicates the presence of a bacterium belonging to the *Staphylococcus* genus in the sample;
   wherein:
   the 3' primer comprises at least one member selected from the group consisting of:
      a primer comprising at least 12 consecutive nucleotides of the sequence set forth in SEQ ID NO:8;
      a primer comprising at least 12 consecutive nucleotides of the sequence set forth in SEQ ID NO:10, where each n represents inosine;
      a mixture of primers each comprising at least 12 consecutive nucleotides of the sequence set forth in SEQ ID NO:10, where each n independently represents A, T, C, or G and wherein, for the mixture, A, T, C, and G are represented at each n in an equimolar amount; and
      a mixture of primers each comprising at least 12 consecutive nucleotides of the sequence set forth in SEQ ID NO:10, wherein:
         n at nucleotide 3 of SEQ ID NO:10 is inosine for each primer of the mixture or is represented by A, T, C, and G in equimolar amounts in the mixture;
         n at nucleotide 6 of SEQ ID NO:10 is inosine for each primer of the mixture or is represented by A, T, C, and G in equimolar amounts in the mixture; and
         n at nucleotide 9 of SEQ ID NO:10 is inosine for each primer of the mixture or is represented by A, T, C, and G in equimolar amounts in the mixture; and
   the 5' primer comprises at least one member selected from the group consisting of:
      a primer comprising at least 12 consecutive nucleotides of the sequence set forth in SEQ ID NO:9;
      a primer comprising at least 12 consecutive nucleotides of the sequence set forth in SEQ ID NO:7, where n represents inosine; and
      a mixture of primers each comprising at least 12 consecutive nucleotides of the sequence set forth in SEQ ID NO:7, wherein n represents A, T, C, or G and wherein, for the mixture, A, T, C, and G are represented at that n in an equimolar amount;
   wherein the method indicates that a bacterium of the *Staphylococcus* genus is present in the sample if any species selected from the group consisting of *Staphylococcus xylosus, Staphylococcus warneri, Staphylococcus simulans, Staphylococcus sciuri, Staphylococcus schleiferi, Staphylococcus saprophyticus, Staphylococcus saccharolyticus, Staphylococcus pulveris, Staphylococcus muscae, Staphylococcus lugdunensis, Staphylococcus lentis, Staphylococcus kloosii, Staphylococcus intermedius, Staphylococcus hyicus, Staphylococcus hominis, Staphylococcus haemolyticus, Staphylococcus gallinarum, Staphylococcus felis, Staphylococcus equorum, Staphylococcus epidermidis, Staphylococcus cohni,*

*Staphylococcus chromogenes, Staphylococcus carnosus, Staphylococcus capitis, Staphylococcus auricularis, Staphylococcus aureus* subs. *aureus, Staphylococcus aureus* subs. *anaerobius, Staphylococcus arlettae,* and *Staphylococcus caprae* is present in the sample, with the exception that the primer comprising at least 12 consecutive nucleotides of the sequence set forth in SEQ ID NO:8 is not capable of detecting the presence of *Staphylococcus schleiferi*.

2. The method of claim 1, wherein:
the 3' primer comprises at least one member selected from the group consisting of:
  a primer comprising the sequence set forth in SEQ ID NO:8;
  a primer comprising the sequence set forth in SEQ ID NO:10, where each n represents inosine;
  a mixture of primers each comprising the sequence set forth in SEQ ID NO:10, where each n independently represents A, T, C, or G and wherein, for the mixture, A, T, C, and G are represented at each n in an equimolar amount; and
  a mixture of primers each comprising the sequence set forth in SEQ ID NO:10, wherein:
    n at nucleotide 3 of SEQ ID NO:10 is inosine for each primer of the mixture or is represented by A, T, C, and G in equimolar amounts in the mixture;
    n at nucleotide 6 of SEQ ID NO:10 is inosine for each primer of the mixture or is represented by A, T, C, and G in equimolar amounts in the mixture; and
    n at nucleotide 9 of SEQ ID NO:10 is inosine for each primer of the mixture or is represented by A, T, C, and G in equimolar amounts in the mixture; and
the 5' primer comprises at least one member selected from the group consisting of:
  a primer comprising the sequence set forth in SEQ ID NO:9;
  a primer comprising the sequence set forth in SEQ ID NO:7, where n represents inosine; and
  a mixture of primers each comprising the sequence set forth in SEQ ID NO:7, wherein n represents A, T, C, or G and wherein, for the mixture, A, T, C, and G are represented at that n in an equimolar amount.

3. The method of claim 1, wherein:
the 3' primer comprises at least one primer comprising the sequence set forth in SEQ ID NO:10, where each n represents inosine; and
the 5' primer comprises at least one primer comprising the sequence set forth in SEQ ID NO:7, where n represents inosine.

4. The method of claim 1, wherein:
the 3' primer comprises at least one member selected from the group consisting of:
  a primer consisting of the sequence set forth in SEQ ID NO:10, where each n represents inosine;
  a mixture of primers each consisting of the sequence set forth in SEQ ID NO:10, where each n independently represents A, T, C, or G and wherein, for the mixture, A, T, C, and G are represented at each n in an equimolar amount; and
  a mixture of primers each consisting of the sequence set forth in SEQ ID NO:10, wherein:
    n at nucleotide 3 of SEQ ID NO:10 is inosine for each primer of the mixture or is represented by A, T, C, and G in equimolar amounts in the mixture;
    n at nucleotide 6 of SEQ ID NO:10 is inosine for each primer of the mixture or is represented by A, T, C, and G in equimolar amounts in the mixture; and
    n at nucleotide 9 of SEQ ID NO:10 is inosine for each primer of the mixture or is represented by A, T, C, and G in equimolar amounts in the mixture; and
the 5' primer comprises at least one member selected from the group consisting of:
  a primer consisting of the sequence set forth in SEQ ID NO:9;
  a primer consisting of the sequence set forth in SEQ ID NO:7, where n represents inosine; and
  a mixture of primers each consisting of the sequence set forth in SEQ ID NO:7, wherein n represents A, T, C, or G and wherein, for the mixture, A, T, C, and G are represented at that n in an equimolar amount.

5. The method of claim 4, wherein:
the 3' primer comprises at least one primer consisting of the sequence set forth in SEQ ID NO:10, where each n represents inosine; and
the 5' primer comprises at least one primer consisting of the sequence set forth in SEQ ID NO:7, where n represents inosine.

6. A method of detecting a species of bacterium belonging to the *Staphylococcus* genus, the species of the bacterium belonging to the group consisting of *Staphylococcus xylosus, Staphylococcus warneri, Staphylococcus simulans, Staphylococcus sciuri, Staphylococcus schleiferi, Staphylococcus saphrophyticus, Staphylococcus saccharolyticus, Staphylococcus pulveris, Staphylococcus muscae, Staphylococcus lugdunensis, Staphylococcus lentis, Staphylococcus kloosii, Staphylococcus intermedius, Staphylococcus hyicus, Staphylococcus hominis, Staphylococcus haemolyticus, Staphylococcus gallinarum, Staphylococcus felis, Staphylococcus equorum, Staphylococcus epidermidis, Staphylococcus cohni, Staphylococcus chromogenes, Staphylococcus carnosus, Staphylococcus capitis, Staphylococcus auricularis, Staphylococcus aureus* subs. *aureus, Staphylococcus aureus* subs. *anaerobius, Staphylococcus arlettae, Staphylococcus caprae,* the method comprising:

(a) performing a sequencing reaction on an amplified rpoB gene fragment of a bacterium using nucleotide sequencing primers, the nucleotide sequencing primers comprising a 3' sequencing primer and a 5' sequencing primer; and (b) determining whether the bacterium belongs to a given species of the *Staphylococcus* genus by comparing the sequence of said fragment obtained with a sequence selected from the group consisting of SEQ ID NOs:11-39, and full-length complementary sequences thereof, wherein it is indicative that the bacterium belongs to the *Staphylococcus* species if the sequence obtained is identical to the sequence selected from the group consisting of SEQ ID NOs:11-39;

wherein:
the 3' sequencing primer comprises at least one member selected from the group consisting of:
  a primer comprising at least 12 consecutive nucleotides of the sequence set forth in SEQ ID NO:10, where each n represents inosine;
  a mixture of primers each comprising at least 12 consecutive nucleotides of the sequence set forth in SEQ ID NO:10, where each n independently represents A, T, C, or G and wherein, for the mixture, A, T, C, and G are represented at each n in an equimolar amount; and
  a mixture of primers each comprising at least 12 consecutive nucleotides of the sequence set forth in SEQ ID NO:10, wherein:

n at nucleotide 3 of SEQ ID NO:10 is inosine for each primer of the mixture or is represented by A, T, C, and G in equimolar amounts in the mixture;

n at nucleotide 6 of SEQ ID NO:10 is inosine for each primer of the mixture or is represented by A, T, C, and G in equimolar amounts in the mixture; and n at nucleotide 9 of SEQ ID NO:10 is inosine for each primer of the mixture or is represented by A, T, C, and G in equimolar amounts in the mixture; and the 5' sequencing primer comprises at least one member selected from the group consisting of:

a primer comprising at least 12 consecutive nucleotides of the sequence set forth in SEQ ID NO:9;

a primer comprising at least 12 consecutive nucleotides of the sequence set forth in SEQ ID NO:7, where n represents inosine; and a mixture of primers each comprising at least 12 consecutive nucleotides of the sequence set forth in SEQ ID NO:7, wherein n represents A, T, C, or G and wherein, for the mixture, A, T, C, and G are represented at that n in an equimolar amount.

7. The method of claim 6, wherein:

the 3' sequencing primer comprises at least one member selected from the group consisting of:

a primer comprising the sequence set forth in SEQ ID NO:10, where each n represents inosine;

a mixture of primers each comprising the sequence set forth in SEQ ID NO:10, where each n independently represents A, T, C, or G and wherein, for the mixture, A, T, C, and G are represented at each n in an equimolar amount; and a mixture of primers each comprising the sequence set forth in SEQ ID NO:10, wherein:

n at nucleotide 3 of SEQ ID NO:10 is inosine for each primer of the mixture or is represented by A, T, C, and G in equimolar amounts in the mixture;

n at nucleotide 6 of SEQ ID NO:10 is inosine for each primer of the mixture or is represented by A, T, C, and G in equimolar amounts in the mixture; and n at nucleotide 9 of SEQ ID NO:10 is inosine for each primer of the mixture or is represented by A, T, C, and G in equimolar amounts in the mixture; and the 5' sequencing primer comprises at least one member selected from the group consisting of:

a primer comprising the sequence set forth in SEQ ID NO:9;

a primer comprising the sequence set forth in SEQ ID NO:7, where n represents inosine; and a mixture of primers each comprising the sequence set forth in SEQ ID NO:7, wherein n represents A, T, C, or G and wherein, for the mixture, A, T, C, and G are represented at that n in an equimolar amount.

8. The method of claim 6, wherein:

the 3' sequencing primer is at least one primer consisting of the sequence set forth in SEQ ID NO:10, where each n represents inosine; and the 5' sequencing primer comprises at least one member selected from the group consisting of:

a primer consisting of the sequence set forth in SEQ ID NO:9; and a primer consisting of the sequence set forth in SEQ ID NO:7, where n represents inosine.

9. The method of claim 6, wherein:

the amplified rpoB gene fragment is obtained by first amplification of a nucleic acid of said sample with a pair of 5' and 3' amplification primers, wherein:

the 5' amplification primer comprises at least one member selected from the group consisting of:

a primer comprising at least 12 consecutive nucleotides of the sequence set forth in SEQ ID NO:7, where n represents inosine; and a mixture of primers each comprising at least 12 consecutive nucleotides of the sequence set forth in SEQ ID NO:7, wherein n represents A, T, C, or G and wherein, for the mixture, A, T, C, and G are represented at that n in an equimolar amount, and the 3' amplification primer comprises at least one member selected from the group consisting of:

a primer comprising at least 12 consecutive nucleotides of the sequence set forth in SEQ ID NO:10, where each n represents inosine;

a mixture of primers each comprising at least 12 consecutive nucleotides of the sequence set forth in SEQ ID NO:10, where each n independently represents A, T, C, or G and wherein, for the mixture, A, T, C, and G are represented at each n in an equimolar amount; and a mixture of primers each comprising at least 12 consecutive nucleotides of the sequence set forth in SEQ ID NO:10, wherein:

n at nucleotide 3 of SEQ ID NO:10 is inosine for each primer of the mixture or is represented by A, T, C, and G in equimolar amounts in the mixture;

n at nucleotide 6 of SEQ ID NO:10 is inosine for each primer of the mixture or is represented by A, T, C, and G in equimolar amounts in the mixture; and n at nucleotide 9 of SEQ ID NO:10 is inosine for each primer of the mixture or is represented by A, T, C, and G in equimolar amounts in the mixture; and the 5' sequencing primer comprises at least one primer comprising the sequence set forth in SEQ ID NO:9.

10. The method of claim 9, wherein:

the 3' amplification primer comprises at least one member selected from the group consisting of:

a primer comprising the sequence set forth in SEQ ID NO:10, where each n represents inosine;

a mixture of primers each comprising the sequence set forth in SEQ ID NO:10, where each n independently represents A, T, C, or G and wherein, for the mixture, A, T, C, and G are represented at each n in an equimolar amount; and a mixture of primers each comprising the sequence set forth in SEQ ID NO:10, wherein:

n at nucleotide 3 of SEQ ID NO:10 is inosine for each primer of the mixture or is represented by A, T, C, and G in equimolar amounts in the mixture;

n at nucleotide 6 of SEQ ID NO:10 is inosine for each primer of the mixture or is represented by A, T, C, and G in equimolar amounts in the mixture; and n at nucleotide 9 of SEQ ID NO:10 is inosine for each primer of the mixture or is represented by A, T, C, and G in equimolar amounts in the mixture; and the 5' amplification primer comprises at least one member selected from the group consisting of:

a primer comprising the sequence set forth in SEQ ID NO:7, where n represents inosine; and a mixture of primers each comprising the sequence set forth in SEQ ID NO:7, wherein n represents A, T, C, or G and wherein, for the mixture, A, T, C, and G are represented at that n in an equimolar amount.

11. The method of claim 9, wherein:
the 3' sequencing primer comprises at least one member selected from the group consisting of:
a primer consisting of the sequence set forth in SEQ ID NO:10, where each n represents inosine;
a mixture of primers each consisting of the sequence set forth in SEQ ID NO:10, where each n independently represents A, T, C, or G and wherein, for the mixture, A, T, C, and G are represented at each n in an equimolar amount; and
a mixture of primers each consisting of the sequence set forth in SEQ ID NO:10, wherein:
n at nucleotide 3 of SEQ ID NO:10 is inosine for each primer of the mixture or is represented by A, T, C, and G in equimolar amounts in the mixture;
n at nucleotide 6 of SEQ ID NO:10 is inosine for each primer of the mixture or is represented by A, T, C, and G in equimolar amounts in the mixture; and
n at nucleotide 9 of SEQ ID NO:10 is inosine for each primer of the mixture or is represented by A, T, C, and G in equimolar amounts in the mixture; and
the 5' sequencing primer comprises at least one primer consisting of the sequence set forth in SEQ ID NO:9.

12. At least one isolated oligonucleotide or mixture of oligonucleotides selected from the group consisting of:
an oligonucleotide having no more than 35 nucleotides, the oligonucleotide comprising the sequence set forth in SEQ ID NO:8, or the full-length complementary sequence thereof;
an oligonucleotide having no more than 35 nucleotides, the oligonucleotide comprising the sequence set forth in SEQ ID NO:9, or of the full-length complementary sequence thereof;
an oligonucleotide having no more than 35 nucleotides, the oligonucleotide comprising the sequence set forth in SEQ ID NO:7, or the full-length complementary sequence thereof, where n represents inosine;
a mixture of oligonucleotides each having no more than 35 nucleotides and each comprising the sequence set forth in SEQ ID NO:7, or the full-length complementary sequence thereof, wherein n represents A, T, C, or G and wherein, for the mixture, A, T, C, and G are represented at that n in an equimolar amount;
an oligonucleotide having no more than 35 nucleotides, the oligonucleotide comprising the sequence set forth in SEQ ID NO: 10, or the full-length complementary sequence thereof, where each n represents inosine;
a mixture of oligonucleotides each having no more than 35 nucleotides and each comprising the sequence set forth in SEQ ID NO: 10, or the full-length complementary sequence thereof, where each n independently represents A, T, C, or G and wherein, for the mixture, A, T, C, and G are represented at each n in an equimolar amount;
and a mixture of oligonucleotides each having no more than 35 nucleotides and each comprising the sequence set forth in SEQ ID NO: 10, or the full-length complementary sequence thereof, wherein:
n at nucleotide 3 of SEQ ID NO: 10 is inosine for each oligonucleotide of the mixture or is represented by A, T, C, and G in equimolar amounts in the mixture;
n at nucleotide 6 of SEQ ID NO: 10 is inosine for each oligonucleotide of the mixture or is represented by A, T, C, and G in equimolar amounts in the mixture; and
n at nucleotide 9 of SEQ ID NO: 10 is inosine for each oligonucleotide of the mixture or is represented by A, T, C, and G in equimolar amounts in the mixture.

13. The at least one isolated oligonucleotide or mixture of oligonucleotides of claim 12, wherein said at least one oligonucleotide consists of a sequence selected from the group consisting of:
the sequence set forth in SEQ ID NO:7, or its full-length complementary sequence, where n is inosine;
the sequence set forth in SEQ ID NO:8, of its full-length complementary sequence thereof;
the sequence set forth in SEQ ID NO:9, of its full-length complementary sequence thereof; and
the sequence set forth in SEQ ID NO:10, or its full-length complementary sequence, where each n is inosine.

14. A method of detecting whether a sample contains any bacteria belonging to the *Staphylococcus* genus, the method comprising:
(a) contacting the sample with amplification primers, the amplification primers comprising a 3' primer and a 5' primer;
(b) amplifying a nucleic acid present in the sample by an enzymatic polymerization reaction; and
(c) determining the presence of amplification product, wherein the presence of amplification product indicates the presence of a bacterium belonging to the *Staphylococcus* genus in the sample;
wherein:
the 3' primer comprises at least one member selected from the group consisting of:
a primer comprising the sequence set forth in SEQ ID NO:8;
a primer comprising the sequence set forth in SEQ ID NO:10, where each n represents inosine;
a mixture of primers each comprising the sequence set forth in SEQ ID NO:10, where each n independently represents A, T, C, or G and wherein, for the mixture, A, T, C, and G are represented at each n in an equimolar amount; and
a mixture of primers each comprising the sequence set forth in SEQ ID NO:10, wherein:
n at nucleotide 3 of SEQ ID NO:10 is inosine for each primer of the mixture or is represented by A, T, C, and G in equimolar amounts in the mixture;
n at nucleotide 6 of SEQ ID NO:10 is inosine for each primer of the mixture or is represented by A, T, C, and G in equimolar amounts in the mixture; and
n at nucleotide 9 of SEQ ID NO:10 is inosine for each primer of the mixture or is represented by A, T, C, and G in equimolar amounts in the mixture; and
the 5' primer comprises at least one member selected from the group consisting of:
a primer comprising the sequence set forth in SEQ ID NO:9;
a primer comprising the sequence set forth in SEQ ID NO:7, where n represents inosine; and
a mixture of primers each comprising the sequence set forth in SEQ ID NO:7, wherein n represents A, T, C, or G and wherein, for the mixture, A, T, C, and G are represented at that n in an equimolar amount.

15. The method of claim 14, wherein:
the 3' primer comprises at least one primer comprising the sequence set forth in SEQ ID NO:10, where each n represents inosine; and
the 5' primer comprises at least one primer comprising the sequence set forth in SEQ ID NO:7, where n represents inosine.

16. The method of claim 14, wherein:
the 3' primer comprises at least one member selected from the group consisting of:

a primer consisting of the sequence set forth in SEQ ID NO:10, where each n represents inosine;
a mixture of primers each consisting of the sequence set forth in SEQ ID NO:10, where each n independently represents A, T, C, or G and wherein, for the mixture, A, T, C, and G are represented at each n in an equimolar amount; and
a mixture of primers each consisting of the sequence set forth in SEQ ID NO:10, wherein:
n at nucleotide 3 of SEQ ID NO:10 is inosine for each primer of the mixture or is represented by A, T, C, and G in equimolar amounts in the mixture;
n at nucleotide 6 of SEQ ID NO:10 is inosine for each primer of the mixture or is represented by A, T, C, and G in equimolar amounts in the mixture; and
n at nucleotide 9 of SEQ ID NO:10 is inosine for each primer of the mixture or is represented by A, T, C, and G in equimolar amounts in the mixture; and
the 5' primer comprises at least one member selected from the group consisting of:
a primer consisting of the sequence set forth in SEQ ID NO:9;
a primer consisting of the sequence set forth in SEQ ID NO:7, where n represents inosine; and
a mixture of primers each consisting of the sequence set forth in SEQ ID NO:7, wherein n represents A, T, C, or G and wherein, for the mixture, A, T, C, and G are represented at that n in an equimolar amount.

17. The method of claim 16, wherein:
the 3' primer comprises at least one primer consisting of the sequence set forth in SEQ ID NO:10, where each n represents inosine; and
the 5' primer comprises at least one primer consisting of the sequence set forth in SEQ ID NO:7, where n represents inosine.

18. A method of detecting a species of bacterium belonging to the *Staphylococcus* genus, the species of the bacterium belonging to the group consisting of *Staphylococcus xylosus, Staphylococcus warneri, Staphylococcus simulans, Staphylococcus sciuri, Staphylococcus schleiferi, Staphylococcus saprophyticus, Staphylococcus saccharolyticus, Staphylococcus pulveris, Staphylococcus muscae, Staphylococcus lugdunensis, Staphylococcus lentis, Staphylococcus kloosii, Staphylococcus intermedius, Staphylococcus hyicus, Staphylococcus hominis, Staphylococcus haemolyticus, Staphylococcus gallinarum, Staphylococcus felis, Staphylococcus equorum, Staphylococcus epidermidis, Staphylococcus cohni, Staphylococcus chromogenes, Staphylococcus carnosus, Staphylococcus capitis, Staphylococcus auricularis, Staphylococcus aureus* subs. *aureus, Staphylococcus aureus* subs. *anaerobius, Staphylococcus arlettae, Staphylococcus caprae*, the method comprising:
(a) performing a sequencing reaction on an amplified rpoB gene fragment of a bacterium using nucleotide sequencing primers, the nucleotide sequencing primers comprising a 3' sequencing primer and a 5' sequencing primer; and
(b) determining whether the bacterium belongs to a given species of the *Staphylococcus* genus by comparing the sequence of said fragment obtained with a sequence selected from the group consisting of SEQ ID NOs:11-39, and full-length complementary sequences thereof, wherein it is indicative that the bacterium belongs to the *Staphylococcus* species if the sequence obtained is identical to the sequence selected from the group consisting of SEQ ID NOs:11-39;

wherein:
the 3' sequencing primer comprises at least one member selected from the group consisting of:
a primer comprising the sequence set forth in SEQ ID NO:10, where each n represents inosine;
a mixture of primers each comprising the sequence set forth in SEQ ID NO:10, where each n independently represents A, T, C, or G and wherein, for the mixture, A, T, C, and G are represented at each n in an equimolar amount; and
a mixture of primers each comprising the sequence set forth in SEQ ID NO:10, wherein:
n at nucleotide 3 of SEQ ID NO:10 is inosine for each primer of the mixture or is represented by A, T, C, and G in equimolar amounts in the mixture;
n at nucleotide 6 of SEQ ID NO:10 is inosine for each primer of the mixture or is represented by A, T, C, and G in equimolar amounts in the mixture; and
n at nucleotide 9 of SEQ ID NO:10 is inosine for each primer of the mixture or is represented by A, T, C, and G in equimolar amounts in the mixture; and
the 5' sequencing primer comprises at least one member selected from the group consisting of:
a primer comprising the sequence set forth in SEQ ID NO:9;
a primer comprising the sequence set forth in SEQ ID NO:7, where n represents inosine; and
a mixture of primers each comprising the sequence set forth in SEQ ID NO:7, wherein n represents A, T, C, or G and wherein, for the mixture, A, T, C, and G are represented at that n in an equimolar amount.

19. The method of claim 18, wherein:
the amplified rpoB gene fragment is obtained by first amplification of a nucleic acid of said sample with a pair of 5' and 3' amplification primers, wherein:
the 3' amplification primer comprises at least one member selected from the group consisting of:
a primer comprising the sequence set forth in SEQ ID NO:10, where each n represents inosine;
a mixture of primers each comprising the sequence set forth in SEQ ID NO:10, where each n independently represents A, T, C, or G and wherein, for the mixture, A, T, C, and G are represented at each n in an equimolar amount; and
a mixture of primers each comprising the sequence set forth in SEQ ID NO:10, wherein:
n at nucleotide 3 of SEQ ID NO:10 is inosine for each primer of the mixture or is represented by A, T, C, and G in equimolar amounts in the mixture;
n at nucleotide 6 of SEQ ID NO:10 is inosine for each primer of the mixture or is represented by A, T, C, and G in equimolar amounts in the mixture; and
n at nucleotide 9 of SEQ ID NO:10 is inosine for each primer of the mixture or is represented by A, T, C, and G in equimolar amounts in the mixture; and
the 5' amplification primer comprises at least one member selected from the group consisting of:
a primer comprising the sequence set forth in SEQ ID NO:7, where n represents inosine; and
a mixture of primers each comprising the sequence set forth in SEQ ID NO:7, wherein n represents A, T, C, or G and wherein, for the mixture, A, T, C, and G are represented at that n in an equimolar amount; and
the 5' sequencing primer comprises at least one primer comprising the sequence set forth in SEQ ID NO:9.

20. The method of claim 19, wherein:

the 3' sequencing primer comprises at least one member selected from the group consisting of:

a primer consisting of the sequence set forth in SEQ ID NO:10, where each n represents inosine;

a mixture of primers each consisting of the sequence set forth in SEQ ID NO:10, where each n independently represents A, T, C, or G and wherein, for the mixture, A, T, C, and G are represented at each n in an equimolar amount; and a mixture of primers each consisting of the sequence set forth in SEQ ID NO:10, wherein:

n at nucleotide 3 of SEQ ID NO:10 is inosine for each primer of the mixture or is represented by A, T, C, and G in equimolar amounts in the mixture;

n at nucleotide 6 of SEQ ID NO:10 is inosine for each primer of the mixture or is represented by A, T, C, and G in equimolar amounts in the mixture; and n at nucleotide 9 of SEQ ID NO:10 is inosine for each primer of the mixture or is represented by A, T, C, and G in equimolar amounts in the mixture; and the 5' sequencing primer comprises at least one primer consisting of the sequence set forth in SEQ ID NO:9.

* * * * *